United States Patent
McMillan

(10) Patent No.: US 11,147,623 B2
(45) Date of Patent: Oct. 19, 2021

(54) METHOD FOR SKIN CANCER THERMAL THERAPY

(71) Applicant: gRadiant Research, LLC, Concord, MA (US)

(72) Inventor: Kathleen McMillan, Westford, MA (US)

(73) Assignee: GRADIANT RESEARCH, LLC, Concord, MA (US)

( * ) Notice: Subject to any disclaimer, the term of this patent is extended or adjusted under 35 U.S.C. 154(b) by 0 days.

(21) Appl. No.: 15/970,742

(22) Filed: May 3, 2018

(65) Prior Publication Data
US 2018/0325593 A1 Nov. 15, 2018

Related U.S. Application Data

(62) Division of application No. 13/878,185, filed as application No. PCT/US2011/055397 on Oct. 7, 2011, now Pat. No. 9,962,225.
(Continued)

(51) Int. Cl.
*A61B 18/20* (2006.01)
*A61B 5/01* (2006.01)
(Continued)

(52) U.S. Cl.
CPC ............. *A61B 18/20* (2013.01); *A61B 5/01* (2013.01); *A61B 18/203* (2013.01); *A61N 5/062* (2013.01);
(Continued)

(58) Field of Classification Search
CPC ........... A61N 5/062; A61N 2005/0652; A61N 5/0601; A61N 2005/067; A61N 5/0616;
(Continued)

(56) References Cited

U.S. PATENT DOCUMENTS

| 4,638,436 A | * | 1/1987 | Badger ................... A61N 7/02 600/549 |
| 5,328,488 A | | 7/1994 | Daikuzuno |

(Continued)

FOREIGN PATENT DOCUMENTS

| CN | 1053540 | 8/1991 |
| CN | 1665453 | 9/2005 |

(Continued)

OTHER PUBLICATIONS

Stearns, M.P., "The relationship between adenoid weight to tonsillar weight," J. Laryngol, Otol., 97: 519-521 (1983).
(Continued)

*Primary Examiner* — Gary Jackson
*Assistant Examiner* — Sebastian X Lukjan
(74) *Attorney, Agent, or Firm* — Hamilton, Brook, Smith & Reynolds, P.C.

(57) ABSTRACT

An apparatus for treatment of soft tissue includes a source of radiation, a handpiece which is adapted to transmit radiation emitted from the source of radiation to a region of soft tissue, resulting in irradiated soft tissue, said handpiece being positioned adjacent to or in contact with said soft tissue region, a grid element adapted to hold at least one temperature sensor in contact with or embedded in said region of soft tissue, and a microprocessor, which converts a signal from the at least one temperature sensor into a measure of damage produced in at least two components of the irradiated soft tissue, said components comprising at least one normal tissue component and at least one malignant, hypertrophic, diseased, or unwanted component.

32 Claims, 25 Drawing Sheets

Related U.S. Application Data

(60) Provisional application No. 61/390,838, filed on Oct. 7, 2010.

(51) Int. Cl.

| | | |
|---|---|---|
| *A61N 5/06* | (2006.01) | |
| *A61B 18/00* | (2006.01) | |
| *A61B 18/22* | (2006.01) | |
| *A61B 18/24* | (2006.01) | |
| *A61F 9/008* | (2006.01) | |
| *A61N 5/067* | (2006.01) | |

(52) U.S. Cl.
CPC .......... *A61N 5/0616* (2013.01); *A61B 18/201* (2013.01); *A61B 18/22* (2013.01); *A61B 18/24* (2013.01); *A61B 2018/00023* (2013.01); *A61B 2018/00452* (2013.01); *A61B 2018/00476* (2013.01); *A61B 2018/00791* (2013.01); *A61F 9/008* (2013.01); *A61N 5/0601* (2013.01); *A61N 2005/067* (2013.01); *A61N 2005/0652* (2013.01); *A61N 2005/0659* (2013.01)

(58) Field of Classification Search
CPC .... A61N 2005/0644; A61N 2005/0659; A61B 18/20; A61B 18/203; A61B 5/01; A61B 2018/00452; A61B 18/22; A61B 18/201; A61B 2018/00476; A61B 18/24; A61B 2018/00023; A61B 2018/00791; A61F 9/008
See application file for complete search history.

(56) References Cited

U.S. PATENT DOCUMENTS

| | | | |
|---|---|---|---|
| 5,445,146 | A | 8/1995 | Bellinger |
| 5,658,275 | A | 8/1997 | Saadat |
| 5,861,020 | A | 1/1999 | Schwarzmaier |
| 5,951,596 | A | 9/1999 | Bellinger |
| 6,240,925 | B1 | 6/2001 | McMillan et al. |
| 6,267,779 | B1 | 7/2001 | Gerdes |
| 6,290,713 | B1 | 9/2001 | Russell |
| 6,339,458 | B1 | 1/2002 | Ohkawa |
| 6,389,313 | B1 | 5/2002 | Marchitto et al. |
| 6,451,013 | B1 | 9/2002 | Bays et al. |
| 6,659,999 | B1 | 12/2003 | Anderson et al. |
| 6,682,501 | B1 | 1/2004 | Nelson et al. |
| 6,743,249 | B1 | 6/2004 | Lang |
| 6,746,473 | B2 | 6/2004 | Shanks et al. |
| 7,018,397 | B2 | 3/2006 | Neuberger |
| 7,043,287 | B1 | 5/2006 | Khalil et al. |
| 8,685,010 | B2 | 4/2014 | McMillan et al. |
| 9,554,856 | B2 | 1/2017 | McMillan et al. |
| 9,962,225 | B2 | 5/2018 | McMillan |
| 10,194,986 | B2 | 2/2019 | McMillan et al. |
| 2001/0025176 | A1 | 9/2001 | Ellsberry et al. |
| 2002/0058931 | A1 | 5/2002 | Parker et al. |
| 2004/0093042 | A1 | 5/2004 | Altshuler et al. |
| 2005/0143792 | A1 | 6/2005 | Jay |
| 2005/0215987 | A1 | 9/2005 | Slatkine |
| 2006/0047329 | A1 | 3/2006 | Krespi et al. |
| 2006/0058712 | A1 | 3/2006 | Altshuler et al. |
| 2006/0184163 | A1* | 8/2006 | Breen .................... A61B 18/04 606/20 |
| 2007/0027440 | A1 | 2/2007 | Altshuler et al. |
| 2007/0185188 | A1 | 8/2007 | Mirejovsky et al. |
| 2007/0239232 | A1 | 10/2007 | Kurtz et al. |
| 2008/0021370 | A1 | 1/2008 | Borenstein |
| 2008/0228104 | A1 | 9/2008 | Uber et al. |
| 2008/0240172 | A1 | 10/2008 | Rizoiu et al. |
| 2008/0269849 | A1* | 10/2008 | Lewis .................. A61N 5/0613 607/91 |
| 2009/0112195 | A1 | 4/2009 | Zemmouri |
| 2009/0198309 | A1* | 8/2009 | Gowda .............. A61B 18/1815 607/102 |
| 2010/0049180 | A1* | 2/2010 | Wells .................. A61N 5/0616 606/12 |
| 2010/0145321 | A1* | 6/2010 | Altshuler ............. A61B 18/203 606/9 |
| 2010/0160904 | A1 | 6/2010 | McMillan et al. |
| 2010/0179530 | A1 | 7/2010 | Long et al. |
| 2011/0190749 | A1 | 8/2011 | McMillan et al. |
| 2012/0078160 | A1 | 3/2012 | McMillan |
| 2013/0197473 | A1 | 8/2013 | McMillan |
| 2013/0345687 | A1 | 12/2013 | McMillan et al. |
| 2014/0194770 | A1 | 7/2014 | McMillan et al. |
| 2017/0304003 | A1 | 10/2017 | McMillian |

FOREIGN PATENT DOCUMENTS

| | | |
|---|---|---|
| JP | 2001-046396 | 2/2001 |
| JP | 2001-204831 | 7/2001 |
| JP | 2006-051388 | 2/2006 |
| WO | 1986/001919 A1 | 3/1986 |
| WO | 1999/001696 | 1/1996 |
| WO | 2002/087698 A1 | 11/2002 |
| WO | 2008/049905 | 5/2008 |
| WO | 2008/131302 A2 | 10/2008 |
| WO | 2009/124301 A1 | 10/2009 |
| WO | 2010/060097 | 5/2010 |
| WO | 2010/102099 A1 | 9/2010 |
| WO | 2012/048241 | 4/2012 |

OTHER PUBLICATIONS

Storm, F.K., et al., "Normal Tissue and Solid Tumor Effects of Hyperthermia in Animal Models and Clinical Trials," Cancer Research, 36:2245-2251 (1979).

Sturesson, C., "Medical Laser-Induced Thermotherapy—Models and Applications," Doctoral Thesis, Department of Physics, Lund institute of Technology (1998).

Sukai, S.A., et al., "What Lies Beneath? A Lesson for the Clinician. Intraoperative Frozen Section Appearance of Persistent Basal Cell Carcinoma after Apparent Cure with Imiguirnod 5% Cream," Derm. Surg., 35: 1831-1834 (2009).

Tierney, E.P. and Hanke, C.W., "Cost Effective of Mohs Micrographic Surgery: Review of the Literature," J. Drugs Dermatol., 8: 914-922 (2009).

Windfuhr, J.P., et al., "Life threatening posttonsillectomy hemorrhage," Laryngoscope, 118 (2008).

Young, T., et al., "Epidemiology of Obstructive Sleep Apnea," Am. J. Respir. Crit. Care Med., 165: 1217-1239 (2002).

Zijistra, W.G., et al,, "Absorption Spectra of Human Fetal and Adult Oxyhemoglobin, De-Oxyhernogiobin, Carboxyhemoglobiri, and Methernogiobin," Clinical Chemistry vol. 37, No. 9, 1633-1638 (1991).

Advisory Action from U.S. Appl. No. 13/878,185, dated Sep. 10, 2014 entitled "Method and Apparatus for Skin Cancer Thermal Therapy".

Advisory Action from U.S. Appl. No. 13/878,185, dated Mar. 3, 2016 entitled "Method and Apparatus for Skin Cancer Thermal Therapy".

Final Office Action from U.S. Appl. No. 13/878,185, dated May 30, 2014 entitled "Method and Apparatus for Skin Cancer Thermal Therapy".

Final Office Action from U.S. Appl. No. 13/678,185, dated Nov. 2, 2015 entitled "Method and Apparatus for Skin Cancer Thermal Therapy".

Final Office Action from U.S. Appl. No. 13/878,185, dated Feb. 2, 2017 entitled "Method and Apparatus for Skin Cancer Thermal Therapy".

Interview Summary from U.S. Appl. No. 13/878,185, dated May 11, 2016 entitled "Method and Apparatus for Skin Cancer Thermal Therapy".

Interview Summary from U.S. Appl. No. 13/878,185, dated Aug. 3, 2016 entitled "Method and Apparatus for Skin Cancer Thermal Therapy".

(56) References Cited

OTHER PUBLICATIONS

Interview Summary from U.S. Appl. No. 13/878,185, dated Oct. 25, 2016 entitled "Method and Apparatus for Skin Cancer Thermal Therapy".
Interview Summary from U.S. Appl. No. 13/878,185, dated May 30, 2017 entitled "Method and Apparatus for Skin Cancer Thermal Therapy".
Interview Summary from U.S. Appl. No. 13/878,185, dated Nov. 29, 2017 entitled "Method and Apparatus for Skin Cancer Thermal Therapy".
Notice of Allowance for U.S. Appl. No. 13/878,185, dated Jan. 4, 2018.
Office Action from U.S. Appl. No. 13/878,185, dated Dec. 18, 2013 entitled "Method and Apparatus for Skin Cancer Thermal Therapy".
Office Action from U.S. Appl. No. 13/878,185, dated Apr. 1, 2015 entitled "Method and Apparatus for Skin Cancer Thermal Therapy".
Office Action from U.S. Appl. No. 13/878,185, dated Aug. 17, 2016 entitled "Method and Apparatus for Skin Cancer Thermal Therapy".
Office Action from U.S. Appl. No. 13/878,185, dated Aug. 28, 2017 entitled "Method and Apparatus for Skin Cancer Thermal Therapy".
Ahmed, M. D., M. and Goldberg, S. N., "Basic Science Research in Thermal Ablation" Surg. Oncol. Clin. N. Amer. 20: 237-258 (2011).
Allison, K.R, et al., "Pulsed dye laser treatment of superficial basal cell carcinoma: realistic or not?," Lasers Med. Sci., 18: 125-6 (2003).
Arens, R., et al., "Linear dimensions of the upper airway structure during development," Am. J. Respir. Crit. Care Med., 165: 117-122 (2002).
Anrade, J.L.F., et al., "The effect of adenotonsillectomy on oxygen saturation in children with sleep-disordered breathing," J. Bras. Pneumol., 33: 62-68 (2007).
Au, J. L-S., et al., "Clinical Aspects of Drug Delivery to Tumors," J. Control Rel., 78: 81-95 (2002).
Beutner, K.R., et al., "Effect of Pulsed Dye Laser on Basal Cell Carcinoma," Lasers Surg. Med. Suppl., 14: 22 (2002).
Bhattacharyya, N., "Evaluation of post-tonsillectomy bleeding in the adult population," ENT—Ear, Nose & Throat Journal, 80: 544-549 (2001).
Botteman, M.F., et al., "The Health Economics of Bladder Cancer," Pharmacoeconomics, 21(18): 1315-1330 (2003).
Brodsky, L., et al., "Naso- and oropharyngeal dimensions in children with obstructive sleep apnea," Int. J. Pediatr. Otorhinolaryngol., 17: 1-11 (1989).
Campolmi, P., et al., "Vascular based non conventional dye laser treatment for basal cell carcinoma," Dermatol. Ther., 21: 402-405 (2008).
Chang, K.W., "Intracapsular versus subcapsular coblation tonsillectomy," Otolaryngol. Head Neck Surg., 138: 153-157 (2008).
Chen, D., et al., "Effect of Dimethyl Sulfoxide on Bladder Tissue Penetration of Intravesical Paclitaxel," Clin. Cancer Res., 9: 363-369 (2003).
Chole, R.A., et al., "Anatomical evidence of microbial biofilms in tonsillar tissues," Arch. Otolaryngol. Head Neck Surg., 129: 634-636 (2003).
Christenson, L.J., et al., "Incidence of Basal Cell and Squamous Cell Carcinomas in a Population Younger Than 40 Years," JAMA, 294: 681-690 (2005).
Colen, T.Y., et al., "Effect of intracapsular tonsillectomy on quality of life for children with obstructive sleep-disordered breathing," Arch. Otolaryngol. Head Neck Surg., 134: 124-127 (2008).
Corry, P.M. and Dewhirst, M.W., "Thermal Medicine, Heat Shock Proteins and Cancer," Int. J. Hyperthermia, 21(8): 575-677 (2005).
DeNardo, S.J., et al., "Thermal Dosimetry Predictive of Efficacy of 111In-ChL6 Nanoparticle AMF—Induced Thermoablative Therapy for Human Breast Cancer in Mice," J. Nuc. Med., 48:437-444 (2007).
Derkay, C.S., et al., "Post-tonsillectomy morbidity and quality of life in pediatric patients with obstructive tonsils and adenoid: microdebrider vs electrocautery," Otolaryngol. Head Neck Surg., 134: 114-120 (2006).

Dickerson, E.B., et al., "Gold Nanorod Assisted Near-Infrared Plasmonic Photothermal Therapy (PPTT) of Squamous cell Carcinoma in Mice," Cancer Letter, 269(1):57-66 (2008).
Dickson, J.A., and Calderwood, S.K., "Temperature Range and Selective Sensitivity of Tumors to Hyperthermia: A critical Review," Cancer Research Unit, University Department of Biochemistry, pp. 180-205 (1980).
Elbialy N. et al., "Low Power Argon Laser-Induced Thermal Therapy for Subcutaneous Ehrlich Carcinoma in Mice Using Spherical Gold Nanoparticles," J. of Biomedical Nanotechnology, 6:1-7 (2010).
El-Sayed I. H. et al., "Selective Laser Photo-thermal Therapy of Epithelial Carcinoma Using Anti-EGFR Antibody Conjugated Gold Nanoparticles," Cancer Letters, 239: 129-135 (2006).
Feng, Y., et al., "Optimization and Real-Time Control for Laser Treatment of Heterogeneous Soft Tissues," Comput. Methods Appl. Mech. Eng., 198(21): 1742-1750 (2009).
Foley, P., et al., "Photodynamic therapy with methyl aminolevulinate for primary nodular basal cell carcinoma: results of two randomized studies," Int. J. Dermatol., 48: 1236-1245 (2009).
Galland, B.C., et al., "Changes in behavior and attentional capacity after tonsillectomy," Pediatr. Res., 59: 711-716 (2006).
Ghosh, S., et al., "Increased Heating Efficiency and Selective Thermal Ablation of Malignant Tissue with DNA-Encased Vlultiwalled Carbon Nanotubes," American Chemical Society, 3(9): 2667-2673 (2009).
Hallock, G.G. and Lutz, D.A., "A Prospective Study of the Accuracy of the Surgeon's Diagnosis and Significance of Positive Margins in Nonmelanoma Skin Cancers," Plast. Reconstr. Surg., 107: 942-947 (2001).
He, X., et al., "Thermal Therapy in Urologic Systems: A Comparison of Arrhenius and Thermal Isoeffective Dose Models in Predicting Hyperthermic Injury," Journal of Biomechanical Engineering, 131: 1-12 (2009).
International Preliminary Report on Patentability, PCT/US2011/055397, dated Apr. 18, 2013.
International Search Report and Written Opinion, PCT/US2011/055397, dated May 29, 2013.
Isaacson, G., et al., "Developmental anatomy of the tonsil and its implications for intra-capsular tonsillectomy," Int. J. Pediatr. Otorhinolaryngol., doi:0.1016/j.ijpor1.2007.09.021 (2007).
Jemal, A., et al., "Cancer Statistics, 2008," CA Cancer J. Clin., 58: 71-96 (2008).
Karim, M.A., et al., "Realization of a uniform circular source using a two-dimensional binary filter," Optics Letters, vol. 10, No. 10 (Oct. 1985).
Koechner, W. Solid-State Laser Engineering, 2nd Ed., Springer-Verlag, pp. 251-253 (1988).
Kretsos, K. and Kasting, G.B., "Dermal Capillary Clearance: Physiology and Modeling," Skin Pharmacol. Physiol., 18: 55-74 (2005).
Lee, S-J., et al., "Bioadhesive Drug Delivery System Using Glyceryl Monooleate for the Intravesical Administration of Paclitaxel," Chemotherapy, 51: 311-318 (2005).
Love, W.E., et al., "Topical Imiquimod or Fluorouracil Therapy for Basal and Squamous Cell Carcinoma," Arch. Dermatol., 145: 1431-1438 (2009).
Lu, Z., et al., "Paclitaxel-Loaded Gelatin Nanoparticles for Intravesical Bladder Cancer Therapy," Clin. Cancer Res., 10: 7677-7684 (2004).
Magdy, E.A., et al., "Coblation tonsillectomy: a prospective, double-blind, randomized, clinical and Histopathological comparison with dissection-ligation, monopolar electrocautery and laser tonsillectomies," J. Laryngol. Otol., 122: 282-290 (2008).
Michel, R.G., et al., "Safety and efficacy of pressure-assisted tissue-welding tonsillectomy: a preliminary evaluation," ENT—Ear, Nose & Throat Journal, 87: 100-112 (2008).
Mooney, R., et al., "Neural Stem Cell-Mediated Intratumoral Delivery of Gold Nanorods Improves Photothermal Therapy," American Chemical Society, 8(12): 12450-12460 (2014).
Dkuyucu, S., et al., "The effect of anesthetic agents on perioperative bleeding during tonsillectomy: propofol-based iersus desflurane-based anesthesia," Otolaryngol. Head Neck Surg., 138: 158-161 (2008).

(56) References Cited

OTHER PUBLICATIONS

Overholt, B., et al., "Photodynamic Therapy for Esophageal Cancer Using a 180° C. Windowed Esophageal Balloon," Lasers in Surgery and Medicine 14:27-33 (1994).

Ozdemir, I., et al., "Measurement of tonsillar blood flow in normal and pathological conditions by the use of the 133Xe clearance technique," Arch. Otorhinolaryngol., 242: 53-56 (1985).

Robinson, J.K. and Fisher, S.G., "Recurrent Basal Cell Carcinoma After Incomplete Resection," Arch. Dermatol., 136: 1318-1324 (2000).

Roth, J.A., et al., "Harmonic scalpel tonsillectomy versus monopolar diathermy tonsillectomy: a prospective study," ENT—Ear, Nose & Throat J., 87: 346-349 (2008).

Salonen, A., et al., "Recovery after tonsillectomy in adults: a three-week followup study," Laryngoscope, 112: 94-98 (2002).

Shah, R.K., et al., "Optical-thermal simulation of tonsillar tissue irradiation," Lasers Surg. Med., 28: 313-319 (2001).

Shah, S.M., et al., "The Effect of 595 nm Pulsed Dye Laser on Superficial and Nodular Basal Cell Carcinomas," Lasers Surg. Med., 41: 417-422 (2009).

Sherar, M.D., et al., "Interstitial Microwave Thermal Therapy and its Application to the Treatment of Recurrent Prostate Cancer," Int. J. Hyperthermia, 20(7): 757-768 (2004).

\* cited by examiner

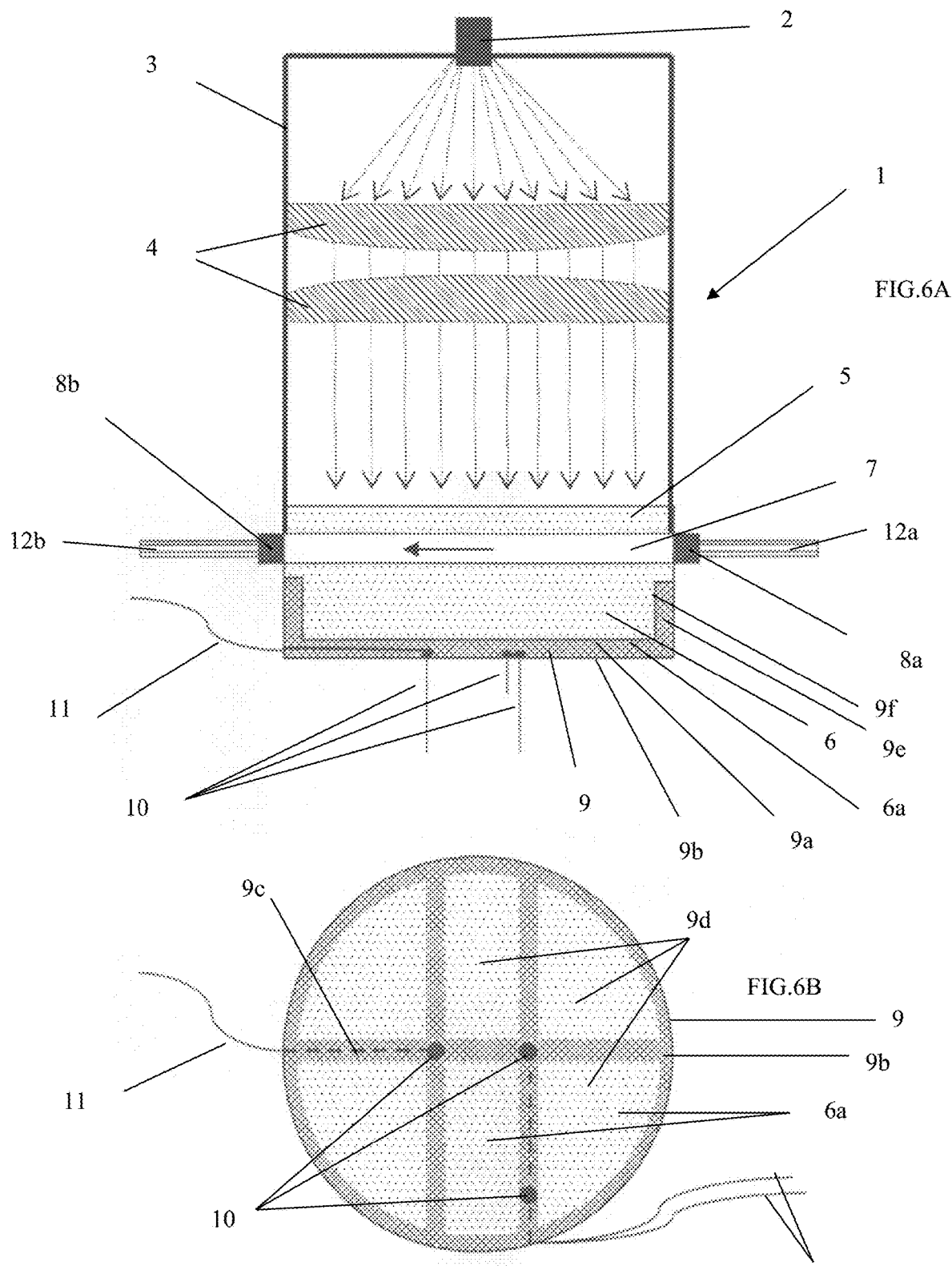

▶ substrate features: diameter 200 to 500 μm, depth 15 or 100 μm

METHOD FOR SKIN CANCER THERMAL THERAPY

RELATED APPLICATION

This application is divisional of U.S. application Ser. No. 13/878,185, filed Oct. 7, 2011, which is the U.S. National Stage of International Application No. PCT/US2011/055397, filed Oct. 7, 2011, which designates the U.S., published in English, and claims the benefit of U.S. Provisional Application No. 61/390,838, filed on Oct. 7, 2010. The entire teachings of the above applications are incorporated herein by reference.

BACKGROUND OF THE INVENTION

Nonmelanoma skin cancer (NMSC) is more common in the United States than all other types of cancer combined. A recent study of US national databases has shown a 4.2% yearly average increase in the number of NMSC procedures in the Medicare population from 1992 to 2006, and a total of 3.5 million NMSC procedures performed in 2.2 million Medicare and non-Medicare patients in 2006 (Rogers H W et al. Arch Dermatol 146(3); 283, 2010). Assuming an unchanged rate of increase, five million NMSC procedures per year will be performed by 2015 in the US. NMSC most commonly occurs in people over the age of 50 years, however studies in the US and Europe have shown a disproportionate increased incidence in women under 40 (Christenson L J et al. JAMA 294; 681, 2005, Birch-Johansen et al. Int J Cancer Apr. 19, 2010), raising concerns of an even higher number of patients in future, and resultant increased morbidity and economic burden.

NMSC includes both squamous cell carcinoma (SCC) and basal cell carcinoma (BCC), and is caused by ultraviolet (UV)-induced mutations in epidermal cells. Seventy-five to eighty percent of new cases of NMSC each year are BCC (Tierney E P, Hanke C W. J Drugs Dermatol 8; 914-922, 2009). A recent study has shown that BCC arise from keratinocytes of the interfollicular epidermis (Youssef K K et al. Nat Cell Biol 12; 299-305, 2010). BCC appear as different histologic subtypes, including nodular (45.9% of all BCC), superficial (25.9%), infiltrative (16.0%), and micronodular (9.1%), as well as other and mixed subtypes (Raasch B A et al. Br J Dermatol 155; 401-7, 2006). Infiltrative and micronodular BCC are classified as "high risk" tumors, as are nodular tumors of the midface or ear, and large or recurrent tumors. Risk in the context of BCC refers to aggressiveness or likelihood of spread or recurrence after treatment, rather than mortality. BCC of any type or location has a very low probability of metastasis; however it is locally destructive, and if left untreated or treated incompletely may become deeply and/or widely invasive of surrounding skin and subcutaneous tissue. With the exception of superficial BCC (sBCC), which are most common on the trunk or extremities, the majority of BCC occur on the face. BCC and other NMSC have their highest incidence in people of European ethnicity, but also occur in Asian populations, and with increasing incidence (Kim H S et al. J Korean Med Sci 25; 924-9, 2010).

The first goal in treatment of BCC, as in any cancer treatment, is the complete eradication of tumor cells; the second objective is sparing surrounding normal tissue required for good cosmesis and function. Surgery and destructive methods such as cryosurgery, and electrodessication and curettage (EDC), are the mainstays for treatment of NMSC, and with those methods complete tumor cell eradication necessitates damage to normal tissue.

Of all BCC surgeries, Mohs micrographic surgery is the most tissue-sparing. It is also the most reliably effective in removing all malignant cells associated with the lesion, and has a 5 year recurrence rate of only 1% for primary tumors (Muller F M et al. Dermatol Surg 35; 1349-1354, 2009). The cost of Mohs surgery depends on the number of stages or levels that are subjected to histological analysis for mapping of the tumor and the complexity of the repair needed for the resulting skin defect. Average costs of Mohs surgery for treatment of BCC on the cheek are $1263 (Rogers H W, Coldiron B M. J Am Acad Dermatol 61; 96-103, 2009). Larger, deeper lesions or lesions in difficult anatomic locations can cost substantially more. The surgical wound can be extensive and often requires reconstruction using flaps or full thickness skin grafts. The number of physicians receiving formal training in Mohs surgery has increased substantially in the past decade, and 25% of all dermatologists now perform this procedure (Tierney E P et al. Derm Surg 35; 413-9, 2009).

Traditional surgical excision with immediate or delayed repair of the surgical defect is another standard treatment of BCC. Typically, a 4 mm margin of normal-appearing skin is excised with the tumor. A comparison of surgical excision with Mohs has shown that excision leaves a 60% larger surgical defect (Muller F M, et al. Dermatol Surg 35; 1349-1354, 2009). Remarkably, retrospective analysis has shown that 14% of BCC are incompletely excised (Malik V, et al. J Plast Reconstr Surg Aesth Surg, 2010). Because of the difficulty in determining the subsurface spread and depth of the tumor and the competing need to preserve healthy, uninvolved skin tissue, surgical excision has higher recurrence rates than Mohs surgery. The 5 year recurrence rate for primary BCC following surgical excision is approximately 5% (Thissen M R et al. Arch Dermatol 135; 177-183, 1999). Excision of a BCC on the cheek with permanent margins and immediate or delayed repair is estimated to cost on average $1006 and $1170, respectively (Rogers H W, Coldiron B M. J Am Acad Dermatol 61; 96-103, 2009).

The least costly methods of treating BCC are cryosurgery and EDC. Cryosurgery is commonly used to treat superficial BCC on the trunk or extremities. Because it is nonselectively destructive, significant scarring, skin texture changes, and hypopigmentation commonly result. As with EDC there is no opportunity to examine the margins of normal-appearing skin left behind after surgery, and so it is not a preferred treatment for BCC of aggressive subtypes or on locations associated with high risk of recurrence. The estimated average cost of EDC for BCC on the cheek and arm is $471 and $392, respectively. Five year recurrence rates for cryosurgery and EDC are 7.5 and 7.7%, respectively (Tierney E P, Hanke C W. J Drugs Dermatol 8; 914-922, 2009). Recurrences after cryosurgery or EDC are typically treated with Mohs surgery.

Although excision, Mohs, EDC and cryosurgery are effective in treating NMSC, there has been a long-standing interest in alternatives that would provide better cosmetic and functional results, and allow the patient to avoid invasive and destructive surgery. As early as the 1960's, a number of chemotherapeutic and immunotherapeutic drugs were tested (Williams A C, Klein E. Cancer 25; 450-462, 1970). Topically applied chemotherapeutic drugs produced inconsistent results on BCC, with side effects including blistering, crusting, and dermatitis. Consequently, topical chemotherapeutic drugs were largely abandoned as treatment alternatives. The exception has been 5-fluorouracil (SFU, Efudex Valeant Pharmaceuticals International, Aliso Viejo, Calif.) which has become a widely-used, standard treatment for actinic keratoses (AKs, epidermal precursor lesions for SCC) and is approved by FDA for treatment of sBCC when conventional treatments are impractical. Histologic cure rates of 90% have been reported for sBCC treated over a period of up to 12 weeks with 5FU (Gross K et al. Derm Surg 33; 433-9, 2007). 5FU treatment of BCC other than the superficial type may result in apparent clinical cure with tumor persisting in the deeper dermis, potentially resulting in recurrence with subclinical spread (Lee S et al. Drugs 67; 915-934, 2007).

The early immune response modifiers tested showed efficacy for superficial skin tumors, and a newer drug imiquimod (Aldara®, Graceway Pharmaceuticals, Bristol, Tenn.) was introduced in the past decade (Love W E, et al. Arch Dermatol 145; 1431-1438. 2009). Therapy involves application five times a week for six weeks. Imiquimod is currently approved by FDA only for treatment of superficial BCC less than 2 cm in diameter and only on the trunk, neck, or extremities. When imiquimod has been used to treat nodular or micronodular BCC, it has been found that clearance of the tumor in the upper layers of the skin can mask residual deeper involvement and growth, which may be the result of poor exposure of the deeper tumor to the topical drug (Sukai S A, et al. Derm Surg 35; 1831, 2009).

Both imiquimod and 5FU therapies require patient adherence to lengthy treatment regimes, and both have frequent adverse effects. Based on a review of published data, it has been recommended that use of imiquimod and 5FU be limited to patients with small superficial BCC in low risk anatomic locations when more effective surgical or destructive procedures cannot be used (Love W E et al. Arch Dermatol 145; 1431-8, 2009).

Treatment of NMSC including BCC with lesional and perilesional interferon injections avoids the problem of limited depth of drug penetration implicated in 5FU and imiquimod failures when treating non-superficial tumors. However, the injected interferon has a high incidence of systemic adverse effects and administration may require many office visits over a period of several weeks. Intralesional injections of interferons or other agents are rarely used to treat NMSC.

Photodynamic therapy (PDT), which involves activation of a photosensitizing drug with light, has been studied for many years for treatment of BCC. Effective PDT requires that both drug and light fully penetrate the tumor. PDT using the topically-applied photosensitizer aminolevulinic acid or its derivatives is approved for treatment of sBCC. A recent multi-site study reported short term results in the more common nodular BCC; patients received two to four PDT sessions preceded by debridement and debulking of the tumor to facilitate penetration of the drug. Histologically verified complete response was 73% versus 27% for a placebo control group at 6 months. (Foley P, et al. Int J Dermatol 48; 1236, 2009). Pain is a significant side effect of PDT for skin cancer.

All of the above mentioned nonsurgical alternative treatments for NMSC that involve topical agents applied to the skin surface—chemotherapeutic, immunotherapeutic or photodynamic drugs—have as a major limitation the inability to reliably treat BCC other than superficial type, which comprise only about 20% of all BCC. Other drawbacks are multiple treatment visits and prolonged treatment regimes. Although the cosmetic and functional outcomes of these alternative therapies are frequently superior to those of surgical or destructive procedures, the advantage of a traditional surgical procedure that reliably removes or destroys the tumor in a single office visit is sufficient that the alternatives currently have a minor role in treatment of BCC and other NMSC.

The potential use of laser radiation to eradicate skin cancer has been of long-standing interest, with first reports appearing only a few years after the laser was invented. Near infrared (NIR) and infrared (IR) laser treatment of NMSC is based on absorption of radiation by water, the main component of soft tissue including skin and tumor tissue. The $CO_2$ laser operates at an IR wavelength (1.06 $\mu$m) that is very strongly absorbed by water, and therefore has limited depth of penetration in soft tissue. The $CO_2$ laser in pulsed or repetitively scanned mode can be used to vaporize superficial skin tumors layer by layer. Larger, deeper, and infiltrative tumors are not effectively eradicated and there is little advantage in treatment of even superficial lesions with this alternative destructive technique (Prstojevich S J and Nierzwicki B J, Oral Maxillofacial Surg Clin N Am 17; 147, 2005). The $CO_2$ laser is not recommended for routine treatment of skin cancer (Hruza G J, Dermatol Clin 20; 147, 2002).

NIR Nd:YAG lasers operating at 1064 nm penetrate much deeper in soft tissue due to the weaker absorption by water at this wavelength, and have been used to coagulate rather than vaporize skin tumors. Nd:YAG laser treatment of NMSC results in delayed wound healing, scarring, and unacceptably high recurrence rates (Landthaler M, et al. Recent Res Cancer Res 130; 417, 1995). Burn-like scars are reported to be inevitable following treatment of BCC or other skin cancers with the 1064 nm Nd:YAG laser (Karrer S, et al., Am J Clin Dermatol 2; 229, 2001). When using the Nd:YAG laser both the tumor and the surrounding normal skin absorb the NIR radiation and are heated, and both of these components are typically coagulated with the objective of eradicating all tumor cells. This thermal laser technique is "blind" as there is no means of intraoperatively or postoperatively assessing tumor cell eradication, other than by tumor recurrence. Recently, Russian researchers described the use of a high power pulsed Nd:YAG laser for treatment of a large series of patients with NMSC; treatment parameters were described as causing total destruction of the tumor and coagulative necrosis of adjacent normal tissue, healing with crusting and reepithelialization, with the end result of a smooth scar at the treatment site (Moskalik K et al., Photomed Laser Surg 27; 345, 2009). A smaller study reported using a continuous wave Nd:YAG laser in up to 4 treatment sessions in 37 patients (El-Tonsy MI-1 et al., Dermatology Online Journal 10(2); 3, 2004). Treatments involved using a thermocouple on the skin surface away from direct exposure to the laser beam to monitor surface temperature, and irradiating the tumor site with the laser to maintain a temperature of 45° C. for 1 minute. Superficial erosion and crusting were seen as normal consequences of the treatment, which resulted in permanent scarring in 11% of patients, and 3% recurrence at 3-5 years followup. Other limitations of the El-Tonsy method include the unknown temperature at the actual locations of tumor cells below the skin surface, and the lack of any means of correlating treatment time and temperature (surface or at depth) with damage to tumor cells or surrounding normal skin. Other researchers with experience with the Nd:YAG laser do not recommend its routine use for treatment of NMSC (Raulin C, Karsai S, Schmitt L, in Laser and IPL Technology in Dermatology and Aesthetic Medicine, pp 165-175, Springer, 2011).

Thus, at present, although ablative IR and thermal NIR lasers have been in the surgical armamentarium of dermatologists for many decades, they have not been successfully adapted for standard treatment of BCC and other NMSC.

Visible wavelength vascular targeting lasers have been a recent subject of evaluation for NMSC treatment (Raulin C, Karsai S, Schmitt L, in Laser and IPL Technology in Dermatology and Aesthetic Medicine, pp 165-175, Springer, 2011).

The present inventor first reported the use of the 585 nm pulsed dye laser (PDL) for BCC treatment (Beutner K R, Geisse J K, Alexander J, McMillan K Lasers Surg Med Suppl 14; 22, 2002). The PDL was evaluated as a means of treating BCC by selective eradication of the blood supply on which the tumor cells depended. This study was followed by others (Allison K P, Kiernan M N, Waters R A, Clement R M, Lasers Med Sci 18; 125-6, 2003, Campolini P, Troiano M, Bonan P, Cannarozzo G, Lotti T. Dermatol Ther 21; 402-405, 2008, Shah S M, Konnikov N, Duncan L M, Tannous Z S, Lasers Surg Med 41; 417-422, 2009). These studies demonstrated the ability of PDL treatment to eradicate some BCC of different histologic types, and cosmetic results are excellent compared to the standard nonselectively destructive treatments. Several treatment sessions are typically required for successful eradication, and not all lesions respond completely. Recently Ibrahimi et al. reported the use of a 755 nm flashlamp-pumped alexandrite laser to treat basal cell carcinoma in Gorlin's syndrome. Laser-induced microvascular injury was seen at depths to the subcutaneous tissue however treatment led to hypopigmentation and scarring (Ibrahimi OA, et al. Lasers Surg Med 43; 68, 2011). A fundamental difficulty with the photothermal vascular targeting approach, using any wavelength or combination of wavelengths preferentially absorbed by blood, is that only a portion of vessels in the irradiated volume are coagulated at fluences below the threshold for damage to nonvascular structures and scar formation; therefore, tumor eradication requires multiple treatments even in smaller or superficial tumors. To address this problem, the present inventor has described an apparatus and method for using vascular targeting lasers to treat NMSC by a combined process of targeting tumor vasculature and increasing the exposure of tumor cells to topical anticancer drugs by modification of skin permeability (McMillan K, WO/2010/102099A1). Deeper, thicker and more extensive tumors are challenging due to difficulties in selective targeting of microvasculature at depth in the dermis using vascular lasers. At present, vascular-targeting lasers including PDL and alexandrite are not yet routine alternatives to surgical excision for treatment of NMSC.

For a nonsurgical treatment for NMSC to become a routine and advantageous alternative for treatment of commonly presenting tumors and not only sBBC, it should have sufficient efficacy in eradicating tumor cells at depth within the tissue that histological examination of treatment margins (as in surgical excision or Mohs surgery) is unnecessary. This significant challenge is made more difficult by the variety of different histologic subtypes of BCC having different patterns of cellular and vascular growth, and the possibility of subsurface lateral and deep extension beyond the clinically evident portion. Furthermore, skin that is the tumor environment itself varies in thickness: neck, nasal tip, and forehead skin has thickness (combined dermal and epidermal) of 0.5, 1.2, and 1.0 mm, respectively (Ha R Y, et al. Plast Reconstr Surg 115; 1769, 2005), and skin on the back, dorsal aspect of forearm, and lateral aspect of the leg has thickness 2.5, 1.1, and 1.3 mm, respectively (Tan C Y et al. Br J Dermatol 106; 657, 1982). Also, the thickness of subcutaneous adipose tissue and/or fascia underlying the dermis is highly variable with anatomic location and between patients.

At present, with the number of BCC and other NMSC requiring treatment very high and increasing, there is a pressing need for a new treatment that (1) is highly effective, (2) provides excellent cosmetic results, (3) can be rapidly and easily performed by the physician, (4) is less costly than surgical excision or Mohs surgery, and (5) is not limited to superficial, primary tumors.

SUMMARY OF THE INVENTION

The invention generally is directed to treatment of soft tissue with a source of radiation, resulting in irradiated soft tissue, measuring the temperature in at least one location within the region of soft tissue, and converting the temperature in the at least one location within the region of soft tissue into a measure of damage produced in at least two components of the irradiated soft tissue, the components comprising at least one normal tissue component and at least one malignant, hypertrophic, diseased, or unwanted component.

In one embodiment, an apparatus for treatment of soft tissue includes a source of radiation, a handpiece which is adapted to transmit radiation emitted from the source of radiation to a region of soft tissue, resulting in irradiated soft tissue, said handpiece being positioned adjacent to or in contact with said soft tissue region, a grid element adapted to hold at least one temperature sensor in contact with or embedded in said region of soft tissue, and a microprocessor, which converts a signal from the at least one temperature sensor into a measure of damage produced in at least two components of the irradiated soft tissue, said components comprising at least one normal tissue component and at least one malignant, hypertrophic, diseased, or unwanted component. The at least one normal tissue component can be collagen. The at least one malignant, hypertrophic, diseased, or unwanted component can be tumor cells. In some embodiments, the at least one normal tissue component can be dermal collagen, and the at least one malignant, hypertrophic, diseased, or unwanted component can be skin cancer cells. The source of radiation can be a coherent or incoherent source emitting radiation in a range between about 700 nm and about 1310 nm, such as in a range between about 1100 nm and about 1310 nm, or in a range between about 1100 nm and about 1140 nm. The grid element can be attached to the handpiece. In some embodiments, the grid element can be removably attached to the handpiece. In certain embodiments, the grid element can be disposable. The grid element can be adapted to hold at least two temperature sensors embedded at least two different depths in the irradiated soft tissue. The at least one temperature sensor can be a thermocouple or a thermistor. In some embodiments, the thermocouple or thermistor can be contained within a needle having a proximal end and a distal end, such that the proximal end is affixed to the grid element and the distal end is embedded in the irradiated soft tissue. The measure of thermal damage can be the Arrhenius damage integral. In some embodiments, the handpiece can include a cooling element for cooling the region of soft tissue for at least a portion of the time that the at least one temperature sensor is in contact with or embedded in said soft tissue. In certain embodiments, the apparatus can further include a display unit, whereby the measure of thermal damage produced in at least two components of the irradiated tissue is displayed for at least a portion of the time that the at least one temperature sensor is in contact with or embedded in said soft tissue.

In another embodiment, an apparatus for treatment of soft tissue includes a source of radiation adapted to irradiate a region of soft tissue, a means of measuring temperature in at least one location within said region of soft tissue before, during, and after irradiation, and a means of converting the temperature in the at least one location within said region of soft tissue into a measure of damage produced in at least two components of the irradiated soft tissue, said components comprising at least one normal tissue component and at least one malignant, hypertrophic, diseased, or unwanted component.

In yet another embodiment, an apparatus for treatment of soft tissue includes a source of radiation, a handpiece which is adapted to transmit radiation emitted from the source of radiation to a region of soft tissue, when said handpiece positioned adjacent to or in contact with said soft tissue region, a means of measuring temperature in at least one location within said region of soft tissue, and a means of converting the temperature in the at least one location within said region of soft tissue into a measure of damage produced in at least two components of the irradiated soft tissue, said components comprising at least one normal tissue component and at least one malignant, hypertrophic, diseased, or unwanted component. The handpiece can include a cooling element for cooling the region of soft tissue.

In still another embodiment, a method of heating a biological tissue by application of radiation, the tissue comprising at least one normal component and at least one abnormal, diseased, hypertrophic, malignant, or otherwise unwanted component, includes irradiating a treatment region of the tissue to cause thermal injury to the at least one normal component and the at least one unwanted component, monitoring accumulation of thermal injury during irradiation to the at least one normal component and the at least one unwanted component, and ending irradiation when the at least one unwanted component has been substantially injured by heat. In some embodiments, ending irradiation occurs when (a) the at least one unwanted component has been substantially injured by heat, and (b) the at least one normal component is substantially uninjured by heat. Monitoring the accumulation of thermal injury can include measuring tissue temperature as a function of time before, during, and after irradiation at one or more locations within the tissue. Alternatively, monitoring the accumulation of thermal injury can include simultaneously (a) measuring tissue temperature as a function of time before and during application of radiation, and (b) calculating the tissue cooling rate and time required for the tissue to cool to a temperature at which accumulation of thermal injury substantially ceases, at one or more locations within the tissue. Irradiating the treatment region can include applying radiation at a wavelength within a range of about 1100 nm to about 1310 nm, such as a wavelength within a range of about 1100 nm to about 1140 nm, in a specific embodiment a wavelength of about 1125 nm.

In another embodiment, the method of treating a region of skin includes irradiating the region of skin with a light source adapted to produce preferential injury to blood vessels of a dermal region, and irradiating the region of skin with radiation at a wavelength within a range of about 1100 nm to about 1310 nm. In some embodiments, the method can include waiting for formation of purpura and/or a significant reduction in dermal blood flow after irradiating the region of skin with the light source to produce preferential injury to blood vessels of a dermal region and before irradiating the region of skin with radiation at a wavelength within a range of about 1100 nm to about 1310 nm. Some embodiments can further include applying a topical agent to the skin before irradiating the region of skin with radiation at the wavelength within the range of about 1100 nm to about 1310 nm.

A highly advantageous nonsurgical treatment for NMSC should be able to eradicate malignant cells of superficial tumors in or near the epidermis as well as deeper tumors extending to the reticular dermis or subcutaneous tissue layers, regardless of skin thickness, without causing significant injury to normal skin structures resulting in scarring and poor cosmetic outcomes. Most advantageously, the new treatment is noninvasive or minimally invasive, can be performed in a single session in a physician's office, and is more effective than surgical excision or comparable in efficacy to Mohs surgery.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 6A and 6B are semi-schematic side and end views, respectively, of a handpiece 1 of the invention.

DETAILED DESCRIPTION OF THE INVENTION

A description of example embodiments of the invention follows.

Embodiments of the present invention address, by means of novel technology and novel methodology, the current, long-standing problems and inadequacies of skin cancer treatments. The present invention may be used to treat BCC, SCC, as well as other malignancies, premalignancies, and unwanted structures or lesions of the skin, mucosa, epithelial layers, or other soft tissues elsewhere in the human body. An important aspect of the present invention is the capability of effectively eradicating malignant cells without significant normal tissue destruction, for the most advantageous clinical outcome.

To facilitate understanding of the invention, microscopic photographs of examples of BCC tumors are shown in FIGS. 1 A-D (original photographs from Campbell J B, "Normal Microanatomy: Vertical and Horizontal", and Crowson A N and Garcia C, "Basal Cell Carcinoma: Vertical and Horizontal" in Mohs Surgery and Histopathology: Beyond the Fundamentals, Eds.: K Gross and HK Steinman, Cambridge University Press, 2009, pp 85-108). In FIGS. 1 A-D, stars are used to mark locations of tumor cells within the original photographs.

Figure 1A:
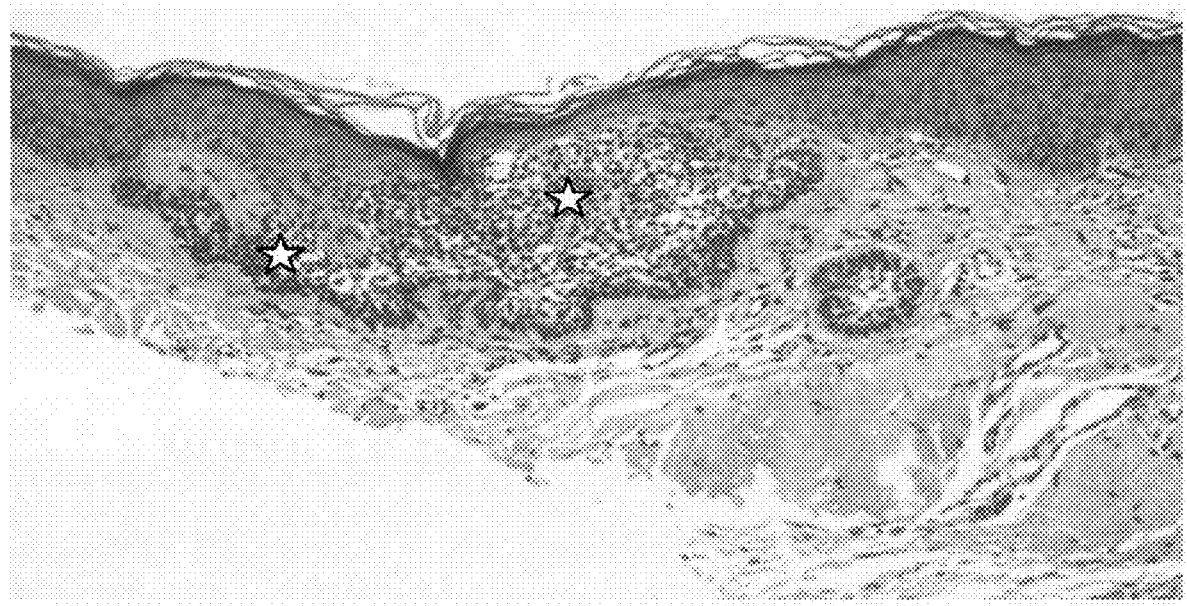
FIGS. 1A-D are microscopic photographs of examples of superficial, nodular, micronodular, and infiltrative BCC tumors.

FIG. 1A is an example of a superficial BCC tumor (sBCC). The tumor cells lie in close proximity to the affected epidermis. An advantageous treatment of sBCC will effectively eradicate tumor cells very close to the skin surface, with minimal damage to surrounding normal, unaffected epidermis that would lead to scarring, or skin texture or pigmentation changes.

Figure 1B:

FIG. 1B is an example of a nodular BCC (nBCC). The lobules of the tumor may extend from the epidermis deep into the dermis. Effective eradication of nBCC requires treatment at depth as well as close to the skin surface. Advantageous treatment of nBCC will produce minimal damage to surrounding normal, unaffected epidermis or dermis, which would lead to scarring, or skin texture or pigmentation changes.

Figure 1C:
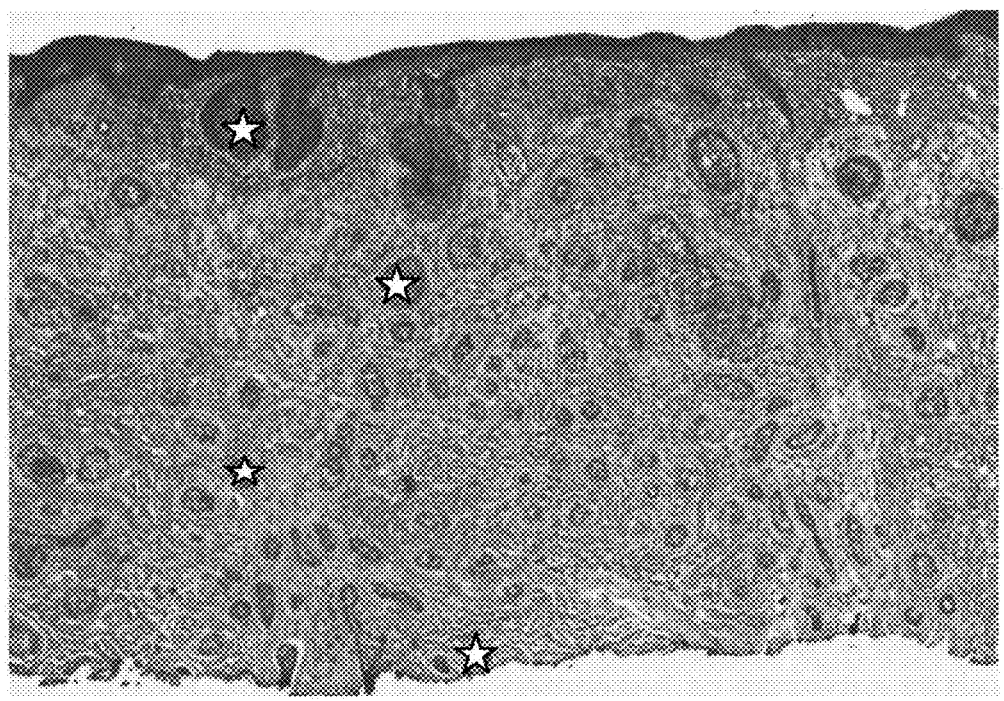

FIG. 1C is an example of a micronodular BCC (mnBCC). In mnBCC, the tumor lobules are smaller and widely dispersed, and may extend deep into the dermis and subcutaneous adipose tissue. Effective eradication of mnBCC requires treatment at depth as well as close to the skin surface, and over an extensive volume where micronodules may reside within skin.

Figure 1D:
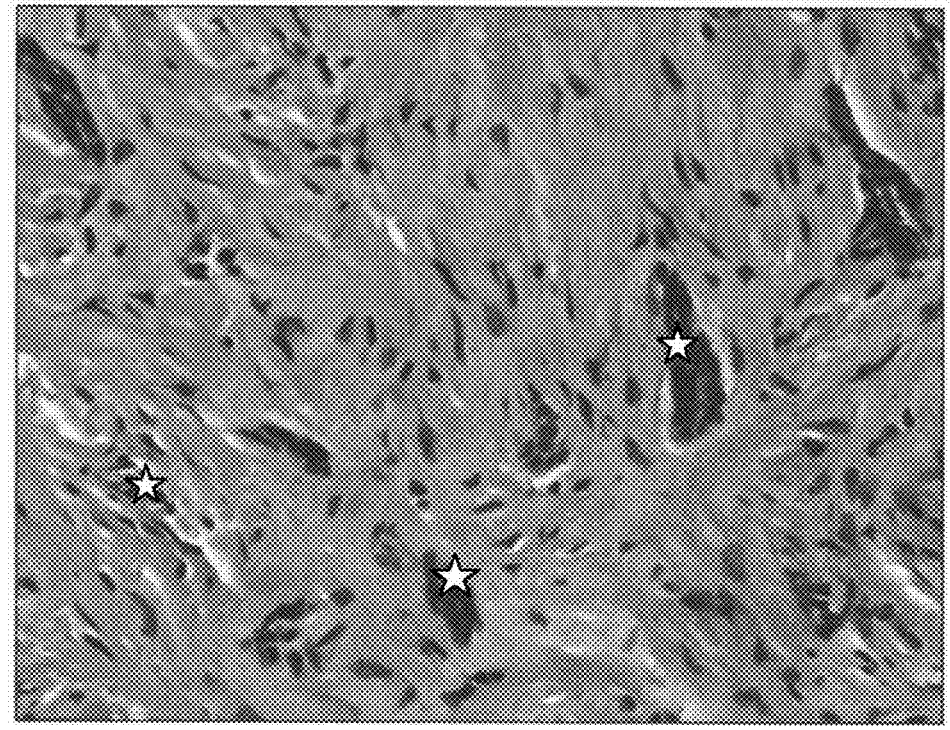

FIG. 1D is an example of an infiltrative BCC (iBCC). iBCC comprise small tumor cords extending deeply into the reticular dermis and subcutaneous tissue. Effective eradication of iBCC requires treatment at depth as well as close to the skin surface, over an extensive volume where tumor cords may reside within skin, and complete killing of cells of this aggressive subtype of BCC. As with all other tumor subtypes, advantageous treatment of iBCC will produce minimal damage to surrounding normal, unaffected epidermis or dermis, which would lead to scarring, or skin texture or pigmentation changes.

These BCC subtypes often exist in combination within the same lesion, and other terminology may be used for these and other subtypes. However, for the purpose of illustrating aspects of the problem of treating BCC, the subtypes shown in FIGS. 1A-D are useful.

In addition to the variations in the different histologic subtypes, BCC may also vary in vascularity, with some tumors having a higher density of blood vessels than others, either within the tumor itself or at the tumor periphery. Significant variability exists in the depth and width of extent of BCC in the skin, depending on subtype, aggressiveness, anatomic location, and duration of growth. It is often difficult or impossible to determine the true extent of a BCC from the appearance of the lesion on the skin surface, or from a superficial biopsy.

As may be appreciated, an advantageous method of treating BCC requires a substantially selective effect on the malignant cells throughout the skin, with sufficient sparing of surrounding normal tissue that the procedure results in preservation of good form and function of the skin tissue.

A finding of the present invention is that tumor cells can be irreversibly injured or killed by heating conditions that will produce less damage to the most relevant component of the skin tissue that contains said tumor cells. Herein, heating conditions are described by temperature as a function of spatial location within the tissue volume and as a function of time before, during, and after treatment. Temperature as a function of time and spatial location will be referred to herein as the "thermal history" at that location. In advantageous embodiments of the invention, a skin cancer is subjected over its entirety to a thermal history that produces an injury to the malignant cells that is at or above the threshold of injury, with concomitant production of an injury to the normal skin components surrounding or interspersed with said malignant cells that is below the threshold of injury. In advantageous embodiments of the invention, the tumor cells will be substantially and irreversibly injured, and the surrounding normal skin tissue will not be so injured as to produce cosmetically or functionally significant scarring.

Rather than comparing the tumor cell thermal injury threshold to normal skin tissue cell thermal injury threshold, in the finding described herein, tumor cell thermal injury threshold is compared to the threshold for thermal injury to collagen fibers. Whereas most normal tissues of the body are made up of living cells in close adherence to one another, dermis and other subepithelial tissue is composed mainly of structural protein fibers, specifically collagen, with living cells being a minor component. According to the present invention, a comparison of tumor cell injury threshold to normal skin cell injury threshold is less important than a comparison of tumor cell injury threshold to the threshold for collagen denaturation.

A comparison between the thermal injury thresholds for collagen and for tumor cells has not previously been made, although in the finding of the present invention it is fundamental to the development of an advantageous thermal therapy for treatment of skin cancer. According to the present invention, the threshold for significant injury to normal skin components in the vicinity of malignant cells in a skin tumor is related to the Arrhenius rate parameters for thermal injury to collagen. Collagen is an extracellular matrix protein that makes up about 80% of the dry weight of the dermis, and takes the form of coiled fibers that give form, elasticity and resilience to the skin. Under sufficiently aggressive heating conditions, the intermolecular hydrogen bonds that give the collagen its three dimensional structure are broken, and the fibers will contract in a process referred to as denaturation. Some denatured collagen in the dermis can be removed as part of the process of healing after thermal injury, but if the collagen denaturation is sufficiently complete the result is coagulative necrosis, wherein the healing process cannot lead to resorption of the volume of damaged collagen. The result of excessive thermal injury to the dermis may be a hard, shrunken mass of denatured collagen that the body is unable to absorb, that is a scar, and which has a disadvantageous cosmetic and/or functional result.

Using the Arrhenius rate model, thermal injury can be calculated using the following equation:

$$\Omega(\delta) = \ln[C(0)/C(\delta)] = \int_0^\delta A e^{-E/RT} dt \qquad \text{Eq. 1}$$

where '$\delta$' is the total treatment time, 'C' is the concentration of native (undamaged) tissue, tissue component or cells under study before treatment or at time $\delta$, and 'A' and 'E' are the Arrhenius rate parameters for the tissue component or cells. T is the absolute temperature and R is the universal gas constant. $\Omega$ is a quantification of the amount of thermal injury that occurs during treatment. A value of $\Omega=1.0$ is conventionally defined as the threshold for injury (see for example J. Pearce and S. Thomsen, "Rate Process Analysis of Thermal Damage," in Optical-Thermal Response of Laser-Irradiated Tissue, eds. A. J. Welch and M. J. C. van Gernert, Plenum Press, N Y 1995, p. 568). $\Omega=1.0$ corresponds to $C(\delta)/C(0)=0.368$, or 37% undamaged tissue remaining at the end of treatment.

The approach taken in the discovery described herein is as follows: first, the value of $\Omega$ corresponding to the upper limit of clinically acceptable damage to dermis is found by a study of $\Omega$ for a well-established, existing commercial medical laser for which extensive clinical experience is available. (This approach does not start with the conventional definition of $\Omega=1.0$, rather, the value of $\Omega$ corresponding to the threshold for actual clinically apparent injury, i.e. scarring of the skin or textural or pigmentation changes, is determined on the basis of extensive clinical experience.) Secondly, for a light source of the present invention having a wavelength that is advantageous for treatment of skin cancer, the $\Omega$ value found in the first step is used to identify treatment parameters that can be safely applied to dermis using the new, advantageous wavelength. Thirdly, the response of tumor cells to these treatment parameters at this new laser wavelength is determined. In this way it can be shown that according to the present invention, tumor cells in the skin can be injured and killed using laser parameters that are substantially sparing of normal dermis.

The 1450 nm diode laser with surface cryogen spray cooling (Smoothbeam, Candela Corporation, Wayland Mass.) is well known for treatment of acne, acne scars, wrinkles, and other benign dermatologic conditions, having been in clinical use for approximately 10 years. The Smoothbeam laser produces pulses in the range of 160 to 220 milliseconds divided into four equal micropulses separated with three cooling sprays of 134a cryogen. This laser is routinely used at fluences of 12 to 14 J/cm2 with a 6 mm diameter irradiated spot. A fluence of 16 J/cm2 is the maximum recommended for treatment of acne, acne scars and wrinkles. The interaction of this laser with skin can be modeled using the Monte Carlo method with heat transfer analysis, and optical and thermal properties of the skin known in the art.

Figure 2A:
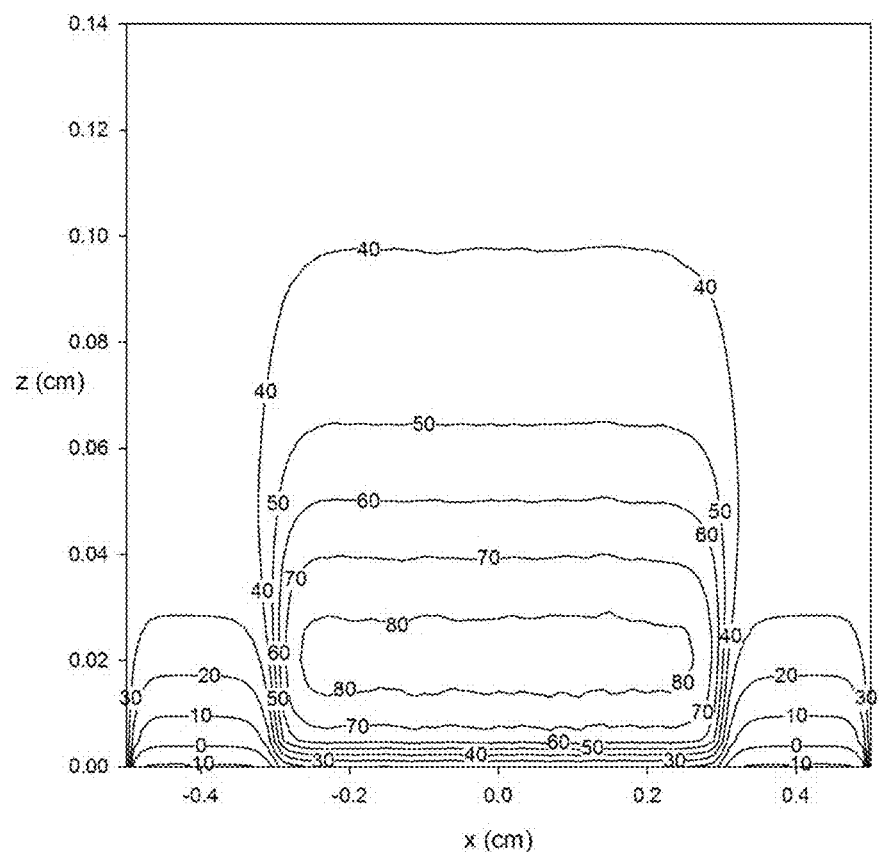
FIGS. 2A-C are contour plots of the temperature within the skin at the end of 14 J/cm2, 16 J/cm2, and 18 J/cm2 pulses from a 1450 nm laser.
Figure 2B:
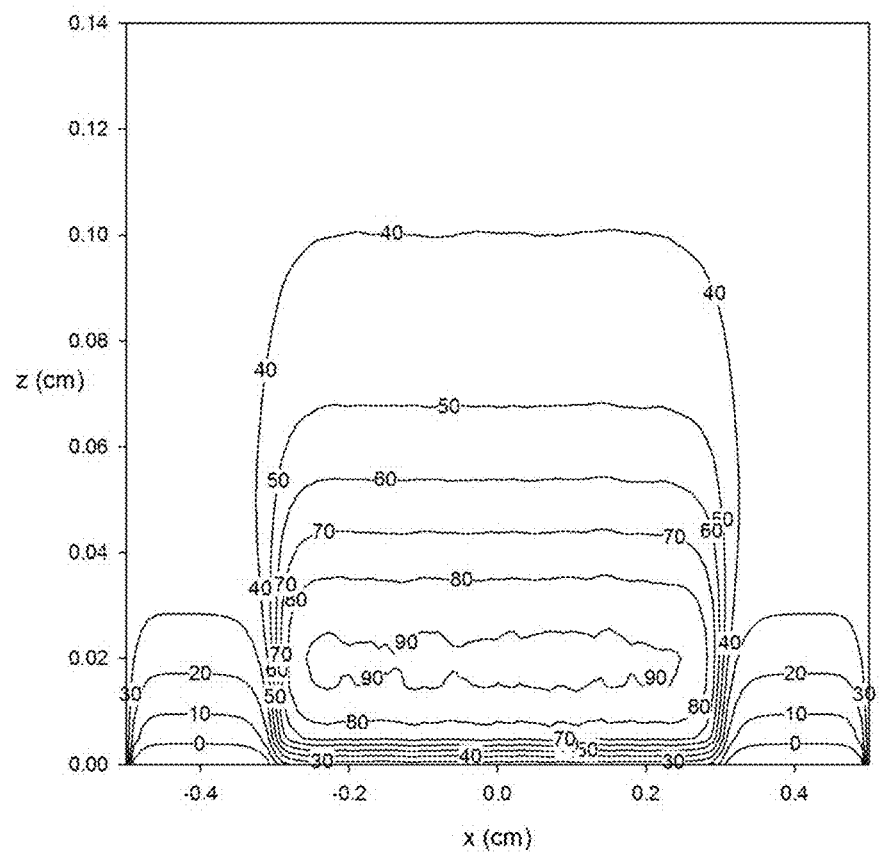
Figure 2C:
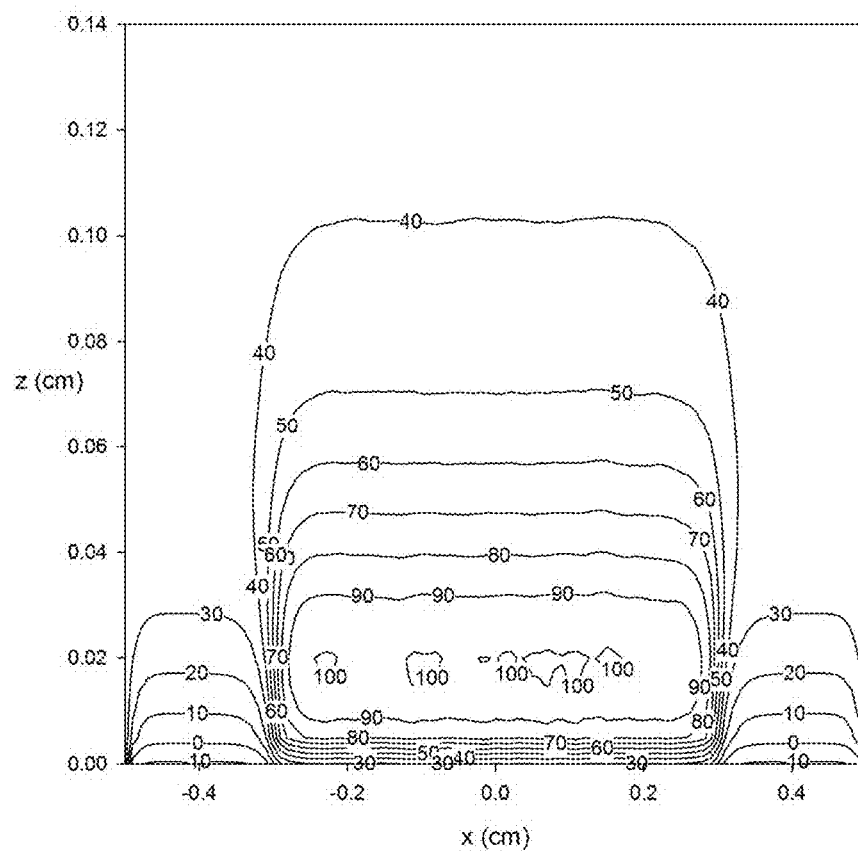

FIGS. 2A-C are contour plots of the temperature within skin at the end of a 14 J/cm2, 16 J/cm2, and 18 J/cm2 pulse respectively. (The latter fluence, 18 J/cm2, is above the recommended dosage and may cause scarring or other untoward effects, based on Smoothbeam clinical laser experience.) In each case the laser spot size on the skin surface is 6 mm, and the cryogen cooling is the same. It can be seen that the region of maximum heating is approximately 150 to 200 microns below the skin surface. The maximum temperature varies by only about 20° C. with the three different laser fluences modeled here. FIGS. 2A-C show the temperature contours at the end of the laser pulse, however the model calculations provide temperature at any point within the skin and at any point in time during and after laser treatment.

According to Eq. 1, the amount of injury depends on both time and temperature (the thermal history), and the Arrhenius parameters A and E specific for the tissue component or cell type under consideration. As noted previously, normal skin tissue thermal injury is characterized herein by the amount of heat-induced collagen denaturation. A and E values for dermal collagen denaturation are well known in the art. Herein, A is taken as 1.606×1045 s−1 and E is 3.06×105 J/mol-1.

Figure 2D:
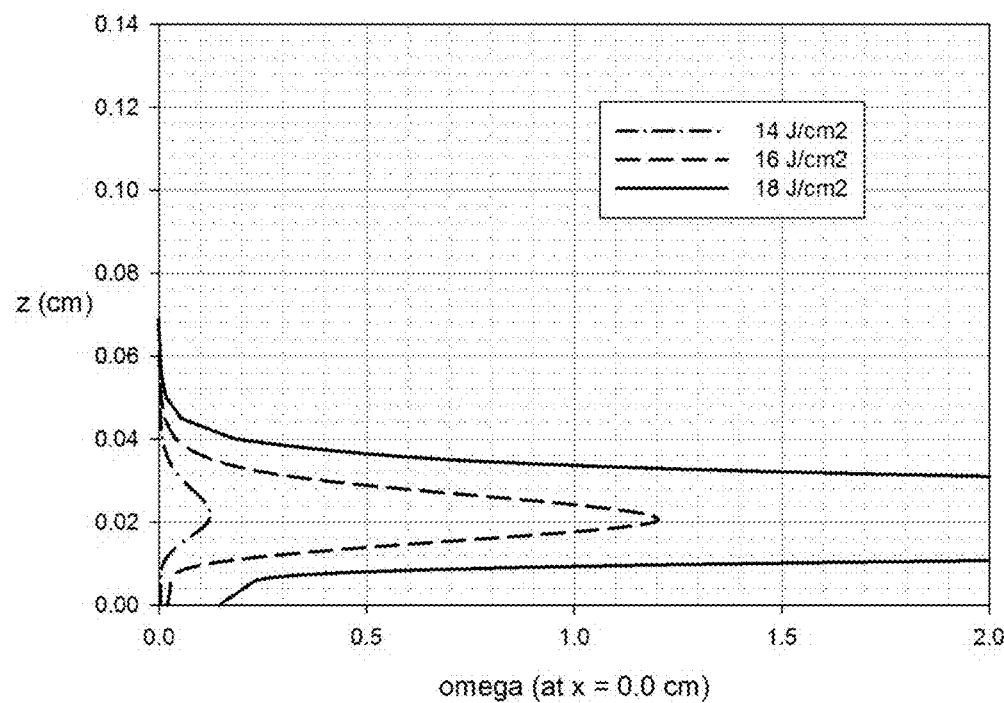
FIG. 2D shows the damage integral $\Omega$ as a function of depth, for the three different fluences.

Using these Arrhenius parameters for collagen denaturation, Eq. 1 and the mathematical model calculations are then combined to find $\Omega$ values after irradiation with the three specific Smoothbeam laser treatment fluences. The model calculations comprise Monte Carlo simulations of photon transport, followed by heat transfer analysis. FIG. 2D shows damage $\Omega$ as a function of depth in the skin tissue, at the center of a 6 mm diameter Smoothbeam laser beam. This calculation shows that the maximum damage $\Omega$ is 0.12 (11% collagen denaturation), 1.2 (70% collagen denaturation), and 11 (100% collagen denaturation), respectively, for 14 J/cm2, 16 J/cm2, and 18 J/cm2 pulses. These calculations indicate that a relatively small difference in laser parameters (e.g. fluence) may produce a large difference in $\Omega$. For the fluence outside the recommended treatment dosage (18 J/cm2), collagen denaturation is substantially complete (100%), consistent with the expectation of clinical side effects. Thus, correlating the model calculations with the known clinical tissue response to the Smoothbeam laser, it is found here that normal skin tissue can tolerate laser-induced thermal histories that produce $\Omega$ values greater than unity, specifically, values of at least 1.2. Therefore, according to the present invention, 1.5 is identified as a reasonable approximate upper limit the value of $\Omega$ corresponding to the amount of collagen denaturation that is consistent with an advantageous clinical outcome and substantial avoidance of scarring. $\Omega=1.5$ corresponds to 78% collagen denaturation by the laser irradiation, or a substantial amount of collagen denaturation but an amount that does not lead to clinically significant coagulative necrosis or scar formation.

Figure 3:
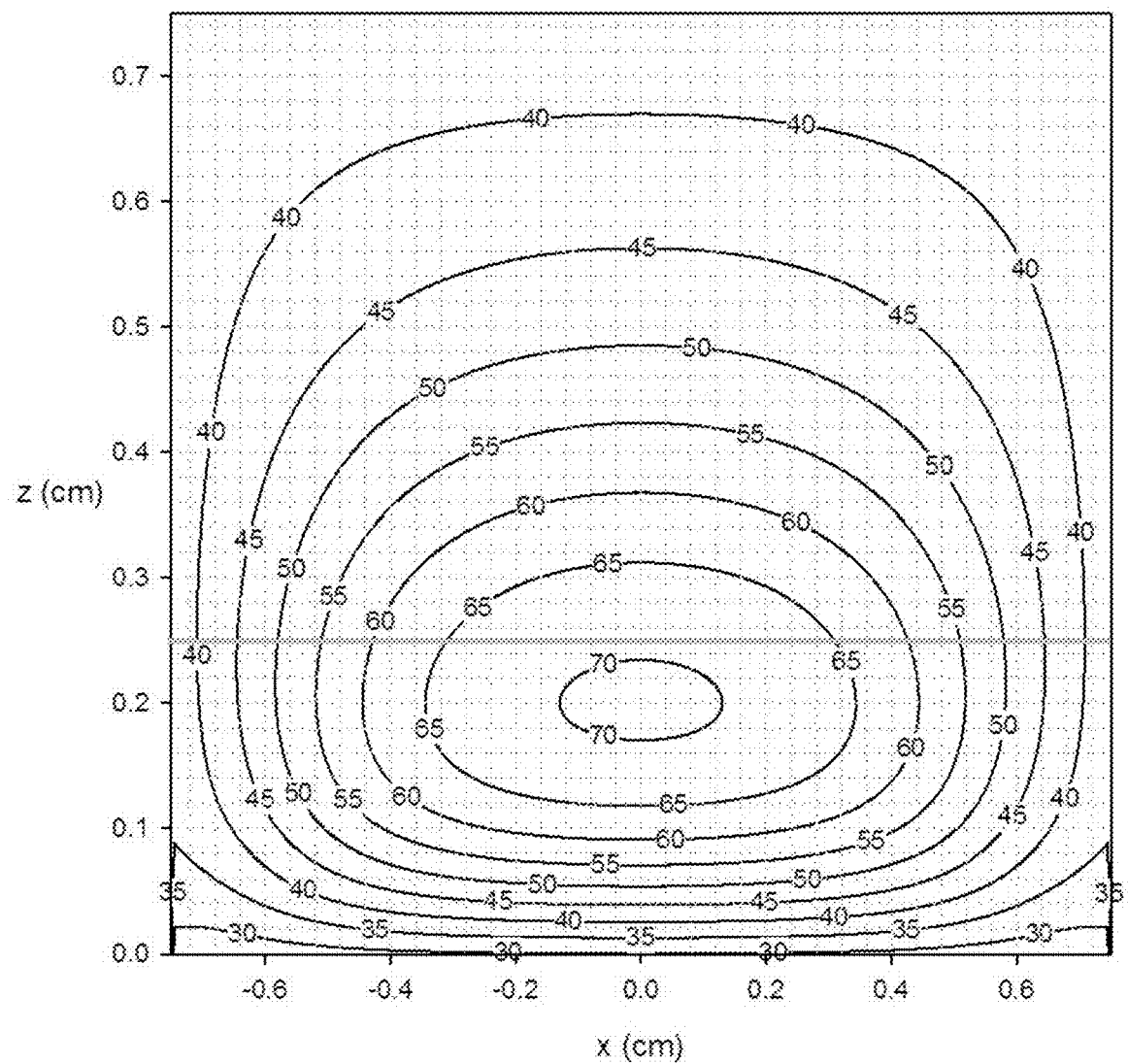
FIG. 3 is a contour plot of temperature within the skin at the end of a 10 W irradiation with an 1125 nm laser.

Next, this finding of clinically acceptable Ω values for collagen denaturation is applied to a different laser wavelength, 1125 nm in the near-infrared. In FIG. 3, the contour plot shows the effect of irradiating skin with 10 W, at 1125 nm, for 28 s, with a 25° C. (room temperature) sapphire window in contact with the skin surface 4s before, during, and 28 s after the pulse, for a total treatment time δ of 1 min. The contour shown in FIG. 3 corresponds to the temperature within the skin at 1 min (that is, at the end of the total treatment time). The model assumes a 12 mm diameter circular irradiated spot on the skin, having flat-top energy distribution. Heating occurs throughout the full thickness of the dermis. The horizontal gray line at 2.5 mm corresponds to the typical thickness of skin on the back, which is typically the thickest type of skin. The rationale for the choice of the 1125 nm wavelength, which is in the range of wavelengths previously identified as most preferred for soft tissue thermal therapy (K. McMillan et al. WO/2010/060097, US20100160904), is described in subsequent sections below. Table I shows the Ω values, as a function of depth in the skin, calculated using Eq. 1 and the Arrhenius parameters for collagen denaturation of skin, for the 10 W laser irradiation of FIG. 3. The maximum Ω value is approximately 1.5, and is located between about 1.5 mm and 2.0 mm deep in the skin, within the lower dermis.

To summarize the findings at this point, it has been determined that skin tissue may be subjected to a thermal history that produces a damage value Ω of approximately 1.5, corresponding to percentage collagen denaturation of approximately 78%, without signficant scarring or other untoward effects. This amount of thermal damage is significantly greater than the conventional Ω=1.0 or 63% damage for the threshold of thermal injury. From this finding, new laser treatment parameters can be determined that produce maximum Ω values of approximately 1.5 at depths that extend deeply into the dermis for treatment of BCC.

To determine whether malignant cells residing within the collagen matrix of skin are effectively treated (eradicated) when subjected to thermal histories that produce Ω of approximately 1.5 for collagen denaturation, the Arrhenius parameters for heat-induced killing of malignant cells are needed. Arrhenius parameter data from a variety of sources are available in the literature (see for example Feng Y, Oden J T, Rylander M N. J Biomed Eng 130; 041016, 2008, and He X, Bischof J C. Crit Rev Biomed Eng 31; 355-421, 2003). For three human tumor cell types, PC3, HeLa, and AT1, the parameters A and E are available from data corresponding to a temperature range of over 50° C. According to the present invention, it is necessary to use Arrhenius parameters derived from thermal experiments that include temperatures over 50° C., as that range corresponds to the temperatures the skin reaches when irradiated according to the present invention, for example as shown in FIG. 3. (Many studies in the literature present Arrhenius parameters for cells or tissues determined from hyperthermia experiments within the range of approximately 40 to 50° C. range, which involves a different mechanism of thermal injury than that of the higher temperatures of the present invention. Hyperthermia involves heating to approximately 41 to 45° C., whereas the term thermal therapy typically indicates heating within the approximately 50 to 70° C. temperature range. Most Arrhenius data for malignant cells corresponds to the hyperthermia treatment range, rather than thermal therapy.)

TABLE I

| depth | Ω (1 min) | | | |
|---|---|---|---|---|
| (z) | collagen | PC3 | HeLa | AT1 |
| 0.5 mm | 0.006 | 0.276 | 0.389 | 0.511 |
| 1.0 mm | 0.360 | 6.048 | 1.090 | 13.584 |
| 1.5 mm | 1.565 | 18.336 | 3.590 | 43.925 |
| 2.0 mm | 1.543 | 18.662 | 3.627 | 44.451 |
| 2.5 mm | 0.715 | 10.900 | 2.010 | 24.916 |
| 3.0 mm | 0.213 | 4.598 | 0.783 | 9.883 |

Table I shows the Ω values for tumor cells subjected to the same thermal histories as the skin in FIG. 3, as calculated herein using the appropriate Arrhenius parameters for thermal therapy. Accordingly, these values correspond to the damage (death) that would be inflicted on tumor cells if they were contained within the dermis as the skin is heated by the 10 W laser pulse. It is found that for each of the disparate three tumor cell types, the tumor cell damage is much greater than the damage in the form of collagen denaturation. (Ω=3 and 10 corresponds to 95% and 99.995% lethal damage, respectively.) Tumor cell death is produced preferentially at all depths, including at depths corresponding to the thickest skin (about 2.5 mm). This new finding leads to the conclusion herein that preferential or selective injury to malignant tumor cells, for example BCC tumor cells, can be achieved by heating skin using thermal histories that substantially avoid coagulative necrosis or scarring characteristic of all prior art thermal laser treatments of skin cancer. More specifically, an important new finding of the present invention is that tumor cells can be thermally injured to a substantially complete extent, or killed so that the tumor is eradicated, by the application of thermal histories that substantially avoid scarring or other untoward cosmetic or functional outcomes of skin treatment.

Another aspect of the present invention is the choice of laser parameters. It is advantageous to treat skin cancer with a deeply penetrating laser wavelength, specifically, a laser wavelength that is capable of penetrating at least 3 mm, or the full thickness of the thickest skin tissue (approximately 2.5 mm) plus a portion of the upper subcutaneous or adipose tissue. This objective is consistent with the clinical standard of excising the full thickness of skin, in surgical excision of skin cancer, although a significant advantage of the present invention is that it targets the tumor cells in the affected skin region of a tumor, and substantially spares the normal skin. According to the present invention, a 3 mm depth of penetration is needed to treat, for example, a mnBCC that comprises tumor cell nests that extend throughout the layers of skin on the back. Also according to the present invention, the power and irradiation time of the laser can be selected to provide different depths of maximum heating, according to the tumor type, anatomic location, and skin thickness. Although an advantageous embodiment of the present invention may use a laser as light source, it may be appreciated that other light sources can also be used, for example light emitting diodes, incandescent lamps, flashlamps or arc lamps, and any other natural or artificial incoherent light source with or without optical filters to provide light of deeply penetrating wavelengths.

Another consideration is that BCC tumors may have variable amounts of blood vessels within or at the periphery of the tumor. Use of a wavelength that is strongly or preferentially absorbed by blood to heat the tumor will lead to inconsistent results. Also, most skin tumors are located on the head or neck, and normal blood vessels in the vicinity of the tumor may be subject to iatrogenic damage if a wavelength preferentially absorbed by blood is used.

Therefore, according to the present invention, the wavelength used to treat the skin tumor should be deeply penetrating and not strongly absorbed by blood. These considerations were addressed in a previous invention of the present inventor (US20100160904, WO/2010/060097A3) for thermal therapy of soft tissues. In that invention, the wavelength range of 700 nm to 1350 nm, more advantageously 1100 nm to 1350 nm, or yet more advantageously 1100 nm to 1140 nm, was taught for thermal therapy of soft tissues including tonsils and solid tumors. Skin is of course soft tissue and BCC and other NMSC are solid tumors. The same considerations apply to the present invention.

Figure 4A:
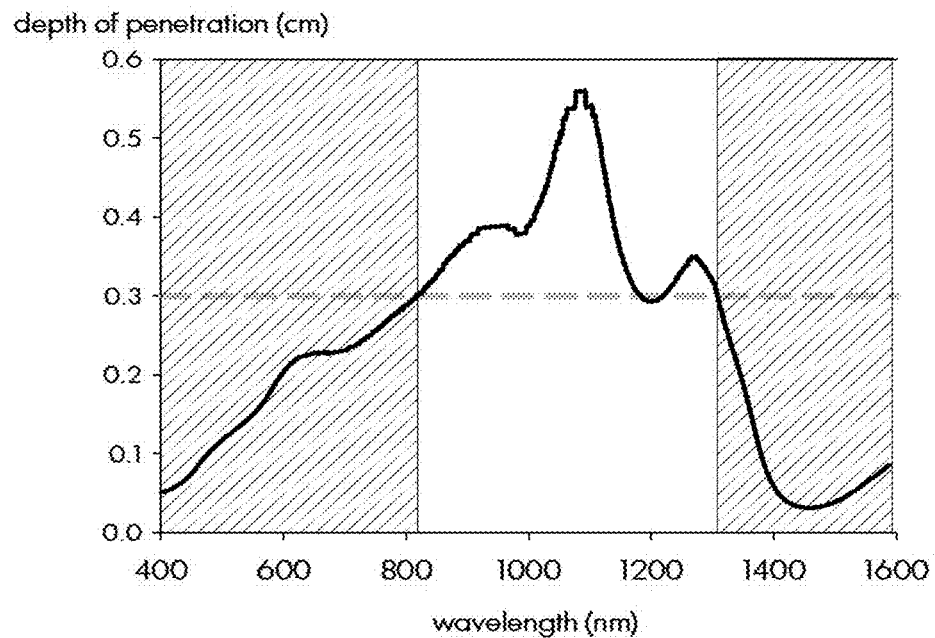
FIG. 4A shows, as an unshaded region, wavelengths corresponding to a depth of penetration in skin of at least 3 mm.

In FIG. 4A, the 1/e depth of penetration ze of light in human dermis is shown. ze was calculated from the intrinsic optical properties of human skin ($\mu_a$, $\mu_s$, and g), and the following equations:

$$\delta = 1/\sqrt{3\mu_a(\mu_a+\mu_s(1-g))} \quad \text{Eq. 2}$$

$$R_d = \exp(-7\delta\mu_a) \quad \text{Eq. 3}$$

$$k = 3 + 5.1R_d - 2\exp(-9.7R_d) \quad \text{Eq. 4}$$

$$z_e = \delta(1-\ln(k)) \quad \text{Eq. 5}$$

ze is defined as the depth at which light intensity falls to 1/e of the intensity at the tissue surface. For human skin, the maximum depth of penetration ze is about 5.6 mm at approximately 1091 nm, and ze is at least 3.0 mm at wavelengths from 811 nm to 1310 nm. In FIG. 4A, the less advantageous wavelengths that correspond to ze of less than about 3.0 mm are shaded.

It is recognized that there are different ways known in the art to define and quantify the depth of penetration of light in the skin. Therefore, the advantageous wavelength range for treatment of skin tumors may be described in an alternative, more general way as wavelengths over which the depth of penetration is at least a 0.54 (=3.0 mm/5.6 mm) of its maximum value within the visible and near-infrared spectral region.

Figure 4B:
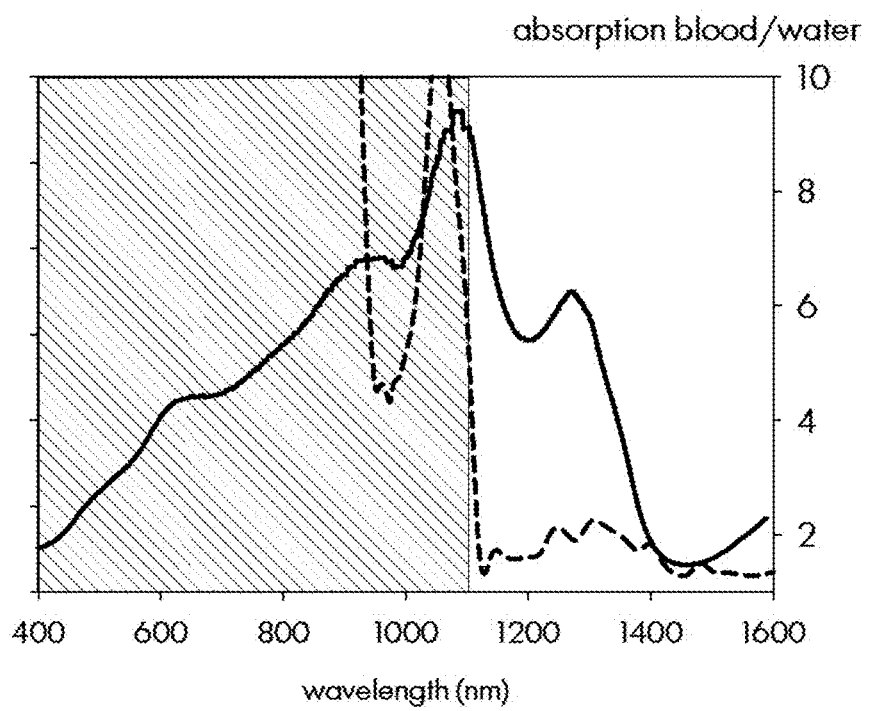
FIG. 4B shows, as an unshaded region, wavelengths where blood absorption relatively low compared to water.

In FIG. 4B, the ratio of the absorption coefficient of dilute (hematocrit 5%) well-oxygenated blood to the absorption coefficient of water is plotted over the same spectral region. It is apparent that the ratio is very high at wavelengths less than approximately 1100 nm, and that at above approximately 1100 nm, the ratio drops rapidly to a value that is low and relatively constant. In FIG. 4B, the less advantageous wavelength region where blood absorption is high relative to water (the main component in soft tissue) is shaded.

Figure 4C:
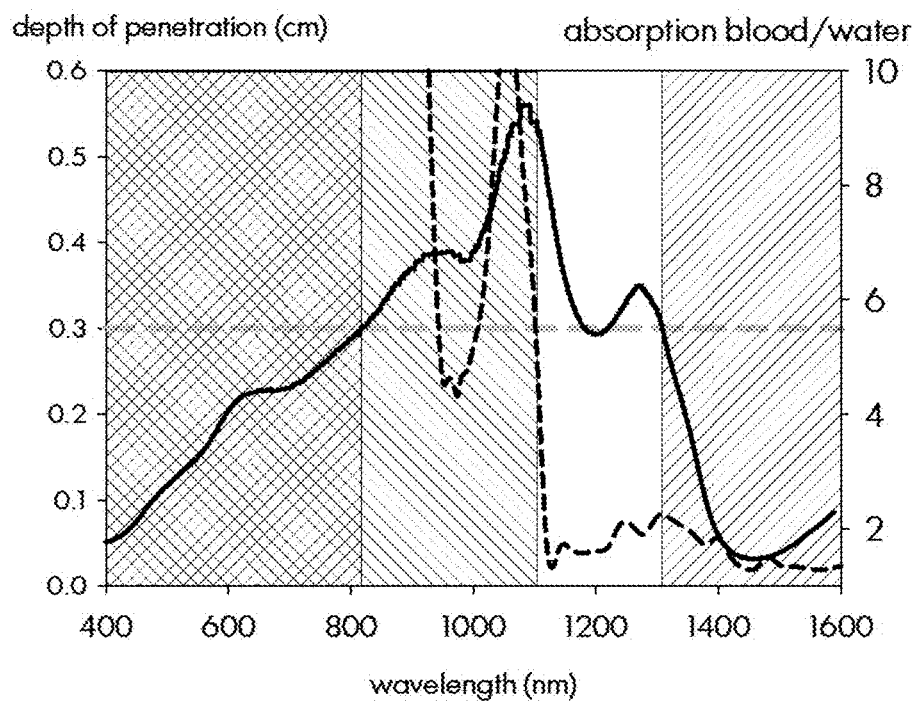
FIG. 4C shows, as an unshaded region, wavelengths corresponding to both deep penetration and low blood absorption.

FIG. 4C shows the spectral region that corresponds to both low blood absorption, and deep (approximately 3.0 mm or deeper) penetration of light in skin tissue, as the unshaded region between 1100 m and 1310 nm. According to the present invention, this region, approximately 1100 nm to 1310 nm, is an advantageous region for thermal therapy of skin, including BCC thermal therapy. The 1100 nm to 1310 nm region is within the 1100 nm to 1350 nm region identified in the previous patent applications (US20100160904, WO/2010/060097A2). Skin tissue (dermis) has a scattering coefficient that is relatively high compared to many other soft tissues (such as, for example, tonsil tissue), making it more difficult for light to penetrate deeply. Therefore while any wavelength in the previously identified 1110 nm to 1350 nm region may be used advantageously for thermal therapy of soft tissue including skin and skin cancer, the region 1100 nm to 1310 nm may be more advantageous for skin and skin cancer.

Figure 4D:
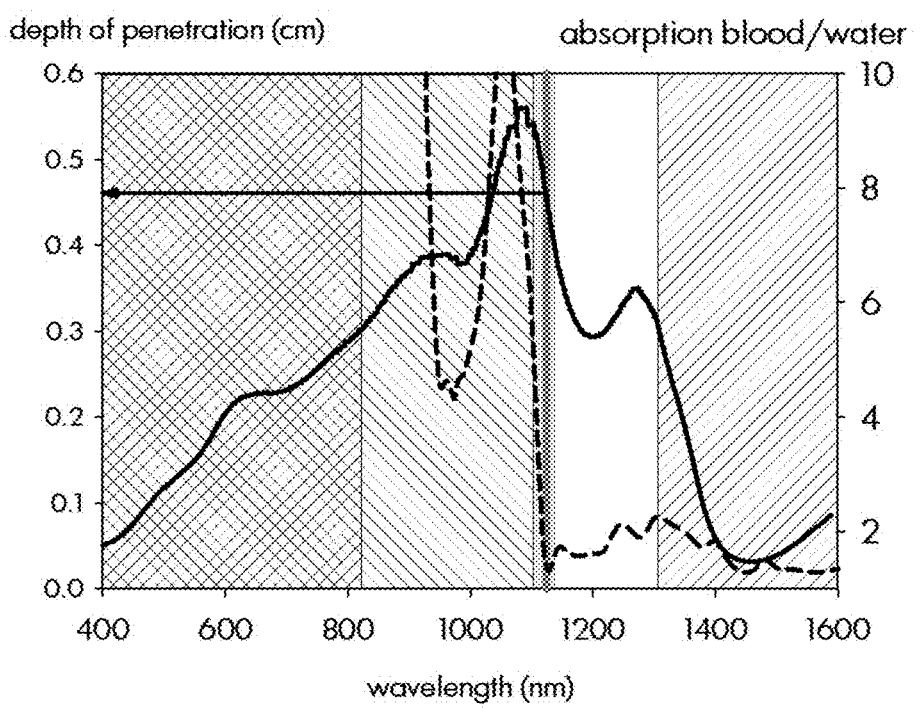
FIG. 4D shows highly advantageous wavelengths of deeper penetration.

Also, according to the present invention, within the 1100 nm to 1310 nm range of wavelengths, those corresponding to deepest penetration may be yet more advantageous. Therefore, wavelengths in the 1100 nm to 1140 nm region may be highly advantageous. The wavelength of 1125 nm, corresponding to depth of penetration $z_e$ of 4.6 mm, is an example of a highly advantageous wavelength. FIG. 4D shows the 1100 to 1140 nm region highlighted in light gray, and the 1125 nm wavelength in dark gray.

Light sources to implement the present invention are available. Considering first the advantageous wavelength region of approximately 1100 nm to 1310 nm, choices of laser technologies that can produce multiwatt, continuous wave output include the ytterbium-doped fiber laser, and the quantum dot semiconductor laser. Ytterbium fiber lasers producing multi-kilowatt powers have been introduced for use in materials working and automobile manufacturing, and lower-power models suitable for the present application are commercially available. For example, IPG Photonics (Oxford, Mass.) produces a benchtop 20 W air-cooled Yb fiber with a 3 meter delivery cable, center wavelength 1120 nm, bandwidth 2 nm (fwhm), and visible aiming beam. The system can be operated in CW mode or with externally controlled pump modulation. Because fiber lasers have a broad gain bandwidth there is the possibility of developing a medical laser that operates over multiple wavelengths or is tunable, for example within the wavelengths of 1050 nm to 1120 nm in the case of Yb-doped fiber lasers, such that the laser could be operated at 1120 nm for the present skin cancer application, or at 1064 nm for applications that the Nd:YAG laser is commonly used in dermatology, plastic surgery, otolaryngology, and other medical fields.

Wavelengths shorter than 1100 nm, and longer than about 1280 nm can be obtained using GaAs and InP diode lasers, respectively, but until recently the intervening region was not readily available from a diode source. In the past few years, however, efficient, high power semiconductor lasers based on quantum dot (QD) nanotechnology have been developed. QD lasers have advantages of enhanced gain for low operating current, high spectral purity (very narrow bandwidth), and minimal temperature effects. Innolume, Inc. (Santa Clara, Calif. and Dortmund, Germany) has commercialized QD lasers based on InAs quantum dots in GaAs with AlGaAs barriers, all on GaAs substrates. Fiber coupled quantum dot laser modules from this source producing 4 W at a center wavelength of 1120 to 1130 nm with bandwidth 3 nm fwhm are available.

In addition to lasers, incoherent light sources may be used. One such incoherent source is the tungsten halogen lamp. Because the halogen lamp has a broad emission in the visible and NIR, filters should be used to block the emission of light outside the 700 nm to 1310 nm range, or more preferably outside the 1100 nm to 1310 nm range. In addition, superluminescent diodes emitting in the 1100 nm to 1310 nm range have been demonstrated and may be used.

Although it is outside the advantageous wavelength range of 1100 nm to 1310 nm, the neodymium YAG laser operating at 1064 nm has a long history of medical use and may be used according to the invention. The 1064 nm YAG laser readily produces output powers in the range that would be necessary for it to be used as the light source in the current invention, and it is a reliable and relatively inexpensive laser well suited to fiber optic delivery. Similarly, high power diode lasers at NIR wavelengths of 810 nm, 940 nm, 980 nm and other wavelengths between 700 nm and 1100 nm are readily available, of relatively low cost, and are familiar light sources for medical and surgical applications that may also be used according to the present invention. With wavelengths shorter than about 1100 nm, additional care may be needed to avoid damaging critical normal blood vessels in the vicinity of the irradiated skin region, particularly when lesions on the face or neck are treated. Also, at these shorter wavelengths, results treatments may be less consistent due to variations in lesional vascularity.

Figure 5:
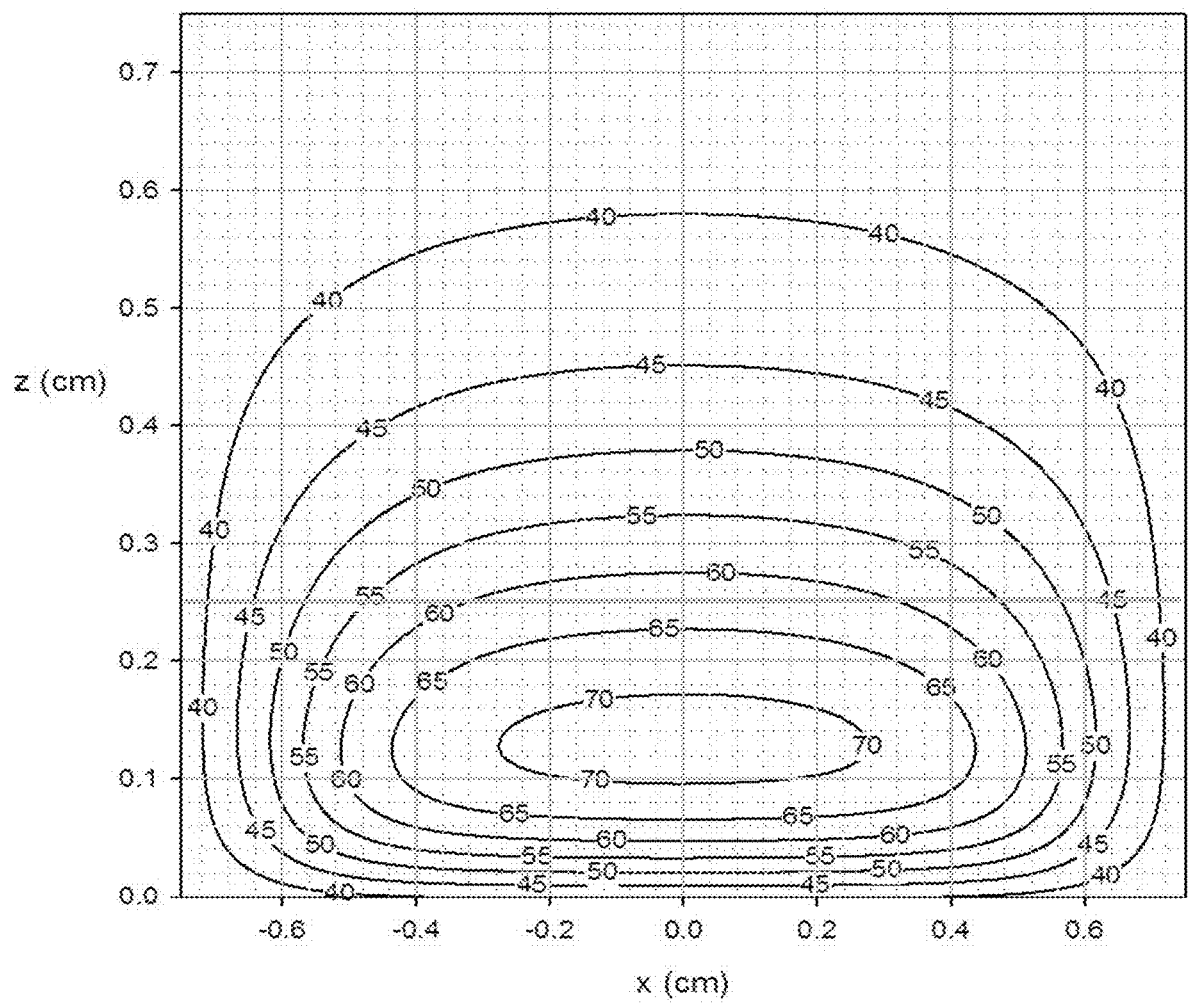
FIG. 5 is a contour plot of temperature within the skin at the end of a 20 W irradiation with an 1125 nm laser.

FIG. 3 depicted full thickness heating of skin with 10 W radiation from a 1125 nm laser. By changing the laser power, irradiation time, irradiated spot size, and/or surface cooling parameters, the depth of heating can be varied. For instance, FIG. 5 is a contour plot of skin irradiation with 1125 nm at 20 W, for 8 s, with contact cooling at 35° C. and no precooling, and a spot size of 12 mm. It can be seen, by comparison with FIG. 3, that by increasing the laser power and decreasing the irradiation time, that the region of maximum temperature increase is shifted closer to the skin surface. A laser source that would provide the parameters of either FIG. 3 or FIG. 5 is a fiber-coupled quantum dot multichip laser diode module (LD-1120-MCP-20W, Innolume GmbH, Dortmund, Germany). Depending on temperature, the laser operates with a center wavelength of between about 1120 nm and about 1130 nm. The maximum current rating of 9.9 A for this laser module corresponds to an output of approximately 36 W.

The treatment of skin with a circular spot of 12 mm diameter with flat-top (homogeneous) energy distribution and surface cooling, modeled as in FIGS. 3 and 5, can be achieved with a handpiece that accepts the output of a the laser, transmitted through an optical fiber or other transmission means known in the art.

According to the present invention, preferential damage to tumor cells can be produced using a deeply penetrating laser wavelength at parameters that heat the tumor and surrounding normal skin, so that the tumor cells in all locations within the tissue are exposed to a thermal history that corresponds to a large damage integral $\Omega$, for example a $\Omega$ of at least approximately 2, and more advantageously greater than 2, for those cells, and, secondly, that that thermal history corresponds to a damage integral $\Omega$ for surrounding normal dermal collagen that is less than approximately 1.5. However, in the currently available clinical laser treatments, the temperature within the tissue of the skin treatment site during irradiation is not measured and is unknown. In order to accurately determine $\Omega$ or any other measure of thermal injury, accurate temperature measurements are needed at representative points within the volume of tissue where the skin tumor may be located, during irradiation, and more advantageously before, during and after irradiation, and more advantageously yet, before, during, and after irradiation until the tissue has cooled. The present invention addresses this need with a novel handpiece and method for measuring temperature during irradiation, at precise locations within the tissue that are fixed and defined relative to the skin surface and the position of the impinging laser beam.

FIGS. 6A and B are side and end views, respectively, of one embodiment of a handpiece 1 for delivery of light from the light source to the skin, according to the invention. The handpiece 1 is coupled to the exit end of an optical fiber 2, such that light from the fiber is transmitted to an optical assembly 4 contained within a handpiece housing 3. The optical assembly may comprise one or more lenses to distribute the light emitted from the fiber to a distribution that is advantageously applied to the skin. For example, the optical assembly may comprise two plano-convex lenses as shown in FIG. 6A to reimage the fiber exit face onto the skin surface at some magnification and with an approximately flat-top or homogeneous light distribution at the image plane. The light passing through the optical assembly 4 is transmitted to a first window 5 that is adjacent to a cooling fluid space 7 between the first window 5 and a second window 6. Windows 5 and 6 are substantially transparent to the laser light and may be made, for example, of glass, quartz, optical plastic, or sapphire. Fluid may be passed through the space 7 from cooling input line connector 8a to cooling output line connector 8b. Connectors 8a and 8b are in turn attached to cooling lines 12a and 12b, respectively. It may be understood that the handpiece, as described above, can be modified to produce an irradiated spot of different diameters or dimensions, or different shapes (square, rectangular, oblong, hexagonal, for example) by those skilled in the art.

Attached to the handpiece is a grid element 9 that is made of a laser resistant material that is transparent or semi-transparent to the laser wavelength, and which comprises at least one temperature sensor needle 10 connected with at least one lead wire 11. The grid element 9 has a proximal surface 9a that is in contact with or adjacent to the distal surface 6a of the second window 6. When the handpiece 1 is brought into contact with the skin, the grid element distal surface 9b is in contact with the skin, and the sensor needles 10 are inserted into the skin such that the temperature sensors are at located at points within the skin when the laser is activated and light is applied to the skin. In advantageous embodiments, the grid element 9 with sensor needles 10 is a disposable component of the laser handpiece 1. The grid element 9 may have an edge section 9e with an edge section inner surface 9f that is in contact with the handpiece 1 or the window 6 when the grid element 9 is attached to the handpiece 1.

The end view of FIG. 6B shows open areas 9d in the grid element 9. The open areas allow light to pass unimpeded from the window 6 to the skin, when the handpiece is in contact with the skin. In more advantageous embodiments, the total area of the open areas 9d is a substantial fraction of the distal surface area of the window 6. The open areas 9d can have any shape, number, size, or relative placement within the grid element 9. The proximal ends of the sensor needles 10 are embedded in or attached to the grid element 9, and the sensor leads 11 travel through channels 9c in the grid element, before exiting the grid element. The channels 9c may be reflectively coated or otherwise shielded to prevent light-induced damage to the sensor leads 11. Alternatively, the sensor leads 11 may themselves be coated or shielded.

Grid elements with sensor needles were described in a previous invention of the present inventor (US20100160904, WO/2010/060097A3) for measurement of temperature during thermal therapy of tonsils and other soft tissues.

Although the handpiece is designed so that the fluid in space 7 will not be in contact with tissue, the light-transmitting fluid should be nontoxic as well as having good heat transfer properties. Fluids that are appropriate include Fluorinert™ (3M, St. Paul, Minn.), specifically, FC-77 or other Fluorinert™ fluids that have low vapor pressure at room temperature. Water and aqueous solutions may also be appropriate fluids. The fluid may also be a nontoxic gas, for example nitrogen or air.

In alternative embodiments, the windows 5 and 6 may be omitted, and the grid 9 attached directly to the housing 3 of the handpiece 1. In such embodiments, the skin surface may be precooled, for example with an ice pack or cold air. Or, the skin surface may be cooled during irradiation by flowing cold fluid such as cold air or cold nitrogen, directly on to the skin and grid element 9 using a separate cold air machine (for example, Zimmer Cryo 6, MedizinSystems Inc, Irvine Calif.). Various such cooling elements may be used according to the invention, including but not limited to the cooling layer 7 of the handpiece 1, a source of cold gas, a cooling gel, or a cold pack.

In some advantageous alternative embodiments, the cooling layer 7 and window 6 may be eliminated, and the skin passively cooled by contact with window 5 during irradiation. Window 5 may be precooled, before the handpiece is brought into contact with the skin, or after contact but before irradiation begins.

In other advantageous embodiments, the embodiment shown in FIGS. 6A and 6B for example may be used with window 6 at room temperature or a temperature that is close to normal physiologic temperature (37° C.) or any temperature in between. In more advantageous embodiments, after the end of laser irradiation the window 6 is rapidly cooled to a temperature well below room temperature to quench the laser-induced heat and stop the process of thermal damage. The quenching temperature should not be so cold as to substantially freeze the skin or cause freezing injury to the skin. For example, the handpiece of FIGS. 6A and 6B may be used to irradiate the skin surface with no fluid flowing through space 7 during the laser pulse, but at the end of the laser exposure a flow of cold air or cold liquid may be passed through said space.

It may be appreciated that the handpiece 1 may be of many different configurations known in the art. For example, instead of delivering light from a light source to the handpiece by means of an optical fiber or other transmission device, the light source may be in the handpiece. For instance, the handpiece may contain multiple diode lasers positioned so that their combined output irradiates the skin surface when the handpiece is held in contact with the skin. Or, the handpiece may contain a tungsten halogen lamp inside a reflective chamber, such that the lamp light is directed to the skin surface when the handpiece is held in contact with the skin.

Likewise, the irradiated spot on the skin produced by the handpiece may be any shape (circular, oblong, square, rectangular, hexagonal, polygonal, or of nongeometric shape), and any diameter, size, or dimension that is advantageous for treating lesions of different sizes on different sites of the body.

In advantageous configurations of the invention, the apparatus of the invention may have interchangeable or adjustable handpieces with more than one size or shape of irradiated spot, for convenient treatment of different anatomic locations. Also, a large lesion can be treated by moving the handpiece from spot to spot with or without overlap, to cover the entire lesion.

According to the present invention, the temperature at one or more points within the skin region being treated can be monitored using the temperature sensors of the grid element 9, so that the damage integral $\Omega$ can be calculated during the treatment for both normal dermis and tumor cells, using Eq. 1. In this way, the operator can ensure that, first, if tumor cells are present at the locations of the one or more temperature sensors, those tumor cells have been exposed to a thermal history that corresponds to a large damage integral $\Omega$, for example a $\Omega$ of at least approximately 2, and more advantageously greater than 2, for tumor cells, and, secondly, that if collagen fibers of normal dermis are present at said locations of the one or more temperature sensors, those collagen fibers have been exposed to a thermal history that corresponds to a damage integral $\Omega$ for normal dermal collagen that is less than approximately 1.5. In some embodiments of the invention, a display panel allows the operator to monitor temperature at each of the sensors, and also to continuously monitor $\Omega$ for tumor cells and $\Omega$ for dermal collagen, as the treatment progresses and thermal damage accumulates, at the location of each of said sensors. In advantageous embodiments of the invention, there is more than one temperature sensor. In other advantageous embodiments of the invention, the more than one temperature sensors are located at different depths within the skin tissue, for example at a depth corresponding to epidermis, a depth corresponding to dermis, and a depth corresponding to subcutaneous (adipose) tissue. In other advantageous embodiments of the invention, the more than one temperature sensors are located at different distance from the center of the impinging laser beam, within the skin tissue. In advantageous embodiments of the invention, the more than one temperature sensors are located at different depths corresponding to the location of tumor cells within the skin. In another embodiment of the invention, the signals from the temperature sensors are use to increase or decrease laser power, to in turn increase or decrease the rate of damage accumulation $d\Omega/dt$ in the skin, for either tumor cells or dermis, for better control of treatment outcomes.

For treatment of lesions with tumor cells extending into the subcutaneous tissue, the damage integral $\Omega$ for adipose tissue may also be calculated from temperature measurements in that location.

Figure 7A:
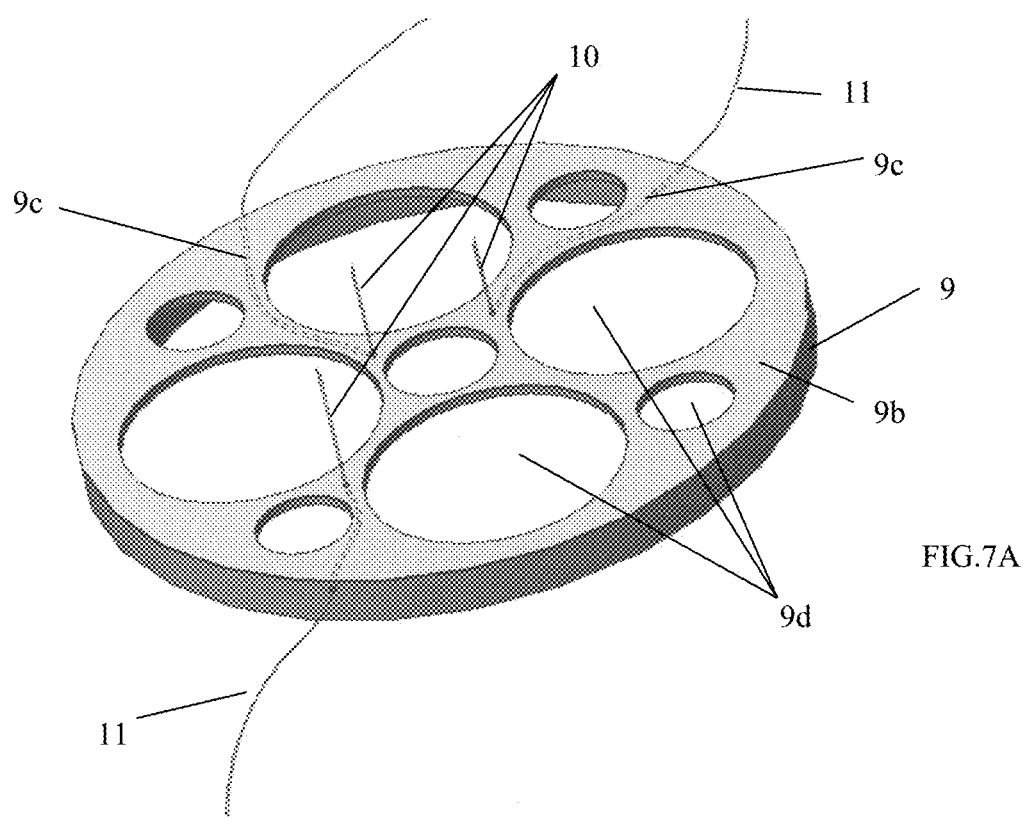
FIGS. 7A and 7B are semi-schematic views of a grid element 9 of the invention.
Figure 7B:
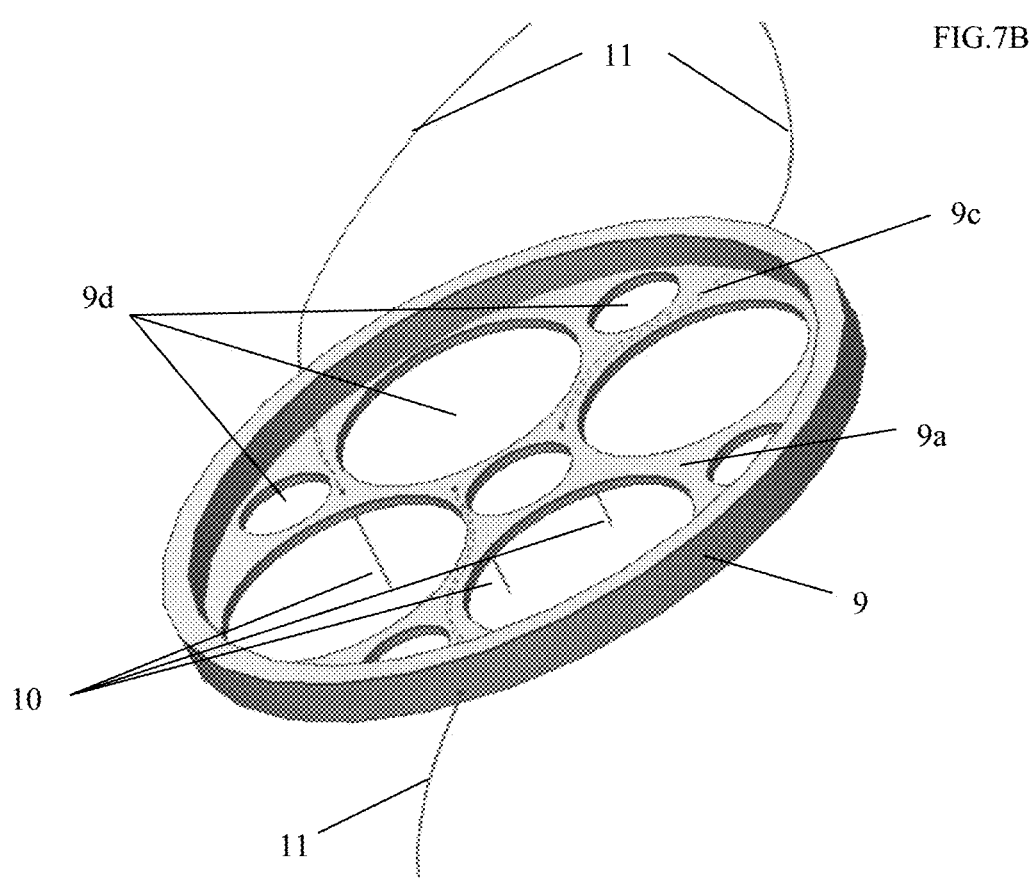

The grid element 9 may have open areas 9d of any size, number, and shape. In FIGS. 7A-B, another embodiment of the grid element is shown. FIG. 7A shows the grid element so that the distal surface 9b is facing upwards. FIG. 7B shows the grid element so that the proximal surface 9a is facing upwards. The grid element 9 may attach to the window 6 of the handpiece or to a surface of the handpiece itself by snap fitting, pressure fitting, set screw, or any other means known to those skilled in the art. In some embodiments, a thin, substantially transparent biocompatible polymeric sheet can be placed adjacent to the handpiece window prior to attachment of the grid element, to protect the window from biological contamination during treatment of a lesion. The polymeric sheet may be polyimide, polyurethane, or any such material known in the art, and may be disposable.

When grid element 9 is a disposable component, the tissue penetrating sensor needles 10 do not require sterilization after use. The remaining components of the handpiece can be cleaned as necessary and reused. It is advantageous to separate the handpiece with its optical assembly from the affixed sensor needles or other components for which reuse in patients is impractical. Optical components are expensive and may require precise relative alignment. According to the present invention, optical components can be kept substantially intact and reused, while the grid elements with needles that are inserted in the tissue can be disposed of after use so that the procedure is convenient, practical, and economically advantageous.

In one embodiment, the grid element is made of a plastic material that substantially transmits light of the wavelength or wavelengths emitted by the light source of the apparatus. In a specific embodiment, the grid element is made of polyetherimide resin, e.g. Ultem® (SABIC Innovative Plastics). In another specific embodiment, the grid element is made of a polycarbonate resin, e.g. Makrolon® (Bayer Material Science). The portion of the skin surface touching the distal surface 6a of the window 6 within the open areas 9d of the grid can be directly cooled by window distal surface 6a, and the portion of skin surface touching a portion of the grid element distal surface 9b can be cooled by contact with the grid element which in turn is in contact with the window 6 and/or by heat transfer from adjacent skin tissue directly cooled by the contact surface. Thus, a key aspect of the invention is that the grid element of the invention provides for the insertion of one or more temperature sensors at predefined distances in the tissue from the light-transmitting contact distal surface 6a of the window 6, by a means that does not interfere substantially with either delivery of light to the tissue or to the effective cooling of the tissue. In FIGS. 6A and 7A-B the attached needles are depicted as extending in a direction perpendicular to the window distal surface 6a. The needles may also be attached with an angle relative to the surface 6a.

In advantageous embodiments of the invention, each handpiece 1 of the invention is supplied with multiple grid elements 9, said grid elements having different numbers, lengths, density, or arrangement of needle sensors appropriate for certain lesion types or anatomic locations. For example, for treatment of a BCC on the back, where skin is thick, or for treatment of a lesion suspected of being deep at any anatomic location, a grid element with at least one needle of length approximately 2.5 mm or longer is used. For tumors located on thinner skin and/or overlying bone or cartilage, the longest needle on a grid element may be substantially shorter than 2.5 mm. For handpieces with larger irradiated spot sizes, multiple needles positioned near the center of the beam, at the edge of the beam, and at intervening positions may be used. For handpieces with small irradiated spot sizes, for example handpieces useful in treating small tumors in difficult anatomic locations such as near an eyelid, a single short sensor needle may be used.

A temperature sensor that is suitable for use in a sensor needle according to the present invention includes a thermocouple or a thermistor. Thermocouples housed in small diameter hypodermic needles are commercially available. Type T thermocouples are available in stainless steel hypodermic needle probes as small as 200 micron diameter from a commercial source (HYPO Mini-Hypodermic probe, Omega Engineering). Other examples of a temperature sensor in a stainless steel needle is the MLT1406 Needle Microbe Thermocouple (ADlnstruments), and the MT-23 635 micron diameter needle probe (Physitemp Instruments, Clifton, N.J.). The time constant of such needle probes is on the order of 0.1 s, making them suitable for temperature monitoring and control. In the present invention, sensor needles are of a diameter about 200 microns to about 700 microns. In one embodiment, the sensor needle diameter is about 200 microns to about 500 microns. In one embodiment of present invention, the sensor needles are made of medical grade stainless steel (316, 316L or vacuum melted type 316L). In another embodiment, the sensor needles are made of medical grade titanium (unalloyed commercially pure CP grades 1-4) or titanium alloys (including Ti-6Al-4V ELI, Ti-6Al-4V, Ti-6Al-7Nb, Ti-3Al-2.5V, Ti-13Nb-13Zr, Ti-12Mo-6Zr-2Fe, Ti-15Mo) Other metallic materials that can be used to make the sensor needles include silver, platinum, tantalum, niobium, zirconium and zirconium alloys, shape memory alloys based on the nickel-titanium binary system, tungsten and tungsten bronzes, and cobalt alloys (Elgiloy and MP35N). Needle probes made of many metallic materials, including stainless steel, will absorb light including near infrared light of the range of about 1100 nm to 1350 nm to be directly heated. Therefore, in one embodiment, the needle is made of a metal that substantially reflects light, and in another embodiment, made of gold, which is highly reflective of light. In another embodiment, a coating that substantially reflects light is applied to the exterior surface or exterior and interior surface of a sensor needle. For example, a gold coating is applied to the surface of the sensor needle. Use of a gold needle or a gold-coated needle will reduce measurement artifacts due to direct absorption of light by the sensor needle, and will allow the tissue temperature to be measured simultaneously with tissue irradiation, for the most precise and rapid control of the irradiation process. In the absence of a reflective coating, the irradiation process can be intermittently halted to measure temperature after the needle probe equilibrates with the surrounding tissue. Briefly halting the irradiation will allow accurate temperature measurements to be made with, for example, a standard stainless steel needle probe, although the total treatment time will be slightly longer as a result. Alternatively, according to the present invention, accurate temperature measurements may be made with a probe made of stainless steel or other material that absorbs light, if the signal is processed to separate out the exponential artifact signal according to methods known to those skilled in the art.

Figure 8:
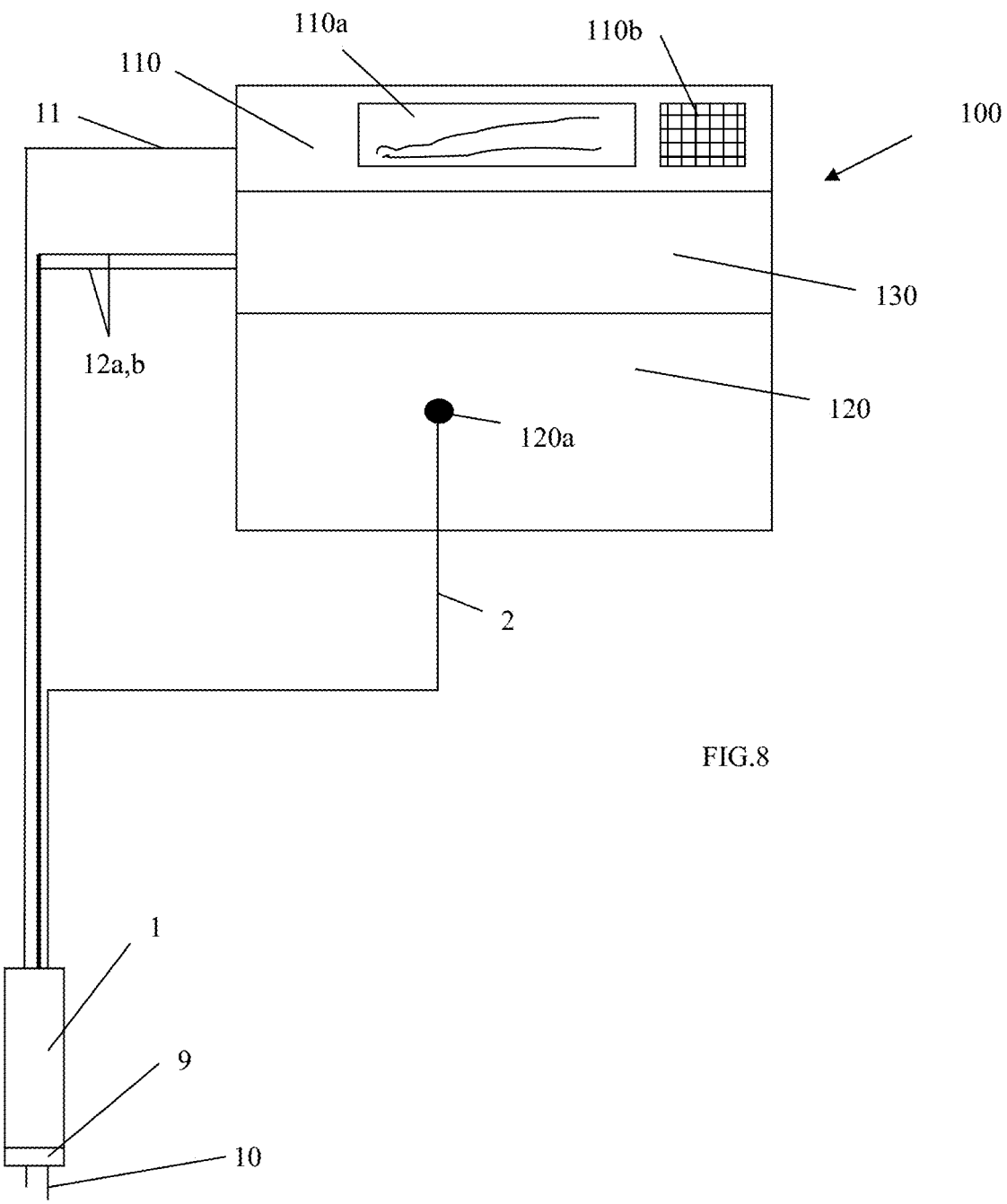
FIG. 8 is a schematic view of an apparatus 100 of the invention.

Thermocouple needle sensors are advantageous because they are inexpensive, rugged, reliable, and simple to use. Other means of temperature sensing include noninvasive, non-contact temperature sensing of the skin, such as by collecting and analyzing radiation emitted by the skin FIG. 8 is a schematic depiction of a simple embodiment of an apparatus (100) of the invention. A handpiece 1 with attached grid element 9 is connected to a system comprising a controller unit 110, a cooling unit 130, and a laser unit 120, via needle sensor leads 11, coolant lines 12a and 12b, and optical fiber 2, respectively. The controller unit will contain a microprocessor for processing the sensor signals and calculating temperature and $\Omega$, and may have a display 110a for visualization of the temperature or damage $\Omega$ at the locations of the sensors in the skin. The controller may also have a display panel 110b for adjusting the laser parameters or operating the apparatus, including the cooling system. The laser unit will have a light output aperture 120a to which the optical fiber connects. The laser unit may be more generally a light unit, when incoherent light sources are used. The cooling unit may be a recirculating chiller or a cold air machine, for example.

There is considerable flexibility to cooling in the present invention. When used, cooling can be initiated before the handpiece is placed on the skin, before irradiation begins or during irradiation, or after irradiation ceases. Initiation and ending of cooling and irradiation may all be performed under operator control with operator monitoring of the treatment progress, or may be under microprocessor control. Cooling temperature may be varied during the time the handpiece is on the skin.

Figure 9:
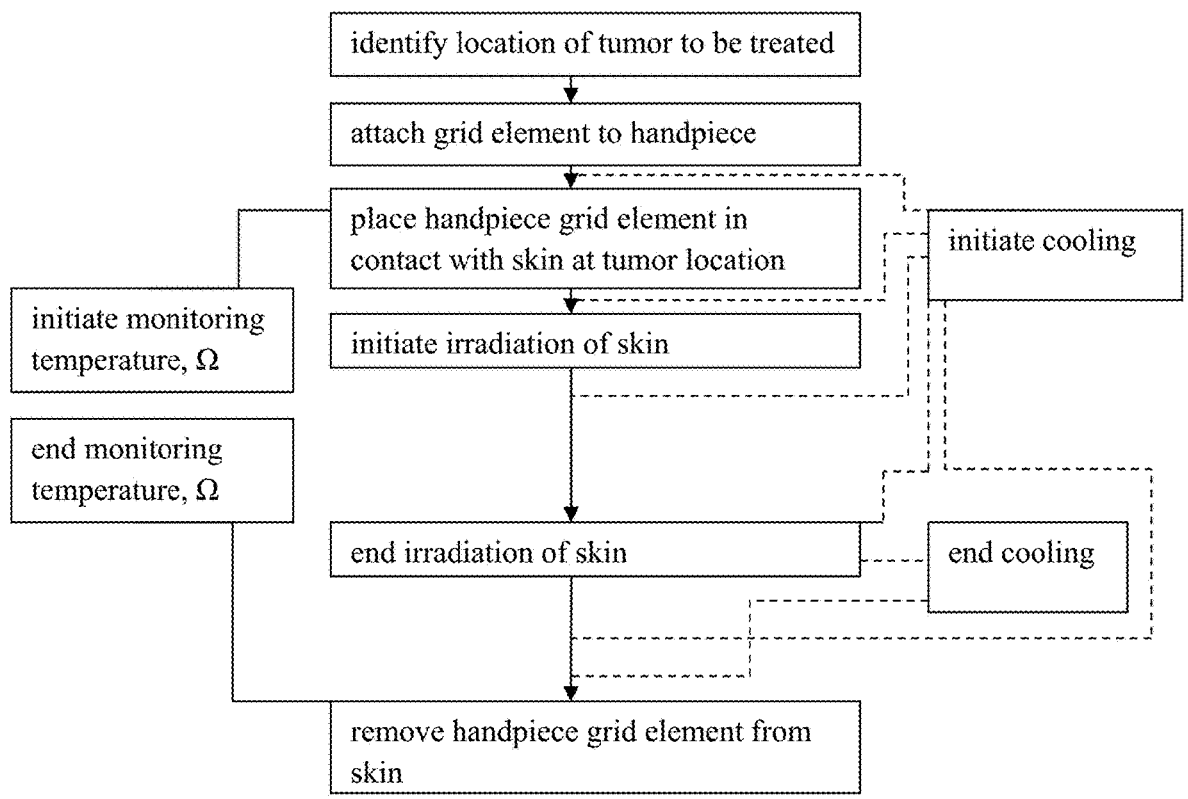
FIG. 9 is a treatment schema of the invention, using laser thermal therapy.

A simple treatment schema for skin cancer thermal therapy is shown in FIG. 9.

In advantageous embodiments of the invention, the epidermis is protected from the heat generated by high radiant fluence rates caused by backscattering of light within the tissue by surface cooling. This has the advantage of protecting normal epidermis in the vicinity of a skin tumor and minimizing scarring. However, skin tumor cells may be within, closely adherent to, or adjacent to the epidermis overlying a skin tumor. In that case, surface cooling and epidermal protection may reduce the thermal damage of the superficial tumor cells. Therefore, in an advantageous embodiment of the invention, thermal therapy is combined with topical administration of a antineoplastic or anticancer agent to increase tumor cell killing throughout the tumor, and especially at or near the epidermal surface. This may be accomplished by application of the topical drug after laser treatment. However, because topical drug exposure is highly dependent on the epidermal permeability, and epidermal permeability in the region of a BCC or other lesion may be low or high depending on how intact the stratum corneum is, topical anticancer or chemotherapeutic drugs as used in the prior art for treatment of skin cancer have inconsistent and inadequate efficacy. A more consistent drug exposure is advantageous. The present invention addresses this problem by the use of a grid element that increases epidermal permeability in a consistent manner.

Figure 10:
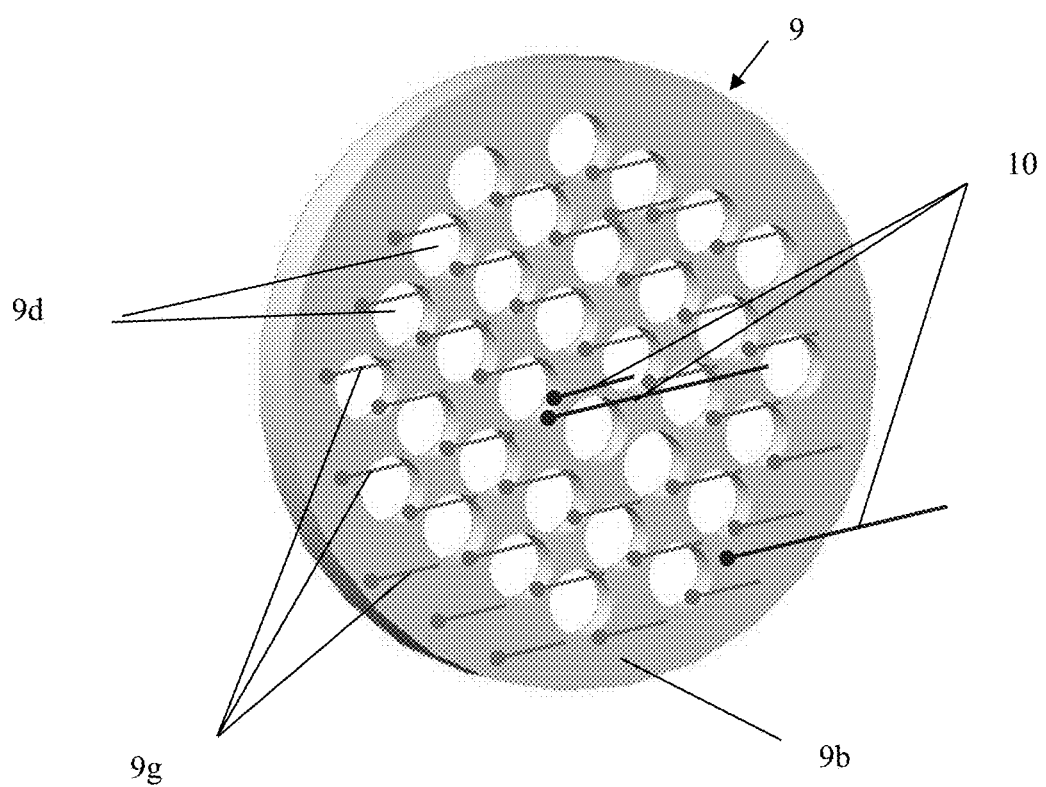
FIG. 10. is a semi-schematic view of a grid element 9 of the invention, with permeability needles 9g and sensor needles 10.

FIG. 10 shows a grid element 9 with an array of permeability needles 9g extending from the grid distal surface 9b. The grid element also has sensor needles 10 for measuring tissue temperature. The permeability needles 9g produce holes through part or all of the epidermis, so that the topical drug circumvents the primary barrier to the skin. In advantageous embodiments, the permeability needles are arranged in a distribution that includes most of the irradiated area on the skin. The permeability needles may be hollow or solid, and may be made of any rigid, biocompatible material that is strong enough to pierce the skin, including the materials listed above for the sensor needles.

The permeability needles may be of the same or similar diameter or gauge as the sensor needles described previously, or may be much smaller, for example microneedles.

The permeability needles 9g can be made from or coated with a material, such as gold, that is reflective of near infrared light. However, in advantageous embodiments of the invention, the permeability needles are uncoated or partially coated, so that they absorb radiation and are heated during the skin irradiation. In this manner, the tissue surrounding the holes created by the needles may be at least partially coagulated or denatured, and the holes will retain their patency for a longer time.

In embodiments of the invention using multiple temperature sensor needles, or in treatment of skin tumors that have a defective or damaged epidermis, permeability needles may be unnecessary to achieve adequate and consistent drug penetration through the epidermis.

Figure 11:
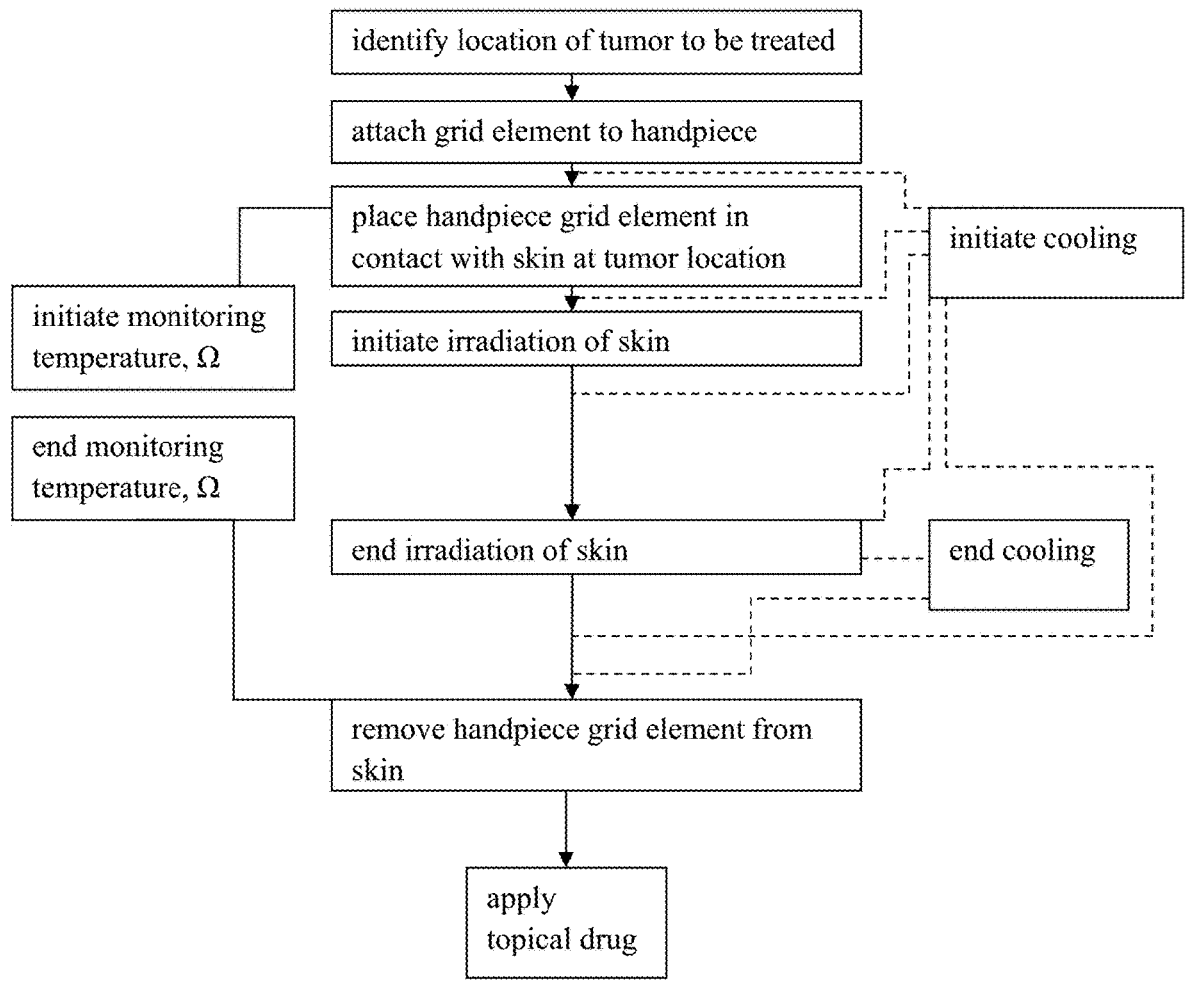
FIG. 11 is a treatment schema of the invention, using laser thermal therapy and a topical drug.

A simple treatment schema for skin cancer thermal therapy that includes topical administration of an anticancer drug is shown in FIG. 11. The grid element of embodiments of the invention used in this schema may have permeability needles and sensor needles, or only sensor needles, An important aspect of be present invention is that it may be used with any topical or surface-applied drug or therapeutic agent, for an improved treatment of skin cancers and other lesions of the skin. Creation of holes in the stratum corneum and the epidermis will increase permeability of the epidermis to any drug or agent, regardless of the drug's chemical properties, for example its lipophilic or hydrophilic nature, molecular size, molecular charge, or its formulation (solution, carrier, emulsion, cream, and the like). Drugs may include chemotherapeutic agents, cytotoxic drugs, bioreductive drugs, antiproliferative agents, retinoids, vitamins, antioxidents, anti-angiogenic agents, immunomodulatory agents, photodynamic drugs, pro-apoptotic drugs, antimetabolites, COX inhibitors or any other agents that may be useful directly or indirectly in killing or damaging, or reducing the growth or proliferation of, tumor cells, malignant cells, dysplastic cells, diseased cells or abnormal cells.

A specific example includes vitamin D and its analogs, which recent research has shown to have immunomodulatory, antiproliferative, and prodifferentiative effects. This group of drugs includes calcipotriol (calcipotriene), a synthetic vitamin D3 analog used for the treatment of psoriasis, and available in a 0.005% ointment or cream formulation (Dovonex, Warner Chilcott, Rockaway N.J.; Psorcutan, Intendis, Germany). Repeated application of topical calcipotriol over a period of several weeks has recently been reported in the medical literature to have some efficacy in treatment of actinic keratoses (AK), a premalignant or early form of squamous cell cancer (SCC) of the skin, in treatment of warts, benign viral tumors of the skin, and in treatment of Kaposi's sarcoma and cutaneous T-cell lymphoma. The naturally occurring active form of vitamin D3, calcitriol (Vectical, Galderma, 3 mcg/g topical) has recently been approved in the US for treatment of psoriasis. Both calcipotriol and calcitriol have poor penetration through intact stratum corneum. When used according to the present invention, and applied to the site of a skin lesion after the skin tissue has been made more permeable, proliferative cells such as BCC cells may have much greater exposure to vitamin D analogs including calcitriol and calcipotriol, for a highly effective treatment.

Topical application of the retinoid tazarotene (0.1%) on a daily basis for up to 8 months has been reported to provide complete or partial results in treatment of BCC. Tazarotene (Tazorac, 0.05% or 0.1% gel, Allergan, Irvine Calif.) is approved as a topical treatment for psoriasis and acne; however retinoid drugs are also known to control the development and spread of cancer cells and cell proliferation. Tazarotene has limited skin penetration, due to the stratum corneum barrier, which may account for the lengthy treatment regime and incomplete efficacy for BCC treatment. All-trans-retinoic acid has shown antiangiogenic and anticancer properties when given intravenously. With the present invention, it is possible to apply all-trans-retinoic acid topically as a treatment for skin cancer.

Another example of a cytotoxic drug that may be used according to the present invention is a 6% solution of miltefosine (Miltex, Asta Medica, Germany). Miltefosine acts on cell membrane phospholipids and has been used with some reported efficacy in treatment of skin metastases in breast cancer and cutaneous T cell lymphoma, with daily application for at least several weeks. Miltefosine efficacy for those skin tumors as well as BCC will increase with the present invention. Yet another group of therapeutic agents that may be used advantageously according to the present invention are COX inhibitors. Examples include diclofen, a nonsteroidal anti-inflammatory drug and nonspecific COX inhibitor that is used in a 3% gel formulation (Solaraze, PharmaDerm, Melville N.Y.) for treatment of AK; celecoxib, valdecoxib, and sulindac, among others.

Antioxidants have been shown to have promise in treatment and prention of cancer. Topical treatment with resveratrol, an antioxidant found in grapes and berries, black raspberry extract, pomegranate seed oil, grape seed proanthrocyanidins, beta carotene, ascorbic acid, and lycopene are examples.

The above is only a partial listing of drugs or therapeutic agents that are useful according to the present invention. Also, of those described, alternative formulations or dosages may prove advantageous in treatment of tissue modified by the laser treatment of the invention. Furthermore, combinations of two or more drugs may be used with said laser treatment.

An important aspect of embodiments of the invention is that exposure to a topical drug or anticancer agent by cells that are thermally injured will increase injury to those cells. For example, cells that are injured by heat from the thermal laser will receive further injury from the cytotoxin or anticancer agent. In advantageous embodiments, sublethal thermal damage will be augmented by the drug exposure to produce irreversible cell death in the tumor. In these embodiments of the invention, for given thermal history $\Omega$ for tumor cells is increased, compared to thermal laser exposure alone, whereas $\Omega$ for collagen fibers is unchanged Appropriate values of A and E in the Arrhenius equation can be experimentally determined at in tissue or cells in the presence of drug, to allow the calculation of $\Omega$ for exposure to temperatures in the range of 50° C. and higher for before, during, and after skin irradiation. A and E for cells and tissue can be determined from isothermal temperature exposures, according to methods known in the art. A key important aspect of these embodiments is that the physical process of collagen denaturation by heat will be substantially unaffected by the presence of cytotoxic drugs, whereas tumor cells will receive a significantly increased insult, further increasing the difference between dermal collagen damage and tumor cell damage for a given thermal history during treatment. In these embodiments of the invention, efficacy in eradication of malignant cells is further increased while preserving normal skin tissue.

In another embodiment of the present invention, the thermal laser or light treatment in the approximately 1100 nm to 1310 nm range may be combined with a vascular laser treatment intended to selectively damage tumor cells. The use of a vascular laser for treatment of tumors of the skin and other epithelial tissue layers has been described by the present inventor in WO/2010/102099A1 Method and Apparatus for Cancer Therapy. Vascular targeting selectively damages blood vessels, and induces hypoxia in the tumor cells that rely upon that vasculature. By this mechanism, vascular targeting may induce tumor cell death. The indirect induction of tumor cell death by hypoxia can be combined with the direct induction of tumor cell death by heating with a thermal laser.

For example, in one embodiment, a thermal laser treatment using a laser or light source in the approximately 1100 nm to 1310 nm range as described above is followed by a treatment with a vascular laser or light source, for example a pulsed dye laser, KTP laser, frequency doubled Nd:YAG laser, alexandrite laser, or filtered flashlamp (intense pulsed light source). These vascular targeting devices are well known in the art, are routinely used for treatment of cutaneous vascular lesions such port wine stain birthmarks and telangiectasias, and typically deliver light to the skin using a handpiece held adjacent to or in contact with the skin, and also typically employ surface cooling.

Figure 12:
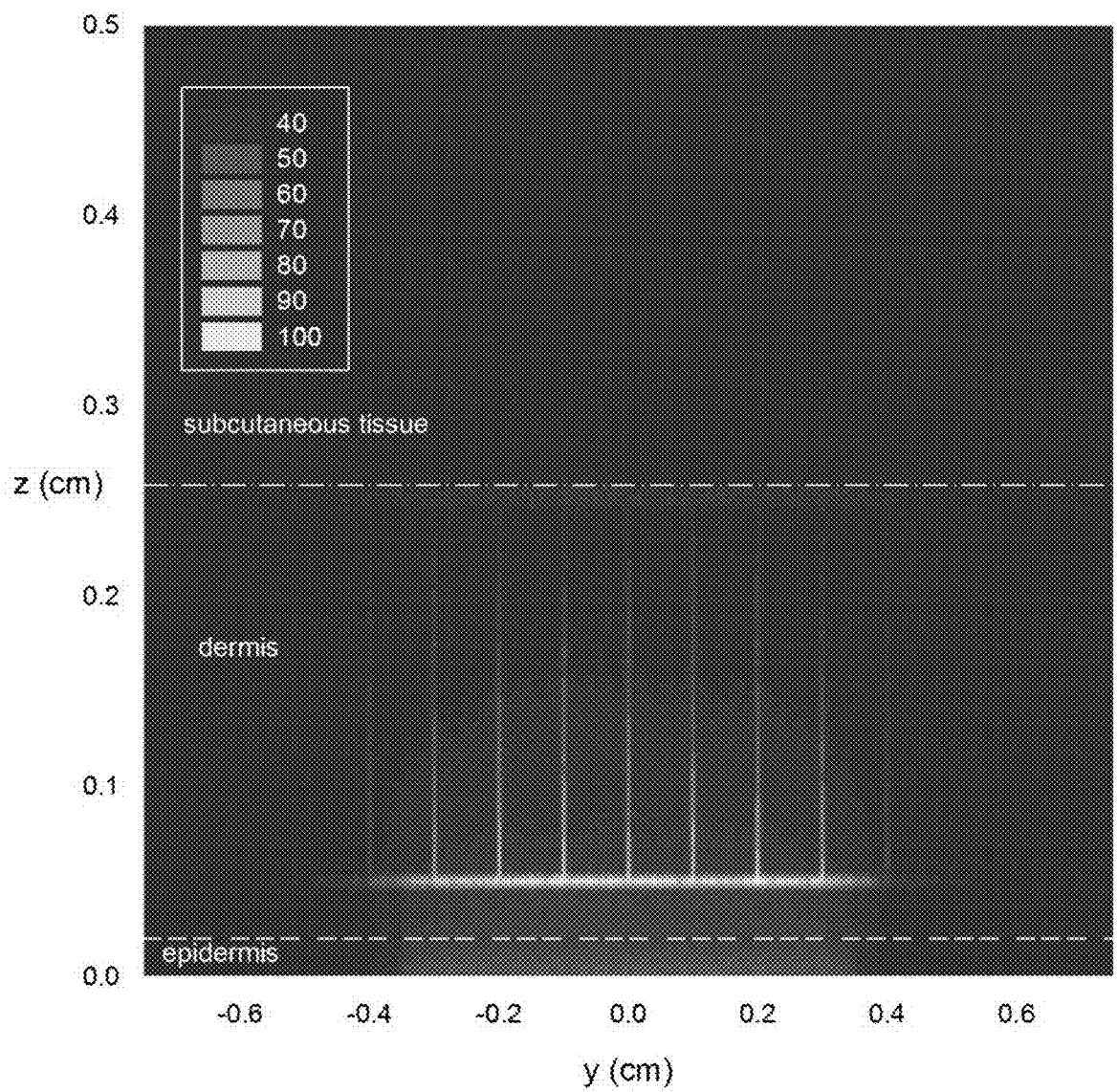
FIG. 12 is a contour plot of temperature within the skin at the end of a 4 J/cm2 pulsed dye laser pulse, showing vascular damage in the upper dermis.
Figure 13:
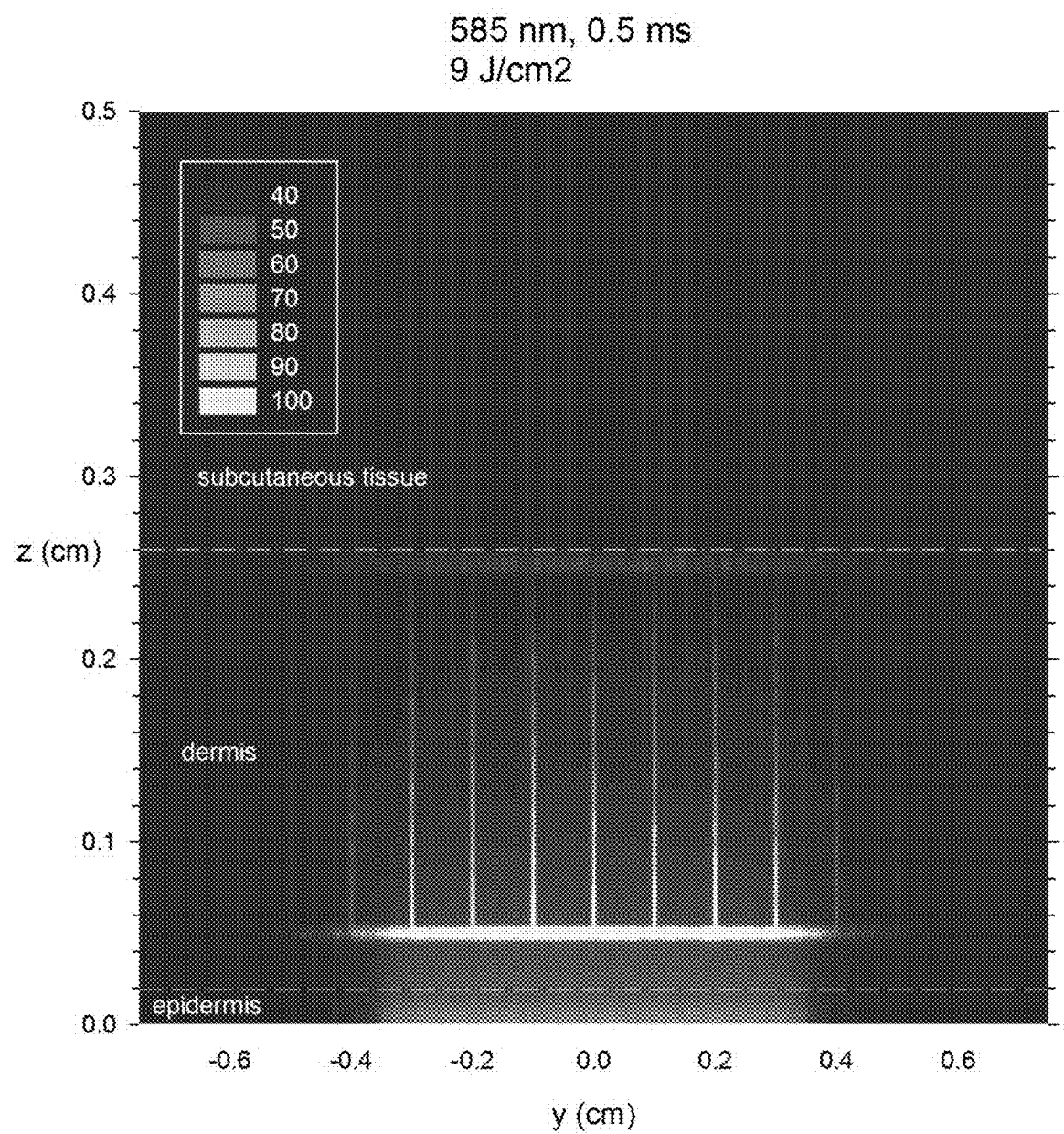
FIG. 13 is a contour plot of temperature within the skin at the end of a 9 J/cm2 pulsed dye laser pulse, showing more extensive vascular damage.

FIGS. 12 and 13 depict the results of Monte Carlo simulations of the effect of an exemplary vascular laser on skin. The calculation volume is rectangular with 2 cm by 2 cm surface area and a depth of 1 cm. The resolution of the Monte Carlo calculation in each direction is 50 One million photons are included in each calculation, which assumes a flat-top laser beam incident on the skin tissue surface. Heat transfer calculations are done numerically by a finite-difference method.

In these model calculations, tissue is represented by the following layers, beginning with the topmost or most superficial layer: (1) epidermis, assumed to be a layer 100 µm in thickness, (2) dermis, 2.6 mm in thickness, and (3) subcutaneous tissue, with infinite thickness. Also in the model, the microvasculature of the dermis is represented by two horizontal 50 µm diameter blood vessels located 0.5 and 2.5 mm under the surface, representing the upper and lower vascular plexuses, respectively, and a series of vertical 50 µm diameter blood vessels spaced 1 mm apart, connecting the two horizontal vessels. The vertical vessels represent the ascending and descending vessels of the dermis. Not explicitly include are capillary sized vessels, which are less than 10 microns in diameter and too small to be modeled, however the absorption coefficient for dermis used in the model reflects the blood component of capillaries. Also not explicitly included in the model is the stratum corneum of the epidermis, which is only about 20 µm thick.

In FIG. 12, the results are shown, in the form of a contour plot of temperature at the end of the laser pulse, as a function of location under the skin surface. In this and the other contour plots provided herein, y is a dimension parallel to the tissue surface, z is the depth perpendicular to the surface, and the origin of the coordinate system is the center of the laser beam on the tissue. In this particular calculation, the model assumes pulses with 0.5 ms pulse duration and fluence (energy density on the skin surface) of 4 J/cm2. The pulse has a diameter on the skin surface of 7 mm, and a top-hat, evenly distributed beam profile. (The choice of laser pulse diameter was limited by the resolution and calculation volume in the mathematical model, and does not represent a limit in implementation.) The skin is exposed to room temperature air during the non-contact pulse. As is known to those skilled in the art, these laser parameters from a 585 nm PDL typically produce microvascular injury within the dermis, evidenced by purpura or bruising. As can be seen in FIG. 12, the model calculation accurately predicts vascular coagulation across the horizontal vessel of the upper plexus, as well as upper portions of the vertical vessels, in agreement with clinically observed purpura. The 4 J/cm2 laser pulse produces temperatures of at least 70° C. in the vertical blood vessels down to a depth of 1.5 mm near the center of the beam, and 1.0 mm near the edges. In agreement with clinical observation, the PDL at this fluence substantially avoids temperatures corresponding to thermal injury to the overlying epidermis.

In FIG. 13, the same model is used with pulses of higher fluence (9 J/cm2). This fluence is seen to produce increased heating of the dermal microvasculature, with blood vessel coagulation expected down to about 1.5 mm at the edges and 1.9 mm near the center. Again, the areas of dermis surrounding the blood vessel are substantially unheated. The epidermis shows heating in the 60 to 70° C. range, which may be expected to cause some thermal injury within this layer. Again, this calculation is in agreement with clinical experience, and supports the accuracy of the mathematical model developed herein. Clinically, in the treatment of skin lesions such as PWS birthmarks, these laser parameters would require skin cooling to protect and preserve the epidermis for optimal cosmetic outcome. Skin cooling may take the form of a cryogen spray, a chilled contact element such as a window or lens, a cooling fluid, cold air applied to the skin surface before, during, and/or after a laser pulse, or any other means known in the art.

By combining the thermal therapy with vascular targeting, efficacy may be increased without substantial loss of preferential tumor cell killing. The important aspect of combining vascular laser treatment and thermal laser treatment of skin tumors is that both treatments are selective and sparing of normal tissue. The vascular treatment selectively injures dermal microvasculature that supply tumor cells, inducing hypoxia and indirectly killing those cells. The thermal laser treatment preferentially kills tumor cells, directly, by heating those cells. The spatial range of the two therapies overlaps, but the vascular treatment has its greatest effect in the superficial and mid dermis, whereas the thermal laser treatment is capable of having a strong effect down to the deep dermis or below. The mechanism of action of the vascular and thermal treatments are different, allowing the two to be combined to eradicate tumor cells throughout the entire tumor from epidermis to subcutaneous tissue, and still maintain selectivity for tumor cells The present invention can be implemented by combining the thermal therapy pulse and the vascular treatment pulse in either order. It is recognized herein that is that when thermal laser therapy follows the production of purpura by a vascular targeting treatment, the purpura is indicative of altered optical properties of the skin. Specifically, purpura is a discoloration that is indicative of thermally denatured blood. It is known that blood in vessels heated by lasers or light may undergo oxidation to a hemoglobin species referred to a methemoglobin, and that methemoglobin absorbs more strongly than oxyhemoglobin at longer wavelengths in the near infrared. According to the present invention, it is advantageous to avoid strong absorption of laser light by the denatured blood containing methemoglobin, in a region of the skin that has been previously treated with a vascular laser to produce purpura.

Figure 14:
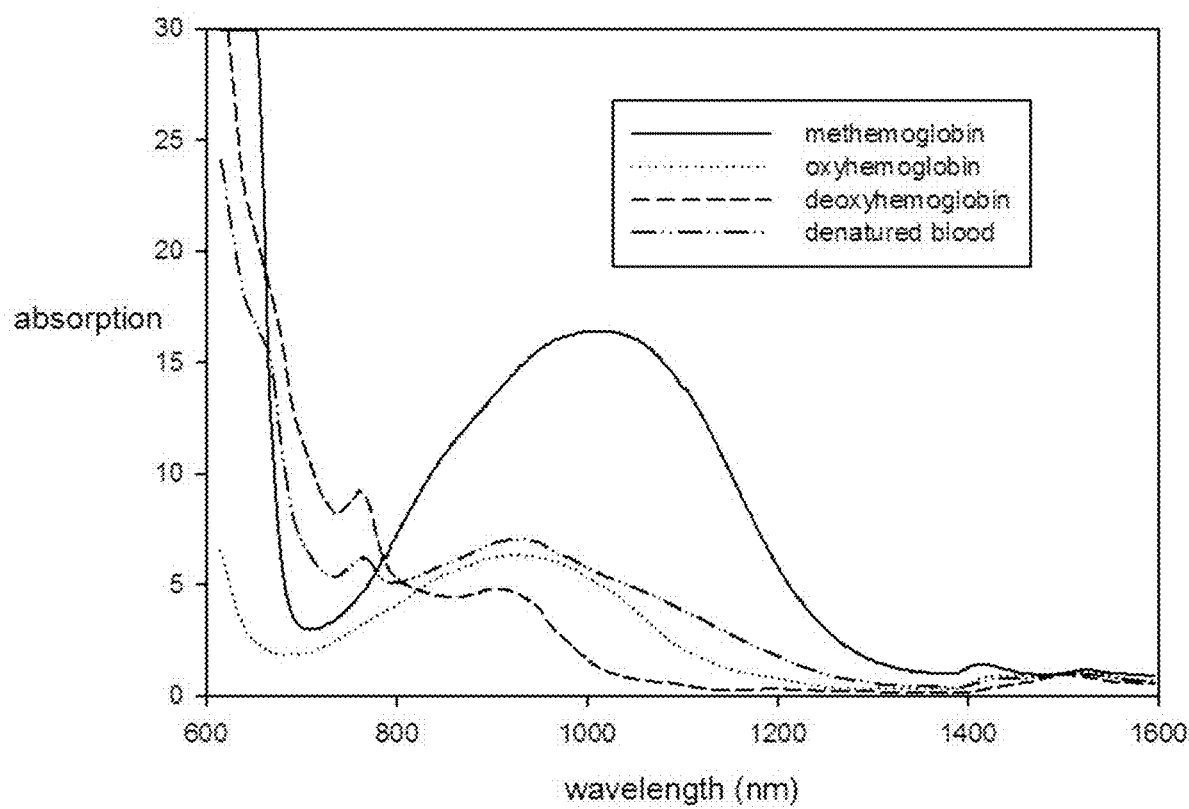
FIG. 14 is shows the absorption spectrum of coagulated blood and its constituents.
Figure 15:
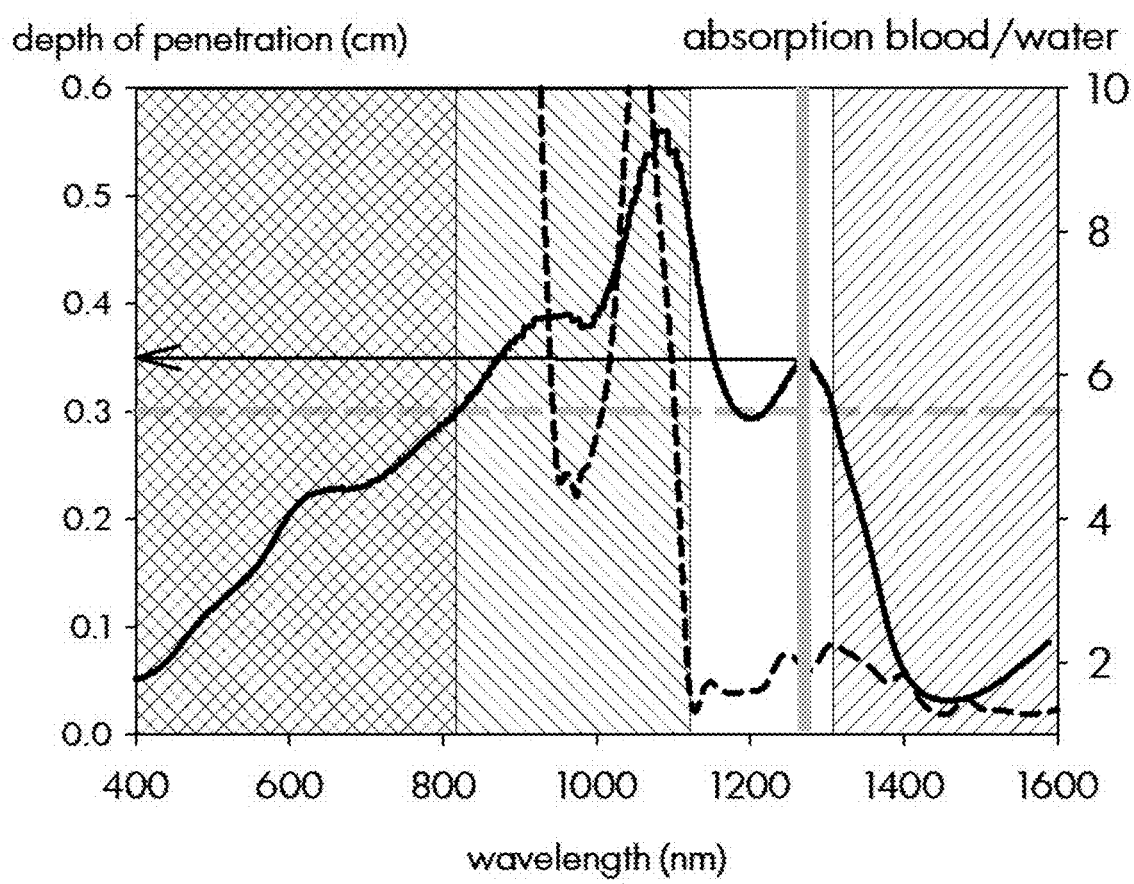
FIG. 15 depicts an advantageous treatment wavelength.

FIG. 14 shows the absorption spectra of the three hemoglobin species oxyhemoglobin, deoxyhemoglobin, and methemoglobin. It is apparent that methemoglobin absorbs much more strongly in the 1125 nm to 1310 nm region than does oxyhemoglobin, the predominant species in well oxygenated blood. However, well oxygenated blood undergoes two changes when it denatures—oxidation to methemoglobin, and loss of oxygen. Thus there is also an increase in deoxyhemoglobin. Representative concentrations in denatured blood of a purpuric skin area are 20% oxyhemoglobin, 30% methemoglobin, and 50% deoxyhemoglobin. The spectrum of this representative purpuric blood was calculated and is also shown in FIG. 14. It is found that the conversion to deoxyhemoglobin offsets most of the change to methemoglobin the 1125 nm to 1310 nm region, so that the increase in absorption of the hemoglobins in the denatured blood is only slightly higher than that of oxyhemoglobin. This novel finding allows wavelengths of approximately 1125 nm to 1310 nm to be used to treat skin tumors in skin that has first been treated with a vascular laser or other light source that has thermally injured dermal blood vessels so as to produce purpura. In addition to 1125 nm, another advantageous wavelength for thermal therapy following vascular treatment is shown in FIG. 15. At approximately 1270 nm, the depth of penetration of light is approximately 3.6 mm, and interference from denatured blood is low.

Figure 16:
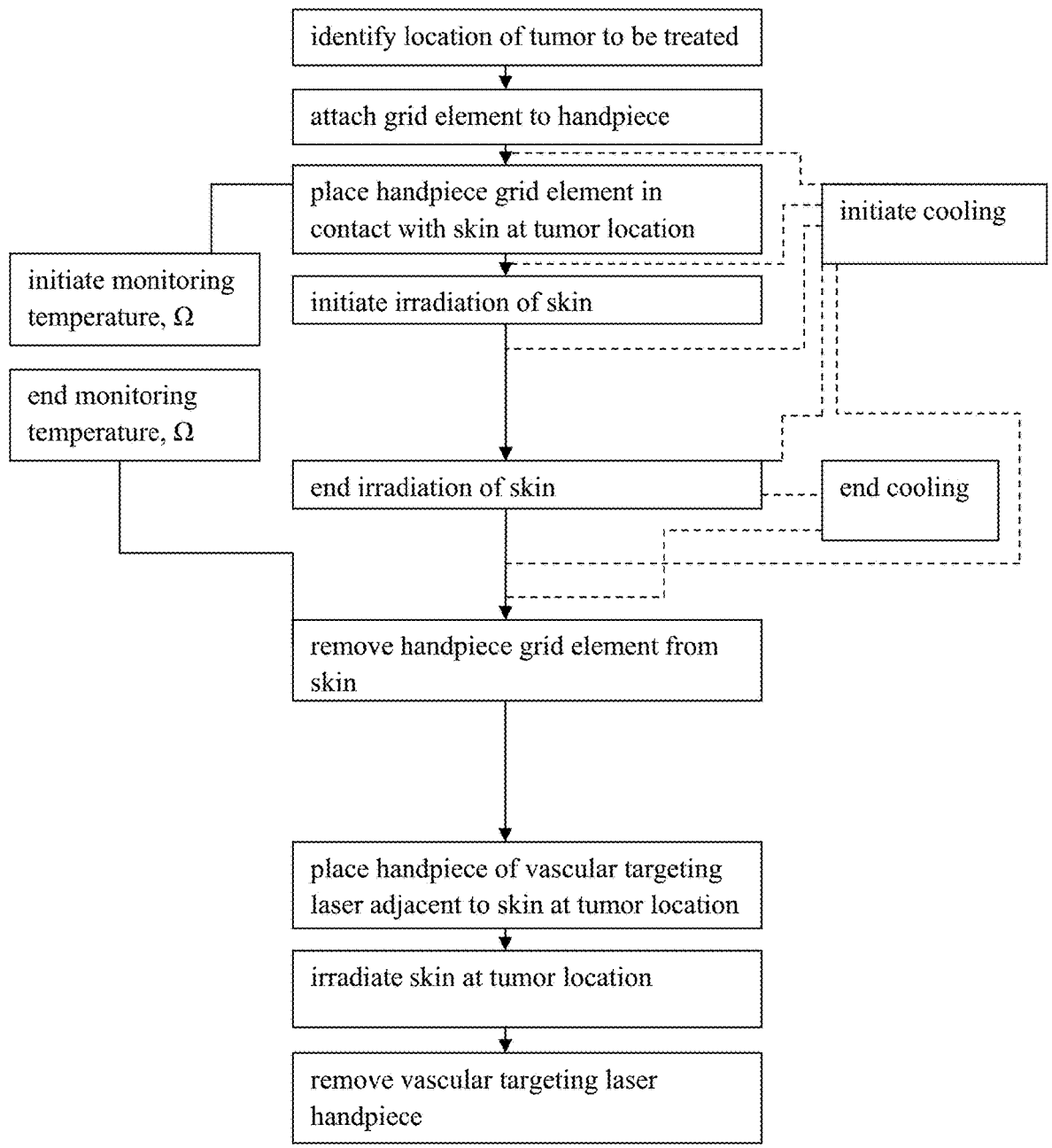
FIG. 16 is a treatment schema of the invention, using laser thermal therapy and vascular laser treatment.

A simple treatment schema according to the present invention combining thermal therapy with vascular targeting is shown in FIG. 16. It may be particularly advantageous to further cool the skin after thermal therapy but before vascular targeting, so that the skin is at physiologic temperature and responds to vascular targeting in a consistent, predictable manner.

Figure 17:
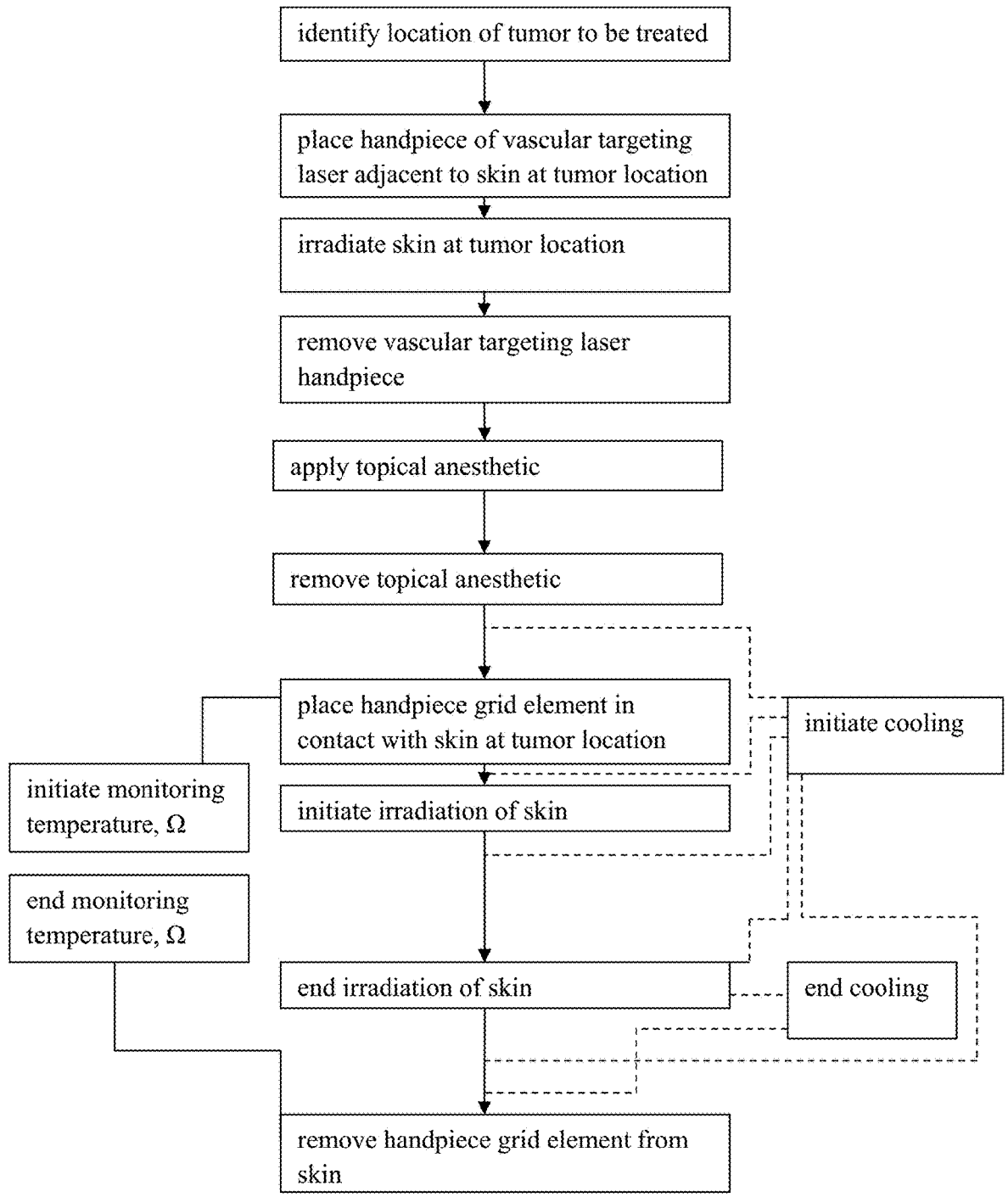
FIG. 17 is a treatment schema of the invention, using vascular laser treatment and topical anesthetic administration, followed by laser thermal therapy.

Another treatment schema is shown in FIG. 17, for treatment according to the invention with thermal therapy, vascular targeting, and a topical anesthetic agent. In this schema, vascular laser irradiation of a skin tumor is followed by application of topical anesthetic to the tumor site on the skin. In some advantageous embodiments, an ablation element attached to the vascular laser handpiece produces an array of ablations in at least the stratum corneum of the epidermis of the skin tumor site during vascular laser irradiation, said ablations increasing the permeability of the epidermis. The topical anesthetic agent is applied immediately after irradiation when the vascular handpiece is removed from the skin surface, or, in some embodiments, after the formation of purpura at the irradiation site. In purpuric skin, dermal permeability is reduced because the reduction in blood flow reduces uptake of drug by microvasculature. Consequently, the drug stays in the dermis longer, dermal drug exposure is increased, and the potentially deleterious systemic uptake of the topical anesthetic drug is reduced. The thermal laser irradiation is applied after the anesthetic drug has been on the purpuric skin for a sufficient time to produce numbing of the treatment site and after the topical drug is removed from the skin. Thermal laser irradiation is applied with monitoring of temperature and damage $\Omega$, and in advantageous embodiments includes skin cooling. In embodiments of the invention depicted in the schema of FIG. 17, effective tumor treatment is achieved with a concomitant reduction in pain from the thermal laser irradiation.

Figure 18:
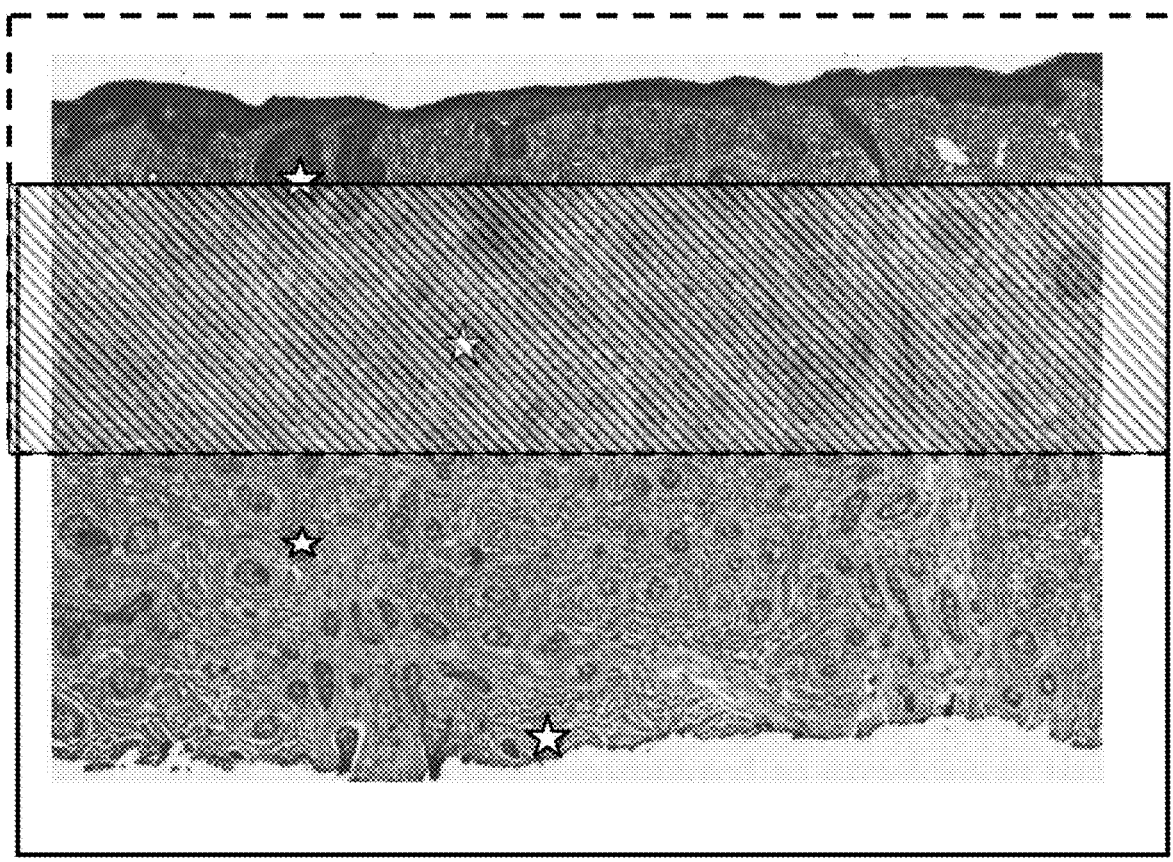
FIG. 18 is a schematic representation of the zones of skin affected by a vascular laser (dashed outline), thermal laser (solid outline), and both (diagonal hash marks).

The effect of the combination of treatments (thermal and vascular) is represented schematically in FIG. 18. An upper region, marked in the figure with a dashed line, is subjected to vascular coagulation by the vascular treatment, and a low region, marked with a solid line, is heated by the thermal laser. A region of overlap, marked with diagonal lines, is significantly affected by both modalities. It will be appreciated that the actual extent of each of the two treatments will be dependent on choice of wavelength, fluence, pulse duration, cooling, as well as the characteristics of the lesion and the skin where it is located. An important aspect of the combination of the two treatment modalities is that the treatments may be temporally separated, with intervening skin cooling in some embodiments, so that nonselective heating by the vascular laser is substantially prevented in the region of overlap. The mechanism of action of the vascular and thermal treatments are different, allowing the two to be combined in either order to selectively eradicate tumor cells throughout the entire tumor from epidermis to subcutaneous tissue. Yet another aspect of the invention is that topical anticancer or chemotherapeutic agents applied to the tissue will (1) be retained longer and penetrate deeper in dermis treated by vascular targeting, (2) further increase the amount of tumor cell death in tumor cells that have been subjected to vascular laser-induced hypoxia and thermal laser-induced heating.

Figure 19:
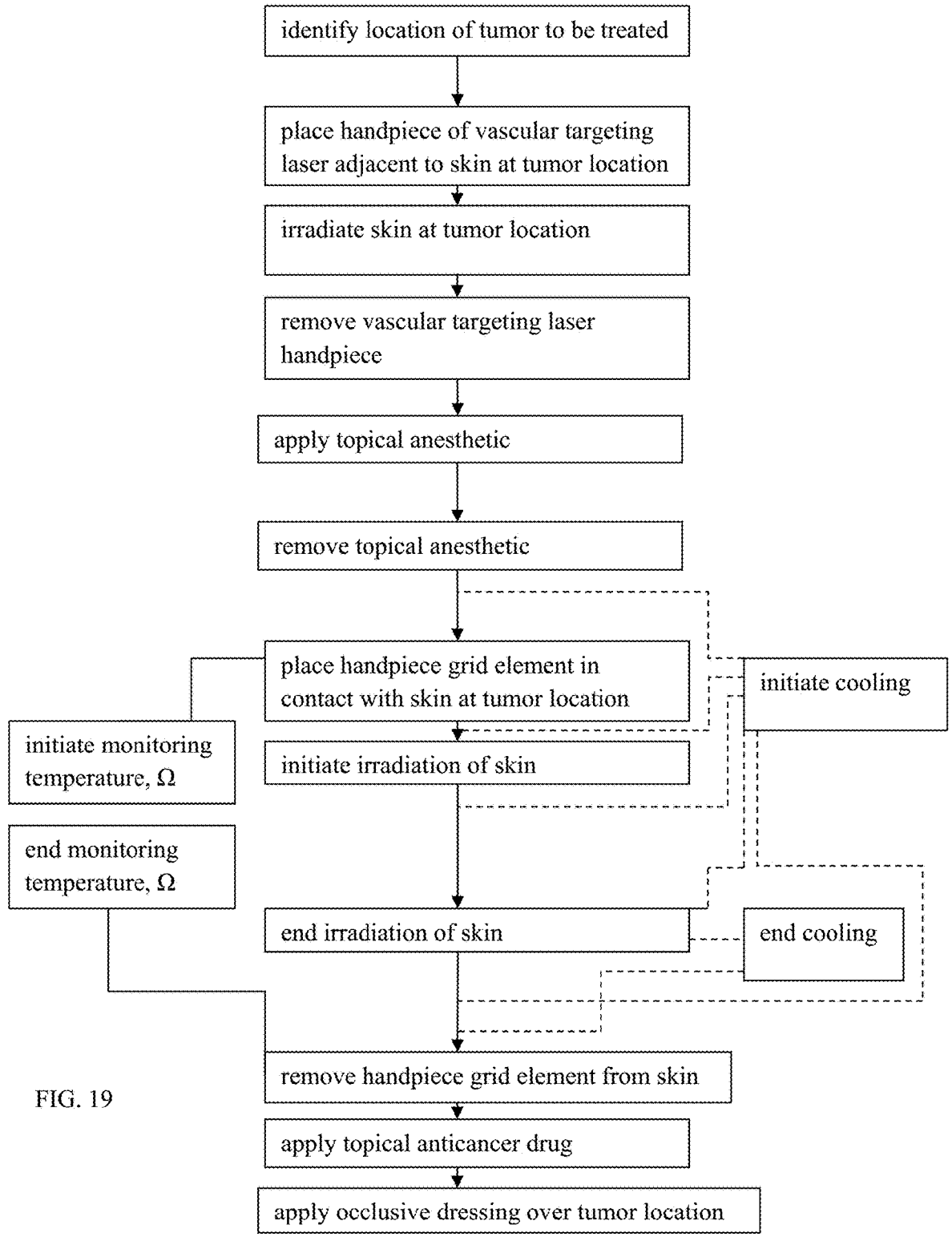
FIG. 19 is a treatment schema of the invention, using vascular laser treatment and topical anesthetic administration, followed by laser thermal therapy, followed by topical anticancer drug administration.

Another treatment schema is shown in FIG. 19, for treatment according to the invention with thermal therapy, vascular targeting, and a topical anticancer. In this schema, vascular laser irradiation of a skin tumor is followed by application of topical anticancer drug to the tumor site on the skin. In some advantageous embodiments, an ablation element 30 attached to the vascular laser handpiece 1 produces an array of ablations in at least the stratum corneum of the epidermis of the skin tumor site during vascular laser irradiation, said ablations increasing the permeability of the epidermis. The topical drug is applied immediately after irradiation when the vascular handpiece is removed from the skin surface, or, in advantageous embodiments, after the formation of purpura at the irradiation site. In purpuric skin, dermal permeability is reduced due to a reduction in blood uptake of anticancer drug, to increase dermal drug exposure and reduce possibly deleterious systemic uptake of the drug.

The thermal laser irradiation is applied after the anticancer drug has been on the skin for a sufficient time to achieve therapeutic levels of exposure to at least a portion of the dermis to said drug, at which time the topical drug is removed from the skin. Drug application times may be on the order of minutes to hours, or overnight. Before thermal laser irradiation, the drug is removed from the skin. Thermal laser irradiation is applied with monitoring of temperature and damage Ω, and in advantageous embodiments includes skin cooling. Use of permeability needles may be omitted with in the embodiment the anticancer drug is applied to the skin prior to thermal laser irradiation. Temperature at the location of each sensor needle is monitored to ensure that the tumor cells have been exposed to a thermal history that corresponds to a large damage integral Ω, for example a Ω of at least approximately 2, and more advantageously greater than 2, for tumor cells, and, secondly, that the damage integral Ω for normal dermal collagen that is less than approximately 1.5 at the location of each sensor needle. In embodiments of the invention depicted in the schema of FIG. 19, highly effective and selective tumor treatment is achieved with a combination of indirect tumor cell killing by hypoxia induced by vascular targeting, direct thermal injury to tumor cells by thermal laser irradiation, and direct tumor cell killing by the cytotoxic or anticancer drug.

Figure 20:
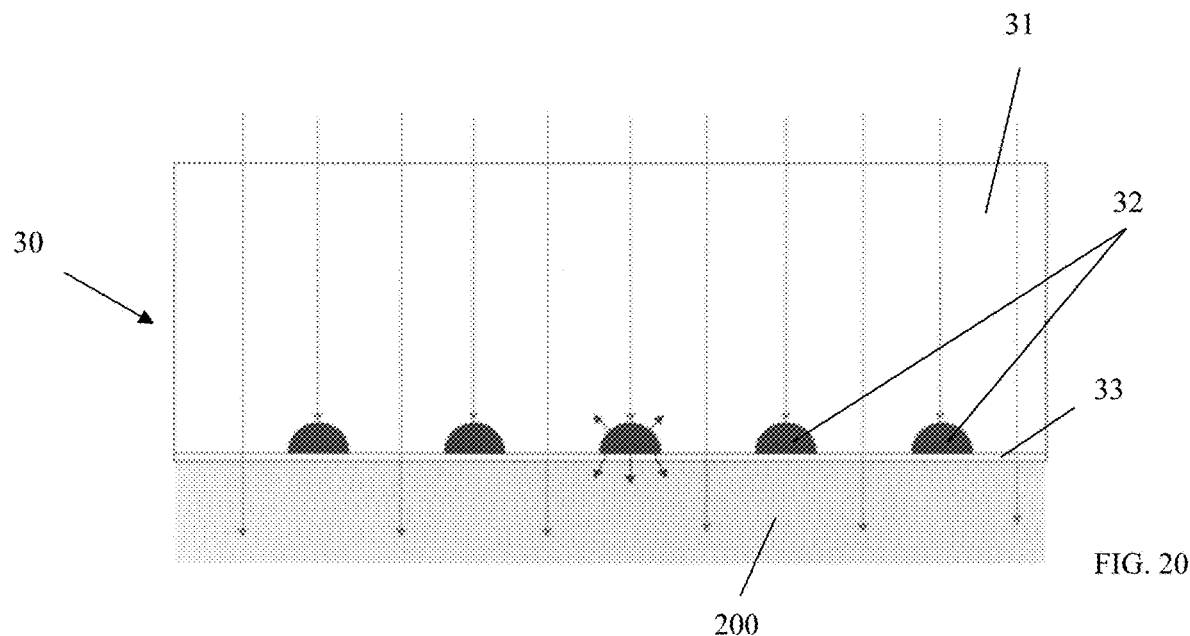
FIG. 20 is a schematic representation of an ablation element 30 of the invention.

In some embodiments of the present invention, the vascular laser treatment will include an ablation element attached to the distal end of the vascular targeting handpiece to increase the permeability of the epidermis of the skin. Ablation elements were described in WO/2010/102099A1 Method and Apparatus for Cancer Therapy. The concept of the ablation element is shown in the embodiment of FIG. 20. The ablation element 30 consists of a substantially transparent substrate 31, with an array of embedded chromophore material elements 32, with a substantially transparent contact window 33 covering said chromophore material elements. The ablation element transmits a substantial portion of the light from the vascular targeting laser to the skin 200 unimpeded. In some embodiments the ablation element transmits at least approximately 20% of the light through said element to the skin. In more advantageous embodiments the ablation element transmits at least 40% of the light. In yet more advantageous embodiments the ablation element transmits at least 70% of the light. The portion of light from the vascular targeting laser handpiece that impinges on and is absorbed by the chromophore material elements 32 serves to heat said material. In this manner the ablation element serves to produce an array of hot spots on the contact window 33 that will ablate spots on the surface of the skin 200. In advantageous embodiments, the chromophore material elements 32 will be heated to a temperature of at least approximately 100° C. by the vascular targeting laser light impinging on said elements.

It has been found that the ablation element substrate 31 may be made of a material with relatively low thermal conductivity, such as silica or quartz, and the contact window 33 made of material with high thermal conductivity, such as sapphire. In this way, heat is transferred efficiently to the skin, rather than diffusing into the substrate 31. In advantageous embodiments, the contact window 33 has a thickness that is less than the distance between chromophore material elements 32, to minimize lateral heat diffusion in the contact window 33.

Figure 21:
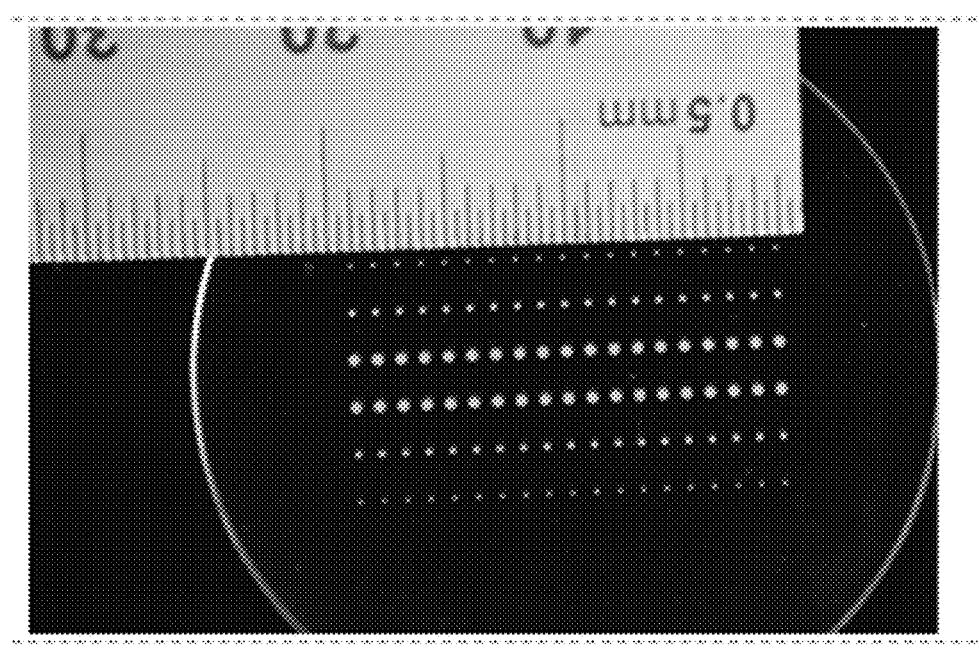
FIG. 21 is a photograph showing features of the substrate 31 of an ablation element 30.

FIG. 21 shows that small holes can be created in fused silica, in the 100 □m to 500 □m size range, or larger. These holes are then filled with a chromophore material, for example amorphous carbon or iron oxide. An advantageous aspect of the ablation element is that the chromophore is not in contact with the skin. The ablation element can be cleaned and reused.

In some advantageous embodiments, the vascular targeting treatment includes an ablation element and application of a topical anesthetic. Light from the vascular laser with ablation element is applied to the skin, and has two effects: (1) the vascular laser light damages the microvasculature of the skin tumor leading to tumor cell injury and death, and (2) modification of skin permeability by coagulation of dermal microvasculature and production of ablations in the epidermis serves to increase the exposure of dermal tissue to applied drugs. Effect (2) was described in WO/2010/102099A1 Method and Apparatus for Cancer Therapy, Application of the vascular laser treatment before the thermal laser has the advantage that with the modification of dermal permeability to topical drugs, the procedure can be used to either anesthetize the skin prior to the thermal laser treatment, to expose the dermis in the vicinity or the skin tumor to anticancer drugs, or both.

In advantageous embodiments, when vascular laser irradiation is used, the time between vascular laser irradiation and topical drug application is sufficient for purpura to form from the vascular laser treatment, or at least approximately 10 min. Purpura is indicate of a reduction in dermal permeability to topically applied anesthetic or anticancer drug, such that dermal exposure to said drug is increased. Also, because erythema indicative of increased blood flow is a common acute effect of vascular laser irradiation, the time between vascular laser irradiation and topical drug application is sufficient for the erythema to subside, or approximately 20 min.

Figure 22:
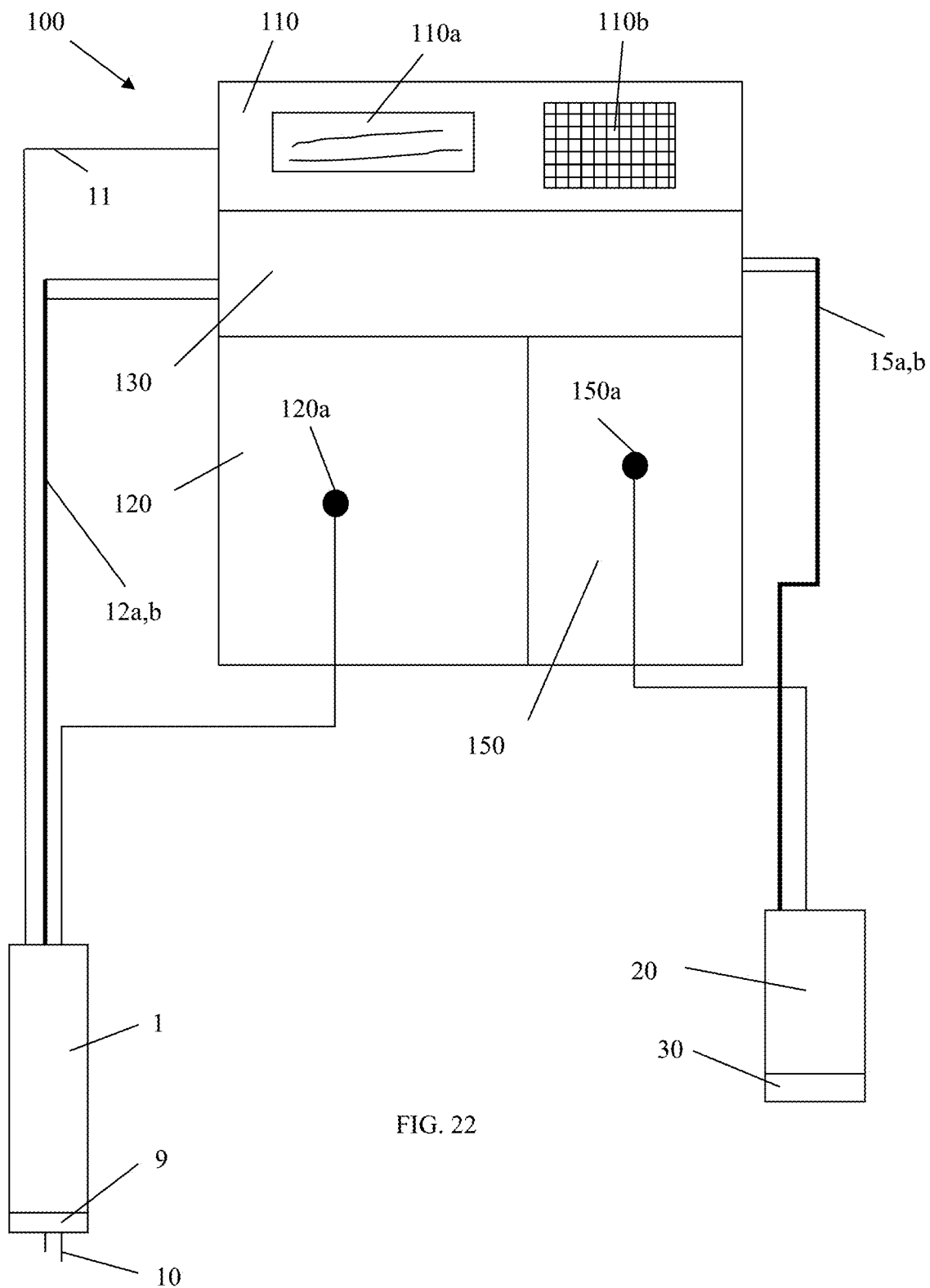
FIG. 22 is a schematic view of an apparatus 100 of the invention, in which a thermal laser 120 is combined with a vascular laser 150.

FIG. 22 shows an example of an embodiment of the present invention. The apparatus 100 includes two light sources: a vascular treatment device 150 (for example, a pulsed dye laser, a KTP laser, or a intense pulsed light source (IPL)), and a thermal therapy laser device 120. Devices 150 and 120 have light output ports 150*a* and 120*a*, respectively, for coupling of optical fibers to the respective handpieces. The thermal therapy laser has a controller 110 that takes signals from the leads 11 of temperature sensors 10 of the detachable grid element 9 of the thermal therapy laser handpiece 1 and monitors accumulating damage in dermal collagen and tumor cells during thermal therapy, providing information on this accumulating damage to the operator via a display 110*a*, indicators, and/or alarms. This allows the operator to control the thermal therapy treatment process so that substantial tumor cell death occurs without substantial damage to normal dermis. The vascular treatment device has a handpiece 20 that may have an ablation element 30, as described in WO/2010/102099A1, to increase permeability of a topical agent applied to the skin. The apparatus may also comprise a cooling system 130, for cooling the windows of the thermal therapy handpiece and/or the ablation element of the vascular handpiece. Coolant lines 15*a* and 15*b* of the vascular handpiece, and coolant lines 12*a* and 12*b* of the thermal therapy handpiece may be connected to cooling system 130.

Figure 23:
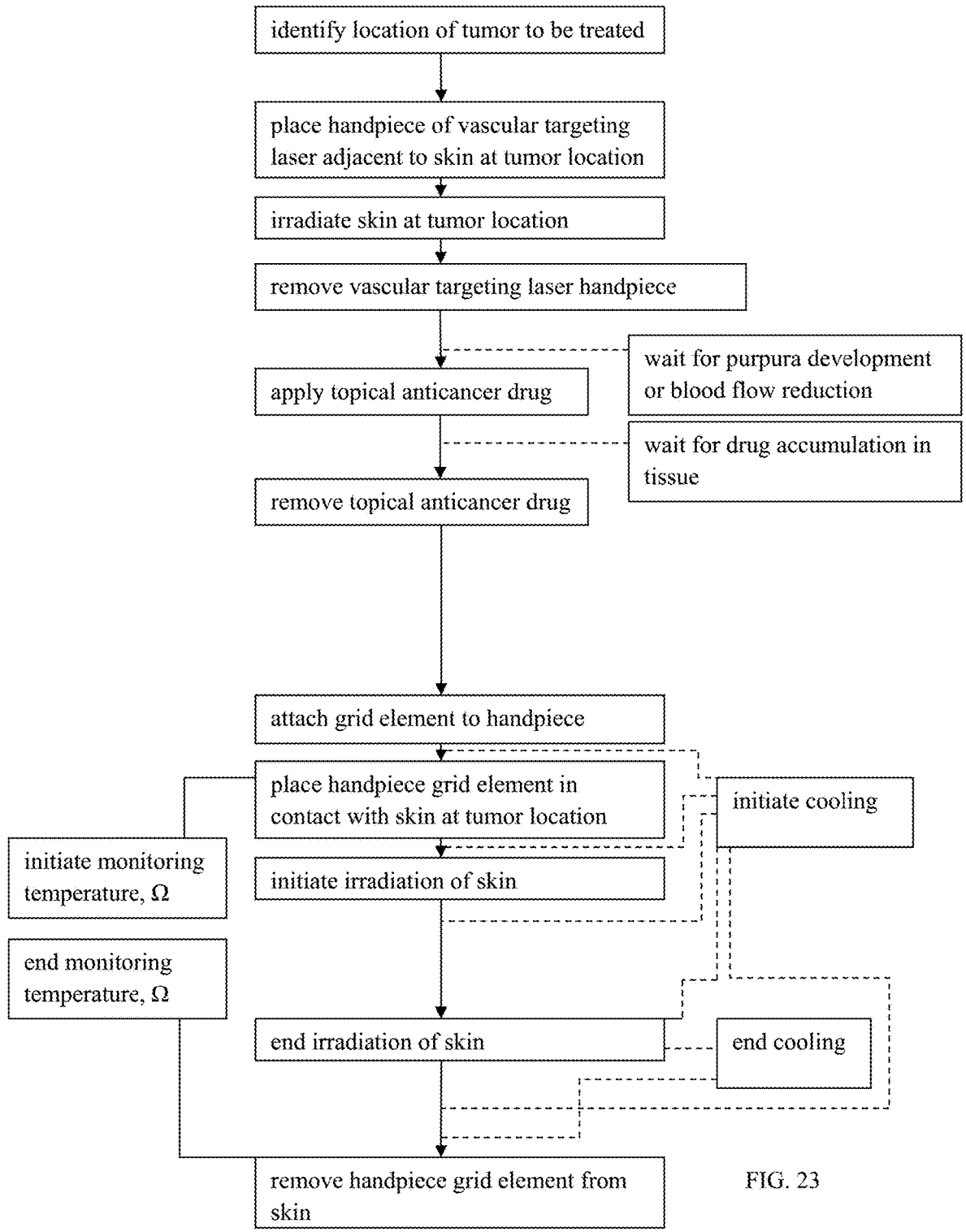
FIG. 23 is a treatment schema of the invention, using vascular laser treatment and topical anticancer drug application, followed by laser thermal therapy.

Another treatment schema is shown in FIG. 23, for treatment according to the invention with thermal therapy, vascular targeting, and a topical anesthetic agent. In this schema, vascular laser irradiation of a skin tumor is followed by application of topical anesthetic to the tumor site on the skin. In some advantageous embodiments, an ablation element attached to the vascular laser handpiece produces an array of ablations in at least the stratum corneum of the epidermis of the skin tumor site during vascular laser irradiation, said ablations increasing the permeability of the epidermis. The topical agent is applied immediately after irradiation when the vascular handpiece is removed from the skin surface, or, in some embodiments, after the formation of purpura at the irradiation site. In purpuric skin, dermal permeability is reduced due to a reduction in blood uptake of anesthetic drug, to increase dermal drug exposure and reduce possibly deleterious systemic uptake of the drug. The thermal laser irradiation is applied after the anesthetic drug has been on the skin for a sufficient time to produce numbing of the treatment site, at which time the topical drug is removed from the skin. Thermal laser irradiation is applied to the purpuric skin with monitoring of temperature and damage $\Omega$, and in advantageous embodiments includes skin cooling. Temperature at the location of each sensor needle is monitored to ensure that the tumor cells have been exposed to a thermal history that corresponds to a large damage integral $\Omega$, for example a $\Omega$ of at least approximately 2, and more advantageously greater than 2, for tumor cells, and, secondly, that the damage integral $\Omega$ for normal dermal collagen that is less than approximately 1.5 at the location of each sensor needle. A topical anticancer drug is applied immediately after thermal laser irradiation, covered with a dressing, and is allowed to remain on the skin to achieve therapeutic exposure at the tumor site. In advantageous embodiments, the topical anticancer drug remains on the skin at the tumor treatment site for a period of at least one hour, more advantageously at least about 4 hours, and more advantageously at least about 8 hours or overnight, at which time the dressing is removed and the drug washed off. In embodiments of the invention depicted in the schema of FIG. 23, highly effective and selective tumor treatment is achieved with a combination of indirect tumor cell killing by hypoxia induced by vascular targeting, direct thermal injury to tumor cells by thermal laser irradiation, and direct tumor cell killing by the cytotoxic or anticancer drug, with a concomitant reduction in pain from the thermal laser irradiation.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treatment of soft tissue, comprising:
   transmitting radiation emitted from a source of radiation to a region of soft tissue via a handpiece, said handpiece adapted to be positioned adjacent to or in contact with said soft tissue region;
   holding a single temperature sensor at a particular location in contact with or embedded in said region of soft tissue, the single temperature sensor producing a single temperature signal for a duration of a time interval;
   calculating, by a microprocessor, a first measure of two different cumulative measures of potential tissue damage at the particular location of the single temperature sensor as a first function of the single temperature signal for the duration of the time interval, the first measure indicative of damage for a normal tissue component potentially present at the particular location of the single temperature sensor in the region of soft tissue, and
   calculating, by the microprocessor, a second measure of the two different cumulative measures of potential tissue damage at the particular location of the single temperature sensor as a second function of the single temperature signal for the duration of the time interval, the second function different from the first function, the second measure indicative of damage for a malignant, premalignant, hypertrophic, diseased, or otherwise unwanted component potentially present at the particular location of the single temperature sensor in the region of soft tissue.

2. The method of claim 1, wherein transmitting radiation from the source of radiation includes using a source of radiation that is a coherent or incoherent source operating in a range of between 700 nm and 1310 nm.

3. The method of claim 1, wherein holding the single temperature sensor includes using a grid element attached to the handpiece.

4. The method of claim 1, wherein holding the single temperature sensor includes holding a thermocouple or thermistor.

5. The method of claim 4, wherein holding the thermocouple or thermistor includes using a needle containing the thermocouple or thermistor and having a proximal end and a distal end, such that the proximal end is affixed to the grid element and the distal end is embedded in the region of soft tissue.

6. The method of claim 1, wherein calculating the first measure indicative of damage for the normal tissue component includes calculating the first measure for collagen.

7. The method of claim 1, wherein calculating the second measure indicative of damage for the unwanted component includes calculating the second measure for tumor cells.

8. The method of claim 1, wherein the normal tissue component is dermal collagen, and the at least one unwanted component is skin cancer cells.

9. The method of claim 1, wherein calculating at least one of the two different cumulative measures of potential tissue damage includes using an Arrhenius damage integral.

10. The method of claim 1, further comprising cooling the region of soft tissue for at least a portion of the time that the temperature sensor is in contact with or embedded in said soft tissue.

11. The method of claim 1, further comprising displaying at least one of the two different cumulative measures of potential tissue damage for at least a portion of the time that the temperature sensor is in contact with or embedded in said soft tissue.

12. The method of claim 1, further comprising holding at least two temperature sensors embedded at least two different depths in the irradiated soft tissue, at least one of the at least two temperature sensors being the single temperature sensor at the particular location in contact with or embedded in the region of soft tissue.

13. The method of claim 1, wherein the duration of the time interval for producing the single temperature signal includes at least one of before transmitting the radiation or after transmitting the radiation.

14. The method of claim 1, wherein the single temperature sensor at the particular location is a first temperature sensor, the method further including holding one or more second temperature sensors at one or more respective locations different from the particular location.

15. The method of claim 1, further comprising topically applying an antineoplastic, anticancer, antiproliferative, antiangiogenic, bioreductive, immunomodulatory, prodifferentiative, antioxidant, nonsteroidal anti-inflammatory, COX inhibitor, or cytotoxic drug to the region of soft tissue before radiation is transmitted.

16. The method of claim 1, further comprising topically applying an antineoplastic, anticancer, antiproliferative, antiangiogenic, bioreductive, immunomodulatory, prodifferentiative, antioxidant, nonsteroidal anti-inflammatory, COX inhibitor, or cytotoxic drug to the region of soft tissue after transmitting the radiation.

17. A method of heating biological tissue by application of radiation, the method comprising:
   initiating irradiation of a treatment region of the tissue;
   measuring temperature at a location in the treatment region, using a single temperature sensor, the single temperature sensor producing a single temperature signal for a duration of a time interval to form a thermal history from the single temperature sensor at the location in the treatment region;
   calculating, based on the thermal history from the single temperature sensor at the location, at least two measures of potential thermal injury at the location in the treatment region, a first one of the at least two measures corresponding to a normal tissue component potentially present at the location in the treatment region for the duration of the time interval, and a second one of the at least two measures corresponding to an unwanted tissue component potentially present at the location in the treatment region for the duration of the time interval;
   ending irradiation of the treatment region responsive to the second measure of potential thermal injury corresponding to substantial thermal injury of the unwanted tissue component potentially present at the location.

18. The method of claim 17, wherein the irradiation of the treatment region includes using a pulsed, intermittently halted, modulated, or continuous source of radiation in a range of between 700 nm and 1310 nm.

19. The method of claim 17, wherein ending irradiation is further responsive to the first measure of potential thermal injury corresponding to the normal tissue component potentially present at the location being substantially uninjured by heat.

20. The method of claim 17, wherein measuring the temperature at a particular location includes obtaining a signal from a sensor, said signal corresponding to the temperature at the particular location.

21. The method of claim 20, wherein the sensor is a thermocouple or thermistor placed on or embedded within the treatment region.

22. The method of claim 20, wherein the sensor is a noncontact sensor that detects radiation emitted from the treatment region.

23. The method of claim 17, wherein measuring the temperature at a particular location in the treatment region includes measuring the temperature at times (1) after initiating irradiation and (2) after ending irradiation and before the tissue has cooled to a temperature at which accumulation of thermal injury substantially ceases.

24. The method of claim 17, wherein calculating the at least two measures of potential thermal injury at the location includes (a) using tissue temperature measured at times after initiating irradiation, and (b) calculating a tissue cooling rate and time required for the tissue to cool to a temperature at which accumulation of thermal injury substantially ceases.

25. The method of claim 17, further comprising topically applying an antineoplastic, anticancer, antiproliferative, antiangiogenic, bioreductive, immunomodulatory, prodifferentiative, antioxidant, nonsteroidal anti-inflammatory, COX inhibitor, or cytotoxic drug to the treatment region before initiating irradiation.

26. The method of claim 17, further comprising topically applying an antineoplastic, anticancer, antiproliferative, antiangiogenic, bioreductive, immunomodulatory, prodifferentiative, antioxidant, nonsteroidal anti-inflammatory, COX inhibitor, or cytotoxic drug to the treatment region after ending irradiation.

27. The method of claim 17, further including inducing selective injury to blood vessels of the treatment region before initiating irradiation.

28. The method of claim 17, further including inducing selective injury to blood vessels of the treatment region after ending irradiation.

29. The method of claim 28, wherein inducing selective injury to blood vessels includes using a pulsed dye laser, pulsed KTP laser, frequency doubled Nd: YAG laser, filtered flashlamp, intense pulsed light source, or other vascular treatment light source.

30. The method of claim 17, wherein measuring temperature at the location in the treatment region is discontinuous.

31. The method of claim 17, wherein measuring the temperature at a particular location includes obtaining a signal from a sensor, said signal corresponding to the temperature at the particular location, and removing a portion of said signal.

32. The method of claim 17, further including:
   measuring temperature at a plurality of locations in the treatment region, using respective temperature sensors, to form respective thermal histories from the respective temperature sensors at the respective locations in the treatment region; and
   calculating, based on the respective thermal histories from the respective temperature sensors at the respective locations, at least two measures of potential thermal injury at each of the respective locations in the treatment region, a first one of each of the respective at least two measures corresponding to a normal tissue component potentially present at the respective location in the treatment region, and a second one of each of the respective at least two measures corresponding to an unwanted tissue component potentially present at the respective location in the treatment region.

* * * * *